US 10,798,941 B2

(12) United States Patent
Hoffman et al.

(10) Patent No.: US 10,798,941 B2
(45) Date of Patent: Oct. 13, 2020

(54) MICROBIOCIDAL OXADIAZOLE DERIVATIVES

(71) Applicant: SYNGENTA PARTICIPATIONS AG, Basel (CH)

(72) Inventors: Thomas James Hoffman, Stein (CH); Daniel Stierli, Stein (CH); André Jeanguenat, Stein (CH); Renaud Beaudegnies, Stein (CH); Martin Pouliot, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/068,638

(22) PCT Filed: Jan. 5, 2017

(86) PCT No.: PCT/EP2017/050193
§ 371 (c)(1),
(2) Date: Jul. 6, 2018

(87) PCT Pub. No.: WO2017/118689
PCT Pub. Date: Jul. 13, 2017

(65) Prior Publication Data
US 2019/0297892 A1   Oct. 3, 2019

(30) Foreign Application Priority Data

Jan. 8, 2016   (EP) .................................... 16150684
Jul. 8, 2016   (EP) .................................... 16178689

(51) Int. Cl.
*A01N 43/90* (2006.01)
*A01N 43/82* (2006.01)
*A01N 43/84* (2006.01)
*C07D 413/10* (2006.01)
*C07D 413/14* (2006.01)
*C07D 417/10* (2006.01)
*C07D 471/04* (2006.01)
*C07D 473/08* (2006.01)

(52) U.S. Cl.
CPC ............. *A01N 43/90* (2013.01); *A01N 43/82* (2013.01); *A01N 43/84* (2013.01); *C07D 413/10* (2013.01); *C07D 413/14* (2013.01); *C07D 417/10* (2013.01); *C07D 471/04* (2013.01); *C07D 473/08* (2013.01)

(58) Field of Classification Search
CPC ............................. C07D 413/10; A01N 43/90
See application file for complete search history.

(56) References Cited

U.S. PATENT DOCUMENTS

| | | | | |
|---|---|---|---|---|
| 9,056,843 | B2 * | 6/2015 | Hebach | C07D 271/06 |
| 10,118,906 | B2 * | 11/2018 | Wieja | C07D 417/12 |
| 10,442,777 | B2 * | 10/2019 | Wieja | C07D 413/12 |

FOREIGN PATENT DOCUMENTS

| | | |
|---|---|---|
| CN | 1927860 A | 3/2007 |
| EP | 0276432 A2 | 8/1988 |
| EP | 3165093 A1 | 5/2017 |
| EP | 3165094 A1 | 5/2017 |
| EP | 3187497 A1 | 7/2017 |
| JP | 2017190296 A | 10/2017 |
| WO | 2008037789 A1 | 4/2008 |
| WO | 2011088181 A1 | 7/2011 |
| WO | 2011088192 A1 | 7/2011 |
| WO | 2011101402 A1 | 8/2011 |
| WO | 2012052490 A1 | 4/2012 |
| WO | 2013006408 A1 | 1/2013 |
| WO | 2013008162 A1 | 1/2013 |
| WO | 2013009810 A1 | 1/2013 |
| WO | 2013009827 A1 | 1/2013 |
| WO | 2013009830 A1 | 1/2013 |
| WO | 2013064079 A1 | 5/2013 |
| WO | 2013066835 A2 | 5/2013 |
| WO | 2013066839 A2 | 5/2013 |
| WO | 2013080120 A1 | 6/2013 |
| WO | 2015055706 A2 | 4/2015 |
| WO | 2015185485 A1 | 12/2015 |
| WO | 2017033946 A1 | 3/2017 |
| WO | 2017076739 A1 | 5/2017 |
| WO | 2017076740 A1 | 5/2017 |
| WO | 2017076742 A1 | 5/2017 |
| WO | 2017076757 A1 | 5/2017 |
| WO | 2017076935 A1 | 5/2017 |
| WO | 2017081309 A1 | 5/2017 |
| WO | 2017081310 A1 | 5/2017 |
| WO | 2017081311 A1 | 5/2017 |
| WO | 2017081312 A1 | 5/2017 |
| WO | 2017085098 A1 | 5/2017 |
| WO | 2017085100 A1 | 5/2017 |

(Continued)

OTHER PUBLICATIONS

Extended European Search Report for Application No. 16178689.2, dated Sep. 5, 2016.

(Continued)

*Primary Examiner* — Golam M Shameem
(74) *Attorney, Agent, or Firm* — Baker & Hostetler, LLP; Toni-Junell Herbert

(57) ABSTRACT

Compounds of the formula (I) wherein the substituents are as defined in claim 1, useful as a pesticides, especially fungicides.

14 Claims, No Drawings

(56) References Cited

FOREIGN PATENT DOCUMENTS

| WO | 2017093019 A1 | 6/2017 |
| --- | --- | --- |
| WO | 2017093348 A1 | 6/2017 |
| WO | 2017110861 A1 | 6/2017 |
| WO | 2017110862 A1 | 6/2017 |
| WO | 2017110864 A1 | 6/2017 |
| WO | 2017110865 A1 | 6/2017 |
| WO | 2017111152 A1 | 6/2017 |
| WO | 2017169893 A1 | 10/2017 |
| WO | 2017178245 A1 | 10/2017 |
| WO | 2017211649 A1 | 12/2017 |
| WO | 2017211650 A1 | 12/2017 |
| WO | 2017211652 A1 | 12/2017 |
| WO | 2017213252 A1 | 12/2017 |
| WO | 2017222951 A1 | 12/2017 |
| WO | 2018030460 A1 | 2/2018 |

OTHER PUBLICATIONS

International Search Report for International Patent Application No. PCT/EP2017/050193, dated Feb. 27, 2017.

\* cited by examiner

MICROBIOCIDAL OXADIAZOLE DERIVATIVES

CROSS-REFERENCE TO RELATED APPLICATIONS

This application is a 371 National Stage application of International Application No. PCT/EP2017/050193, filed Jan. 5, 2017, which claims priority to European Patent Application No. 16150684.5, filed Jan. 8, 2016, and European Patent Application No. 16178689.2, filed Jul. 8, 2016, the entire contents of which applications are hereby incorporated by reference.

The present invention relates to microbiocidal oxadiazole derivatives, eg, as active ingredients, which have microbiocidal activity, in particular, fungicidal activity. The invention also relates to agrochemical compositions which comprise at least one of the oxadiazole derivatives and to uses of the oxadiazole derivatives or compositions in agriculture or horticulture for controlling or preventing infestation of plants, harvested food crops, seeds or non-living materials by phytopathogenic microorganisms, preferably fungi.

WO 2015/185485 describes the use of substituted oxadiazoles for combating phytopathogenic fungi.

According to the present invention, there is provided a compound of formula (I):

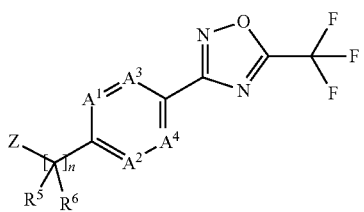

wherein
n is 1 or 2;
$A^1$ represents N or $CR^1$, wherein $R^1$ represents hydrogen, halogen, methyl, ethyl, difluoromethyl, trifluoromethyl, methoxy, ethoxy, or difluoromethoxy;
$A^2$ represents N or $CR^2$, wherein $R^2$ represents hydrogen, halogen, methyl, ethyl, difluoromethyl, trifluoromethyl, methoxy, ethoxy, or difluoromethoxy;
$A^3$ represents N or $CR^3$, wherein $R^3$ represents hydrogen or halogen;
$A^4$ represents N or $CR^4$, wherein $R^4$ represents hydrogen or halogen; and
wherein 0 or 1 or 2 of $A^1$, $A^2$, $A^3$ and $A^4$ are N;
$R^5$ and $R^6$ are independently selected from hydrogen, $C_{1-4}$alkyl, halogen, cyano, trifluoromethyl and difluoromethyl, or
$R^5$ and $R^6$ together with the carbon atom they share form a cyclopropyl;
Z is selected from $Z^1$, $Z^2$, $Z^3$, $Z^4$, $Z^5$ or $Z^6$; wherein
$Z^1$ represents a heterocyclyl linked to $C(R^5)(R^6)$ via a C—C bond, wherein the heterocyclyl moiety is a 5- or 6-membered non-aromatic ring which contains 1 nitrogen in the ring system and optionally comprises 1, 2, or 3 additional ring members independently selected from the group consisting of O, S, N, $NR^7$, C(O), or $S(O)_2$, with the proviso that the heterocycle cannot contain 2 contiguous atoms selected from O and S;
$Z^2$ represents a heteroaryl linked to $C(R^5)(R^6)$ via a C—C bond, wherein the heteroaryl moiety is a 5- or 6-membered aromatic ring which contains 1 nitrogen atom in the ring system and optionally comprises 1, 2, or 3 additional ring members independently selected from the group consisting of O, S, N, or $NR^7$;
$R^7$ is hydrogen, $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, N,N-di$C_{1-4}$alkylaminocarbonyl, $C_{1-4}$alkylsulfonyl, N—$C_{1-2}$alkylaminosulfonyl, or N,N-di$C_{1-2}$alkylaminosulfonyl; and
wherein for $Z^1$ and $Z^2$, the heterocyclyl or heteroaryl moiety is optionally substituted by 1, 2 or 3 substituents, which may be the same or different, selected from $R^8$;
$R^8$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{1-4}$alkoxycarbonylamino;
$Z^3$ represents a heterocyclyl linked to $C(R^5)(R^6)$ via a C—N bond, wherein the heterocyclyl moiety is a 5- or 6-membered non-aromatic ring which contains 1 nitrogen in the ring system and optionally comprises 1, 2, or 3 additional ring members independently selected from the group consisting of O, S, N, $NR^9$ or C(=N—O—$C_{1-4}$alkyl), with the proviso that the heterocycle cannot contain 2 contiguous atoms selected from O and S;
$Z^4$ represents a heteroaryl linked to $C(R^5)(R^6)$ via a C—N bond, wherein the heteroaryl moiety is a 5-membered aromatic ring which contains 1 to 4 nitrogen atoms in the ring system;
$R^9$ is hydrogen, $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, or N,N-di$C_{1-4}$alkylaminocarbonyl; and
wherein for $Z^3$ and $Z^4$, the heterocyclyl or heteroaryl moiety is optionally substituted by 1, 2 or 3 substituents, which may be the same or different, selected from $R^{10}$;
wherein $R^{10}$ represents:
(i) cyano, halogen, hydroxy, amino, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$alkylsulfanyl, $C_{1-4}$haloalkoxy, $C_{1-4}$alkylsulfanyl, $C_{1-4}$alkylsulfinyl, $C_{1-4}$alkylsulfonyl, $C_{1-4}$haloalkylsulfanyl, $C_{3-4}$alkenyloxy, $C_{3-4}$alkynyloxy, N—$C_{1-4}$alkylamino, N,N-di$C_{1-4}$alkylamino, formyl, hydroxycarbonyl, $C_{1-4}$alkylcarbonyl, $C_{1-4}$alkoxycarbonyl, $C_{1-4}$alkylcarbonylamino, aminocarbonyl, N—$C_{1-4}$alkylaminocarbonyl, N—$C_{2-4}$alkenylaminocarbonyl, N—$C_{2-4}$alkynylaminocarbonyl, N,N-di$C_{1-4}$alkylaminocarbonyl, N-morpholinoaminocarbonyl, N—$C_{1-4}$alkoxyaminocarbonyl, N—$C_{1-4}$alkyl-N—$C_{1-4}$alkoxyaminocarbonyl, $C_{1-4}$alkoxycarbonylamino, $C_{1-4}$alkoxycarbonylamino$C_{1-4}$alkyl, N—$C_{1-4}$alkoxy$C_{1-4}$alkylaminocarbonyl, phenylcarbonyloxy$C_{1-4}$alkyl, phenylcarbonylamino$C_{1-4}$alkyl, $C_{1-4}$alkylcarbonyloxy, $C_{1-4}$haloalkylcarbonyloxy, $C_{1-4}$alkylcarbonyloxy$C_{1-4}$alkyl, $C_{1-4}$alkylcarbonylamino$C_{1-4}$alkyl, ($C_{1-4}$alkyl)$_3$Si—; or
(ii) —C(O)N($R^a$)($R^b$), wherein:
$R^a$ is hydrogen, $C_{1-4}$alkyl, $C_{1-4}$haloalkyl, $C_{1-4}$cyanoalkyl, hydroxy$C_{1-4}$alkyl, $C_{1-2}$alkoxy$C_{1-4}$alkyl, $C_{1-2}$haloalkoxy$C_{1-4}$alkyl, $C_{3-5}$alkenyl, $C_{3-5}$-alkynyl, amino$C_{1-4}$alkyl, N—$C_{1-4}$alkylamino$C_{1-4}$alkyl, N,N-di$C_{1-4}$alkylamino$C_{1-4}$alkyl, formyl, $C_{1-4}$alkylcarbonyl, $C_{1-4}$cycloalkylcarbonyl, $C_{1-4}$haloalkylcarbonyl, $C_{1-4}$alkylcarbonyl$C_{1-4}$alkyl, $C_{1-4}$alkoxycarbonyl$C_{3-4}$alkyl, $C_{1-4}$alkylcarbonyloxy$C_{1-4}$alkyl, N—$C_{1-4}$alkylaminocarbonyl$C_{1-4}$alkyl, N,N-di$C_{1-4}$alkylaminocarbonyl$C_{1-4}$alkyl, $C_{1-4}$alkylsulfanyl$C_{1-4}$alkyl, $C_{1-4}$alkylsulfonyl, $C_{1-4}$alkylsulfonyl$C_{1-4}$alkyl, $C_{1-4}$alkylsulfonylamino $C_{1-4}$alkyl, $C_{1-4}$alkoxycarbonylamino$C_{1-4}$alkyl, $C_{1-4}$alkylcarbonylamino$C_{1-4}$alkyl, $C_{1-4}$alkoxycarbonylamino$C_{1-4}$alkyl, or $C_{1-4}$haloalkylcarbonylamino$C_{1-4}$alkyl, and $R^b$ is hydrogen, hydroxyl, $C_{1-4}$alkyl, $C_{1-4}$haloalkyl, $C_{1-4}$cyanoalkyl, hydroxy$C_{1-4}$alkyl, $C_{1-2}$alkoxy$C_{1-4}$alkyl, $C_{3-4}$alkenyl, $C_{3-4}$alkynyl, $C_{3-4}$cycloalkyl, $C_{3-4}$cycloalkyl$C_{1-2}$ alkyl, $C_{1-4}$alkoxy, $C_{3-4}$alkenyloxy, $C_{3-4}$haloalkenyloxy, $C_{3-4}$alkynyloxy; or $R^a$ and $R^b$ together with the nitrogen atom to which they are bonded, form a 4-, 5- or 6-membered cycle optionally containing an additional heteroatom or group selected from O, S, $S(O)_2$, C(O) and $NR^c$, wherein $R^c$ is hydrogen, methyl, methoxy, formyl or acyl; or (iii) —C(O)O—$R^d$, wherein:

$R^d$ is hydrogen, $C_{1-4}$alkyl, $C_{1-4}$haloalkyl, $C_{1-4}$cyanoalkyl, hydroxy$C_{1-4}$alkyl, $C_{1-2}$alkoxy$C_{1-4}$alkyl, $C_{1-2}$alkoxy$C_{1-2}$alkoxy$C_{1-4}$alkyl, $C_{1-2}$haloalkoxy$C_{1-4}$alkyl, $C_{3-5}$alkenyl, $C_{3-4}$haloalkenyl, $C_{3-4}$alkenyloxy$C_{1-4}$alkyl, $C_{3-5}$alkynyl, $C_{3-4}$alkynyloxy$C_{1-4}$alkyl, N—$C_{1-3}$alkylamino$C_{1-4}$alkyl, N,N-di-$C_{1-3}$alkylamino$C_{1-4}$alkyl, $C_{1-4}$alkoxycarbonylamino$C_{1-4}$alkyl or $C_{1-4}$alkylcarbonylamino$C_{1-4}$alkyl; or wherein for $Z^4$, the heteroaryl moiety is optionally substituted by 1 substituent selected from $R^{11}$ and further optionally substituted by 1 or 2 substituents, which may be the same or different, selected from $R^{10}$;

wherein $R^{11}$ represents:

(i) $C_{3-8}$cycloalkyl, $C_{3-8}$cycloalkyl$C_{1-2}$alkyl, N—$C_{3-8}$cycloalkylaminocarbonyl, N—$C_{3-8}$cycloalkyl$C_{1-2}$alkylaminocarbonyl, phenyl, phenyl$C_{1-2}$alkyl, phenoxy$C_{1-2}$alkyl, phenyl$C_{1-2}$alkylsulfanyl, heteroaryl, heteroaryl$C_{1-2}$alkyl, heteroaryloxy$C_{1-2}$alkyl, N-heteroarylaminocarbonyl, heterocyclylcarbonyl, wherein the heteroaryl moiety is a 5- or 6-membered aromatic ring which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1 or 2 heteroatoms individually selected from N, O and S, benzodioxolyl, and wherein any of said cycloalkyl, phenyl, heteroaryl, heterocyclyl and benzodioxolyl moieties are optionally substituted by 1, 2 or 3 substituents, which may be the same or different, selected from $R^{12}$; or (ii) —C(O)N($R^e$)($R^f$), wherein:

$R^e$ is $C_{3-5}$cycloalkyl, $C_{3-5}$cycloalkyl$C_{1-2}$alkyl, phenyl, phenyl$C_{1-2}$alkyl, heterocyclyl, heterocyclyl$C_{1-2}$alkyl, wherein the heterocyclyl moiety is a 4- to 6-membered non-aromatic ring which comprises 1, 2, or 3 ring members independently selected from the group consisting of O, S, N or $S(O)_2$, with the proviso that the heterocycle cannot contain 2 contiguous atoms selected from O and S, heteroaryl, heteroaryl$C_{1-2}$alkyl, wherein the heteroaryl moiety is a 5- or 6-membered aromatic ring which comprises 1, 2, 3 or 4 heteroatoms individually selected from N, O and S, and wherein the cycloalkyl, phenyl, heterocyclyl or heteroaryl moiety is optionally substituted by 1 or 2 substituents, which may be the same or different, selected from hydroxyl, amino, formyl, acyl, cyano, halogen, methyl, difluoromethyl, trifluoromethyl, methoxy, ethoxy, or difluoromethoxy, or the cycloalkyl or heterocyclyl moiety is optionally substituted by 1 or 2 groups which are oxo (=O), and $R^f$ is hydrogen, $C_{1-4}$alkyl, $C_{1-4}$alkoxy $C_{1-4}$haloalkyl, $C_{3-4}$alkenyl, $C_{3-4}$alkynyl, $C_{3-4}$cycloalkyl, $C_{3-4}$cycloalkyl$C_{1-2}$ alkyl; or (iii) —C(O)O—$R^g$, wherein:

$R^g$ is $C_{3-5}$cycloalkyl, $C_{3-5}$cycloalkyl$C_{1-2}$alkyl, phenyl, phenyl$C_{1-2}$alkyl, heterocyclyl, heterocyclyl$C_{1-2}$alkyl, wherein the heterocyclyl moiety is a 4- to 6-membered non-aromatic ring which comprises 1, 2, or 3 ring members independently selected from the group consisting of O, S, N or $S(O)_2$, with the proviso that the heterocycle cannot contain 2 contiguous atoms selected from O and S, heteroaryl, heteroaryl$C_{1-2}$alkyl, wherein the heteroaryl moiety is a 5- or 6-membered aromatic ring which comprises 1, 2, 3 or 4 heteroatoms individually selected from N, O and S, and wherein the cycloalkyl, phenyl, heterocyclyl or heteroaryl moiety is optionally substituted by 1 or 2 substituents, which may be the same or different, selected from hydroxyl, formyl, acyl, cyano, halogen, methyl, difluoromethyl, trifluoromethyl, methoxy, ethoxy, or difluoromethoxy, or the cycloalkyl or heterocyclyl moiety is optionally substituted by 1 or 2 groups which are oxo (=O); or (iv) ($C_{1-4}$alkyl)-O—N=C($R^h$)—, ($C_{1-4}$haloalkyl)-O—N=C($R^h$)—, ($C_{2-4}$alkenyl)-O—N=C($R^h$), ($C_{2-4}$alkynyl)-O—N=C($R^h$)—, benzyl-O—N=C($R^h$)—, wherein $R^h$ is hydrogen or methyl;

$R^{12}$ is cyano, fluoro, chloro, bromo, methyl, ethyl, formyl, methoxy, ethoxy, difluoromethyl, trifluoromethyl, difluoromethoxy or ethoxycarbonyl;

$Z^5$ represents a heterobicyclyl linked to $C(R^5)(R^6)$ via a C—N bond, wherein the heterobicyclyl moiety is a 7- to 10-membered saturated, partially saturated or partially aromatic fused ring system which contains 1 nitrogen in the ring system and optionally comprises 1, 2, or 3 additional ring members independently selected from the group consisting of O, S, N, $NR^{13}$, C(O) or $S(O)_2$, with the proviso that the heterobicyclyl cannot contain 2 contiguous atoms selected from O and S;

$Z^6$ represents a heterodiaryl linked to $C(R^5)(R^6)$ via a C—N bond, wherein the heterdioaryl moiety is a 9-membered di-aromatic system which contains 1 to 4 nitrogen atoms in the ring system;

$R^{13}$ is hydrogen, $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, or N,N-di$C_{1-4}$alkylaminocarbonyl; and wherein for $Z^5$ and $Z^6$, the heterobicyclyl or heterodiaryl moiety is optionally substituted by 1, 2, 3 or 4 substituents, which may be the same or different, selected from $R^{14}$;

$R^{14}$ is cyano, halogen, hydroxy, formyl, $C_{1-4}$alkyl, $C_{2-4}$alkenyl, $C_{2-4}$alkynyl, $C_{1-4}$haloalkyl, cyano$C_{1-4}$alkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl, or $C_{1-4}$alkoxycarbonylamino, and additionally oxo (=O) for $Z^5$; or wherein for $Z^5$ and $Z^6$, the heterobicyclyl or heterodiaryl moiety is optionally substituted by 1 substituent selected from $R^{15}$ and further optionally substituted by 1 or 2 substituents, which may be the same or different, selected from $R^{14}$;

$R^{15}$ is pyridinyl, benzodioxolyloxy, phenoxy or phenylsulfanyl, wherein phenoxy and phenylsulfanyl are optionally substituted by 1, 2 or 3 substituents, which may be the same or different, selected from chloro, fluoro, bromo, methyl, ethyl, methoxy and ethoxy; or a salt or an N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I).

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, amino means an —NH$_2$ group.

As used herein, hydroxy means an —OH group.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_{1-4}$alkyl" and "$C_{1-2}$alkyl" are to be construed accordingly. A "$C_{1-6}$alkylene", $C_{1-4}$alkylene" or "$C_{1-2}$alkylene" group refers to the corresponding definition of $C_{1-6}$alkyl, $C_{1-4}$alkyl or $C_{1-2}$alkyl, respectively, except that such radical is attached to the rest of the molecule by two single bonds. Examples of $C_{1-6}$alkyl include, but are not limited to, methyl, ethyl, iso-propyl, n-propyl and t-butyl.

As used herein, the term "$C_{1-4}$alkoxy" refers to a radical of the formula —OR$_a$ where R$_a$ is a $C_{1-4}$alkyl radical as generally defined above. Examples of $C_{1-4}$alkoxy include, but are not limited to, methoxy, ethoxy and propoxy.

As used herein, the term "$C_{1-4}$alkoxy$C_{1-4}$alkyl" refers to radical of the formula R$_b$—O—R$_a$— where R$_b$ is a $C_{1-4}$alkyl radical as generally defined above, and R$_a$ is a $C_{1-4}$alkylene radical as generally defined above.

As used herein, the term "$C_{1-4}$alkylsulfanyl" refers to a radical of the formula —SR$_a$ where R$_a$ is a $C_{1-4}$alkyl radical as generally defined above.

As used herein, the term "$C_{1-4}$alkylsulfinyl" refers to a radical of the formula —S(O)R$_a$ where R$_a$ is a $C_{1-4}$alkyl radical as generally defined above.

As used herein, the term "$C_{1-4}$alkylsulfonyl" refers to a radical of the formula —S(O)$_2$R$_a$ where R$_a$ is a $C_{1-4}$alkyl radical as generally defined above.

As used herein, the term "$C_{2-4}$alkenyl" refers to a straight or branched hydrocarbon chain radical group consisting solely of carbon and hydrogen atoms, containing at least one double bond that can be of either the (E)- or (Z)-configuration, having from two to four carbon atoms, which is attached to the rest of the molecule by a single bond. The term "$C_{3-4}$alkenyl" is to be construed accordingly. Examples of $C_{2-4}$alkenyl include, but are not limited to, ethenyl and prop-1-enyl.

As used herein, the term "$C_{2-4}$alkynyl" refers to a straight or branched hydrocarbon chain radical group consisting solely of carbon and hydrogen atoms, containing at least one triple bond, having from two to four carbon atoms, and which is attached to the rest of the molecule by a single bond. The term "$C_{3-4}$alkynyl" is to be construed accordingly. Examples of $C_{2-4}$alkynyl include, but are not limited to, ethynyl, prop-1-ynyl, propargyl (prop-2-ynyl), but-1-ynyl.

As used herein, the term "$C_{3-4}$alkenyloxy" refers to a radical of the formula —OR$_a$ where R$_a$ is a $C_{3-4}$alkenyl radical as generally defined above.

As used herein, the term "$C_{3-4}$alkynyloxy" refers to a radical of the formula —OR$_a$ where R$_a$ is a $C_{3-4}$alkynyl radical as generally defined above.

As used herein, the term "$C_{1-4}$alkoxycarbonyl" refers to a radical of the formula —C(O)OR$_a$ where R$_a$ is a $C_1$-$C_4$alkyl radical as generally defined above.

As used herein, the term "$C_{1-4}$alkylcarbonyl" refers to a radical of the formula —C(O)R$_a$ where R$_a$ is a $C_{1-4}$alkyl radical as generally defined above.

As used herein, the term "formyl" refers to a radical of the formula —C(O)H.

As used herein, the term "hydroxycarbonyl" refers to a radical of the formula —C(O)OH.

As used herein, the term "$C_{1-4}$alkylcarbonyloxy" refers to a radical of the formula —OC(O)R$_a$ where R$_a$ is a $C_{1-4}$alkyl radical as generally defined above.

As used herein, the term "$C_{1-4}$haloalkoxy" refers to a $C_{1-4}$alkoxy group as defined above substituted by one or more of the same or different halogen atoms. Examples of $C_{1-4}$haloalkoxy include, but are not limited to, fluoromethoxy, fluoroethoxy, trifluoromethoxy, trifluoroethoxy.

As used herein, the term "$C_{1-4}$haloalkyl" refers to a $C_{1-4}$alkyl radical as generally defined above substituted by one or more of the same or different halogen atoms. Examples of $C_{1-4}$haloalkyl include, but are not limited to fluoromethyl, fluoroethyl, difluoromethyl and trifluormethyl.

As used herein, the term "$C_{1-4}$haloalkylsulfanyl" refers to a $C_{1-4}$alkylsulfanyl radical as generally defined above substituted by one or more of the same or different halogen atoms.

As used herein, the term "$C_{2-4}$haloalkenyl" refers to a $C_{2-4}$alkenyl radical as generally defined above substituted by one or more of the same or different halogen atoms.

As used herein, the term "$C_{3-8}$cycloalkyl" refers to a stable, monocyclic or bi-cyclic ring radical which is saturated or partially unsaturated and contains 3 to 8 carbon atoms. $C_{3-6}$cycloalkyl is to be construed accordingly. Examples of $C_{3-8}$cycloalkyl include, but are not limited to, cyclopropyl, cyclobutyl, cyclopentyl and cyclohexyl.

As used herein, the term "$C_{3-8}$cycloalkyl$C_{1-2}$alkyl" refers to a $C_{3-8}$cycloalkyl ring as defined above attached to the rest of the molecule by a $C_{1-2}$alkylene radical as defined above. The terms "$C_{3-6}$cycloalkyl$C_{1-2}$alkyl" and "$C_{3-4}$cycloalkyl$C_{1-2}$alkyl" are to be construed accordingly. Examples of $C_{3-8}$cycloalkyl$C_{1-2}$alkyl include, but are not limited to cyclopropyl-methyl, cyclobutyl-ethyl, and cyclopentyl-propyl.

As used herein, the term "$C_{3-8}$cycloalkylaminocarbonyl" refers to a radical of the formula —C(O)NR$_a$ where R$_a$ is a $C_{3-8}$cycloalkyl radical as generally defined above.

As used herein, the term "N—$C_{3-8}$cycloalkyl$C_{1-2}$alkylaminocarbonyl" refers to a radical of the formula —C(O)NR$_a$ where R$_a$ is a $C_{3-6}$-cycloalkyl$C_{1-2}$alkylene radical as defined above.

As used herein, the term "$C_{1-4}$alkoxycarbonylamino" refers to a radical of the formula —NH—C(O)—O—R$_a$ where R$_a$ is a $C_{1-4}$alkyl radical as defined above.

As used herein, the term "$C_{1-4}$alkoxycarbonylamino$C_{1-4}$alkyl" refers to a radical of the formula —R$_a$C(O)NHR$_b$ where R$_a$ is a $C_{1-4}$alkoxy radical as defined above and R$_b$ is a $C_{1-4}$alkylene radical as defined above.

As used herein, the term "$C_{1-4}$alkylcarbonyloxy" refers to a radical of the formula —OC(O)R$_a$ where R$_a$ is a $C_{1-4}$alkyl as generally defined above.

As used herein, the term "$C_{1-4}$alkylcarbonyloxy$C_{1-4}$alkyl" refers to a radical of the formula —R$_a$OC(O)R$_b$ where $R_a$ is a $C_{1-4}$alkylene radical as generally defined above and $R_b$ is a $C_{1-4}$alkyl as generally defined above.

As used herein, oxo means an =O group, eg, a ketonyl (—C(O)—), sulfinyl (—S(O)—) or sulfonyl (—S(O)$_2$—) oxygen.

As used herein, aminocarbonyl means an —C(O)NH$_2$ radical.

As used herein, the term "N—$C_{1-4}$alkylamino" refers to a radical of the formula —NH—$R_a$ where $R_a$ is a $C_{1-4}$alkyl radical as defined above.

As used herein, the term "N,N-di$C_{1-4}$alkylamino" refers to a radical of the formula —N($R_a$)$R_a$ where each $R_a$ is a $C_{1-4}$alkyl radical, which may be the same or different, as defined above.

As used herein, the term "N,N-di$C_{1-4}$alkylaminocarbonyl" refers to a radical of the formula —C(O)N$R_a$($R_a$) where each $R_a$ is a $C_{1-4}$alkyl radical, which may be the same or different, as generally defined above.

As used herein, the term "N—$C_{1-4}$alkylaminocarbonyl" refers to a radical of the formula —C(O)NH$R_a$ where $R_a$ is a $C_{1-4}$alkyl radical as generally defined above.

As used herein, the term "N—$C_{2-4}$alkenylaminocarbonyl" refers to a radical of the formula —C(O)NH$R_a$ where $R_a$ is a $C_{2-4}$alkenyl radical as generally defined above.

As used herein, the term "N—$C_{2-4}$alkynylaminocarbonyl" refers to a radical of the formula —C(O)NH$R_a$ where $R_a$ is a $C_{2-4}$alkynyl radical as generally defined above.

As used herein, the term "N—$C_{1-4}$alkoxy$C_{1-4}$alkylaminocarbonyl" refers to a radical of the formula —C(O)NH$R_a$—O$R_b$ where $R_a$ is a $C_{1-4}$alkylene radical as generally defined above, and $R_b$ is a $C_{1-4}$alkyl radical as generally defined above.

As used herein, the term "N—$C_{1-4}$alkoxyaminocarbonyl, refers to a radical of the formula —C(O)NHO$R_a$ where $R_a$ is a $C_{1-4}$alkyl radical as generally defined above.

As used herein, the term "N—$C_{1-4}$alkyl-N—$C_{1-4}$alkoxyaminocarbonyl, refers to a radical of the formula —C(O)N($R_a$)O$R_b$ where $R_a$ is a $C_{1-4}$alkyl radical as generally defined above, and $R_b$ is a $C_{1-4}$alkyl radical (same or different to $R_a$) as generally defined above.

As used herein, the term "phenylcarbonyloxy$C_{1-4}$alkyl" refers to a radical of the formula $R_b$—C(O)O$R_a$— where $R_b$ is a phenyl radical, and $R_a$ is a $C_{1-4}$alkylene radical as generally defined above.

As used herein, the term "phenylcarbonylamino$C_{1-4}$alkyl" refers to a radical of the formula $R_b$—C(O)NH$R_a$— where $R_b$ is a phenyl radical, and $R_a$ is a $C_{1-4}$alkylene radical as generally defined above.

As used herein, the term "$C_{1-4}$alkylcarbonylamino$C_{1-4}$alkyl" refers to a radical of the formula $R_b$—C(O)NH$R_a$— where $R_b$ is a $C_{1-4}$alkyl radical, and $R_a$ is a $C_{1-4}$alkylene radical as generally defined above.

As used herein, the term "phenyl$C_{1-2}$alkyl" refers to a phenyl ring attached to the rest of the molecule by a $C_{1-2}$alkylene radical as defined above.

As used herein, the term "phenoxy$C_{1-2}$alkyl" refers to a phenoxy ring attached to the rest of the molecule by a $C_{1-2}$alkylene radical as defined above.

As used herein, the term "phenyl$C_{1-2}$alkylsulfanyl" refers to an —S$R_a$ radical wherein $R_a$ is a phenyl$C_{1-2}$alkyl radical as defined above.

As used herein, the term "aryl" refers to an aromatic ring system consisting solely of carbon and hydrogen atoms which may be mono-, bi- or tricyclic. Examples of such ring systems include phenyl, naphthalenyl, anthracenyl, indenyl or phenanthrenyl.

As used herein, the term "heteroaryl" (unless defined otherwise) refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or a heteroatom.

Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryl$C_{1-2}$alkyl" refers to a heteroaryl ring attached to the rest of the molecule by a $C_{1-2}$alkylene radical as defined above.

As used herein, the term "heteroaryloxy$C_{1-2}$alkyl" refers to a radical of the formula —$R_a$O$R_b$ where $R_a$ is a $C_{1-2}$alkylene radical as generally defined above, and $R_b$ is a heteroaryl radical as defined above.

As used herein, the term "heterodiaryl" (unless defined otherwise) refers to a stable 9- or 10-membered bicyclic aromatic ring system which comprises 1, 2, 3 or 4 heteroatoms individually selected from nitrogen, oxygen and sulfur. The heterodiaryl radical may be bonded to the rest of the molecule via a carbon atom or heteroatom. Examples of heterodiaryl include, but are not limited to, indolyl, indazolyl, benzimidazolyl, pyrrolopyridinyl or triazolopyridinyl.

As used herein, the term "heterocyclyl" or "heterocyclic" (unless defined otherwise) refers to a stable 4-, 5- or 6-membered non-aromatic monocyclic ring radical which comprises 1, 2, or 3, heteroatoms individually selected from nitrogen, oxygen and sulfur. The heterocyclyl radical may be bonded to the rest of the molecule via a carbon atom or heteroatom. Examples of heterocyclyl include, but are not limited to, azetidinyl, oxetanyl, pyrrolinyl, pyrrolidyl, thietanyl, tetrahydrofuranyl, tetrahydrothienyl, tetrahydrothiopyranyl, piperidyl, piperazinyl, tetrahydropyranyl, morpholinyl or perhydroazepinyl.

As used herein, the term "heterocyclyl$C_{1-6}$alkyl" refers to a heterocyclyl ring attached to the rest of the molecule by a $C_{1-6}$alkylene radical as defined above. The terms "heterocyclyl$C_{1-4}$alkyl" and "heterocyclyl$C_{1-2}$alkyl" are to be construed accordingly.

As used herein, the term "benzodioxolyl" means a radical as follows:

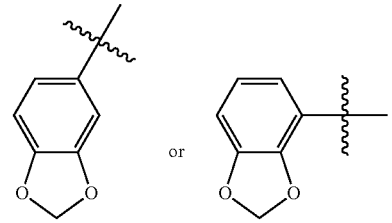 [SMILES: *c1ccc2c(c1)OCO2 ; *c1cccc2c1OCO2]

The presence of one or more possible asymmetric carbon atoms in a compound of formula (I) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I).

Likewise, formula (I) is intended to include all possible tautomers (including lactam-lactim tautomerism and ketoenol tautomerism) where present. The present invention includes all possible tautomeric forms for a compound of formula (I).

In each case, the compounds of formula (I) according to the invention are in free form, in covalently hydrated form, in oxidized form as an N-oxide or in salt form, e.g., an agronomically usable or agrochemically acceptable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The following list provides definitions, including preferred definitions, for substituents n, $A^1$, $A^2$, $A^3$, $A^4$, $R^1$, $R^2$, $R^3$, $R^4$, $R^5$, $R^6$, Z ($Z^1$, $Z^2$, $Z^3$, $Z^4$, $Z^5$, $Z^6$), $R^7$, $R^8$, $R^9$, $R^{10}$ (including $R^a$, $R^b$, $R^c$, $R^d$, $R^e$, $R^f$, $R^g$, $R^h$), $R^{11}$, $R^{12}$, $R^{13}$, $R^{14}$, and $R^{15}$, with reference to the compounds of formula (I). For any one of these substituents, any of the definitions given below may be combined with any definition of any other substituent given below, or elsewhere in this document.

n is 1 or 2. In one embodiment of the invention, n is 1. In another embodiment of the invention, n is 2.

When n is 2, Z is linked to the rest of the molecule by the $C(R^5)(R^6)$ fragment least proximal to the $A^1$ to $A^4$ ring system.

In another embodiment of the invention, there is provided a compound of formula (I): wherein $A^1$ represents N or $CR^1$, wherein $R^1$ represents hydrogen, halogen, methyl, ethyl, difluoromethyl, trifluoromethyl, methoxy, ethoxy, or difluoromethoxy;

$A^2$ represents N or $CR^2$, wherein $R^2$ represents hydrogen, halogen, methyl, ethyl, difluoromethyl, trifluoromethyl, methoxy, ethoxy, or difluoromethoxy;

$A^3$ represents N or $CR^3$, wherein $R^3$ represents hydrogen or halogen;

$A^4$ represents N or $CR^4$, wherein $R^4$ represents hydrogen or halogen; and wherein no more than two of $A^1$ to $A^4$ are N;

$R^5$ and $R^6$ are independently selected from hydrogen, $C_{1-4}$alkyl, halogen, cyano, trifluoromethyl and difluoromethyl; or $R^5$ and $R^6$ together with the carbon atom to which they are attached form a cyclopropyl;

Z is selected from $Z^1$, $Z^2$, $Z^3$, $Z^4$, $Z^5$ or $Z^6$; wherein $Z^1$ represents a heterocycle linked to $C(R^5)(R^6)$ via a C—C bond, wherein the heterocycle moiety is a 5- or 6-membered non-aromatic ring which contains 1 nitrogen in the ring system and optionally comprises 0, 1, 2, or 3 additional ring members independently selected from the group consisting of O, S, N, $NR^7$, C(O), or $S(O)_2$, with the proviso that the heterocycle cannot contain 2 consecutive atoms selected from O and S;

$Z^2$ represents a heteroaryl linked to $C(R^5)(R^6)$ via a C—C bond, wherein the heteroaryl moiety is a 5- or 6-membered aromatic ring which contains 1 nitrogen atom in the ring system and optionally comprises 0, 1, 2, or 3 additional ring members independently selected from the group consisting of O, S, N, or $NR^7$;

$R^7$ is $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, or N,N-di$C_{1-4}$alkylaminocarbonyl;

wherein for $Z^1$ and $Z^2$, the heterocyclyl or heteroaryl moiety is optionally substituted by 1, 2 or 3 substituents, which may be the same or different, selected from $R^8$;

$R^8$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{1-4}$alkoxycarbonylamino;

$Z^3$ represents a heterocycle linked to $C(R^5)(R^6)$ via a C—N bond, wherein the heterocyclyl moiety is a 5- or 6-membered non-aromatic ring which contains 1 nitrogen in the ring system and optionally comprises 1, 2, or 3 additional ring members independently selected from the group consisting of O, S, N, or $NR^9$, with the proviso that the heterocycle cannot contain 2 consecutive atoms selected from O and S;

$Z^4$ represents a heteroaryl linked to $C(R^5)(R^6)$ via a C—N bond, wherein the heteroaryl moiety is a 5-membered aromatic ring which contains 1 to 4 nitrogen atoms in the ring system;

$R^9$ is $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, or N,N-di$C_{1-4}$alkylaminocarbonyl; and wherein for $Z^3$ and $Z^4$, the heterocyclyl or heteroaryl moiety is optionally substituted by 1, 2 or 3 substituents, which may be the same or different, selected from $R^{10}$;

$R^{10}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl, $C_{1-4}$alkoxycarbonylamino, $C_{1-4}$alkoxycarbonylamino$C_{1-4}$alkyl, phenylcarbonyloxy$C_{1-4}$alkyl phenylcarbonylamino$C_{1-4}$alkyl, $C_{1-4}$alkylcarbonyloxy, $C_{1-4}$alkylcarbonyloxy$C_{1-4}$alkyl, $(C_{1-4}$alkyl$)_3$Si—;

wherein for $Z^4$, any heteroaryl moieties are optionally substituted by 1 substituent selected from $R^{11}$ and are further optionally substituted by 1 or 2 substituents selected from $R^{10}$;

$R^{11}$ represents $C_{3-8}$cycloalkyl, $C_{3-8}$cycloalkyl$C_{1-2}$alkyl, phenyl, phenyl$C_{1-2}$alkyl, phenyloxy$C_{1-2}$alkyl, heteroaryl, heteroaryl$C_{1-2}$alkyl, heteroaryloxy$C_{1-2}$alkyl, wherein the heteroaryl moiety is a 5- or 6-membered aromatic ring which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1 or 2 heteroatoms individually selected from N, O and S, and wherein any of said cycloalkyl, phenyl, heteroaryl and heterocyclyl moieties are optionally substituted by 1, 2 or 3 substituents, which may be the same or different, selected from $R^{12}$;

$R^{12}$ represents hydrogen, cyano, fluoro, chloro, bromo, methyl, ethyl, methoxy, ethoxy, difluoromethyl, trifluoromethyl or difluoromethoxy;

$Z^5$ represents a heterobicyclyl linked to $C(R^5)(R^6)$ via a C—N bond, wherein the heterobicyclyl moiety is a 7- to 10-membered saturated, partially saturated or partially aromatic fused ring system which contains 1 nitrogen in the ring system and optionally comprises 0, 1, 2, or 3 additional ring members independently selected from the group consisting of O, S, N, or $NR^{13}$, C(O) or $S(O)_2$, with the proviso that the heterobicyclyl cannot contain 2 consecutive atoms selected from O and S;

$Z^6$ represents a heterdioaryl linked to $C(R^5)(R^6)$ via a C—N bond, wherein the heterdioaryl moiety is a 9-membered di-aromatic system which contains 1 to 4 nitrogen atom in the ring system;

$R^{13}$ is $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, or N,N-di$C_{1-4}$alkylaminocarbonyl;

wherein for $Z^5$ and $Z^6$, the heterobicyclyl or heterodiaryl moiety is optionally substituted by 1, 2 or 3 substituents, which may be the same or different, selected from $R^{14}$;

$R^{14}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{1-4}$alkoxycarbonylamino.

In other embodiments of the invention:

$A^1$ represents N or $CR^1$, wherein $R^1$ represents hydrogen, halogen, methyl, ethyl, difluoromethyl, trifluoromethyl, methoxy, ethoxy, or difluoromethoxy. Preferably, $A^1$ represents $CR^1$, wherein $R^1$ is hydrogen, halogen, methyl, ethyl, difluoromethyl, trifluoromethyl, methoxy, ethoxy or difluoromethoxy. More preferably, $R^1$ is hydrogen or halogen, and even more preferably, $R^1$ is hydrogen.

$A^2$ represents N or $CR^2$, wherein $R^2$ represents hydrogen, halogen, methyl, ethyl, difluoromethyl, trifluoromethyl, methoxy, ethoxy, or difluoromethoxy. Preferably, $A^2$ represents $CR^2$, wherein $R^2$ is hydrogen, halogen, methyl, ethyl, difluoromethyl, trifluoromethyl, methoxy, ethoxy, or difluoromethoxy. More preferably, $R^2$ is hydrogen or halogen, and even more preferably, $R^2$ is hydrogen.

$A^3$ represents N or $CR^3$, wherein $R^3$ represents hydrogen or halogen. Preferably, $A^3$ represents $CR^3$, wherein $R^3$ is hydrogen or halogen. More preferably, $R^3$ is hydrogen or fluoro, and even more preferably, $R^3$ is hydrogen.

$A^4$ represents N or $CR^4$, wherein $R^4$ represents hydrogen or halogen. Preferably, $A^4$ represents $CR^4$, wherein $R^4$ is hydrogen or halogen. More preferably, $R^4$ is hydrogen or fluoro, and even more preferably, $R^4$ is hydrogen.

In the compounds according to Formula (I), no more than two (ie, 0, 1 or 2) of $A^1$, $A^2$, $A^3$ and $A^4$ are N.

In some embodiments of the invention, $A^1$ is N or $CR^1$ wherein $R^1$ represents hydrogen, chloro, fluoro, methyl, methoxy or trifluoromethyl, and $A^2$, $A^3$ and $A^4$ are C—H. Preferably, $A^1$ is N and $A^2$, $A^3$ and $A^4$ are C—H; or $A^1$ is C—F and $A^2$, $A^3$ and $A^4$ are C—H; or $A^1$ is C—Cl and $A^2$, $A^3$ and $A^4$ are C—H; or $A^1$, $A^2$, $A^3$ and $A^4$ are C—H. More preferably, $A^1$, $A^2$, $A^3$ and $A^4$ are C—H. In other embodiments of the invention, $A^3$ is $CR^3$ and $R^3$ is halogen (eg, fluoro or chloro), and $A^1$, $A^2$ and $A^4$ are C—H.

In some embodiments of the invention, the 6-membered ring comprising $A^1$ to $A^4$ is a phenyl (where $A^1$, $A^2$, $A^3$ and $A^4$ are C—H), a pyridinyl (where $A^1$ is N and $A^2$, $A^3$ and $A^4$ are C—H, or $A^3$ is N and $A^1$, $A^2$ and $A^4$ are C—H), a fluorophenyl (where $A^1$ is C—F and $A^2$, $A^3$ and $A^4$ are C—H, or $A^3$ is C—F and $A^1$, $A^2$ and $A^4$ are C—H) or a difluorophenyl (eg, where $A^1$ and $A^2$ are C—F and $A^3$ and $A^4$ are C—H, or A and $A^3$ are C—F and $A^2$ and $A^4$ are C—H) group.

$R^5$ and $R^6$ are independently selected from hydrogen, $C_{1-4}$alkyl, halogen, cyano, trifluoromethyl and difluoromethyl, or $R^5$ and $R^6$ together with the carbon atom they share form a cyclopropyl. $R^5$ is hydrogen, $C_{1-4}$alkyl, halogen, cyano, trifluoromethyl and difluoromethyl, and preferably, hydrogen, $C_{1-4}$alkyl, halogen or cyano. $R^6$ is hydrogen, $C_{1-4}$alkyl, halogen, cyano, trifluoromethyl and difluoromethyl, and preferably, hydrogen, $C_{1-4}$alkyl, halogen or cyano. Preferably, $R^5$ is hydrogen and $R^6$ is $C_{1-4}$alkyl, preferably methyl or ethyl. More preferably, $R^5$ and $R^6$ are hydrogen, or $R^5$ is hydrogen and $R^6$ is methyl.

Z is selected from $Z^1$, $Z^2$, $Z^3$, $Z^4$, $Z^5$ or $Z^6$.

In some embodiments of the invention, Z is $Z^1$. In other embodiments of the invention, Z is $Z^2$. In other embodiments of the invention, Z is $Z^3$. In other embodiments of the invention, Z is $Z^4$. In other embodiments of the invention, Z is $Z^5$. In other embodiments of the invention, Z is $Z^6$. Preferably, Z is $Z^4$ or $Z^6$.

$Z^1$ represents a heterocyclyl linked to $C(R^5)(R^6)$ via a C—C bond, wherein the heterocyclyl moiety is a 5- or 6-membered non-aromatic ring which contains 1 nitrogen in the ring system and optionally comprises 1, 2, or 3 additional ring members independently selected from the group consisting of O, S, N, $NR^7$, C(O), or $S(O)_2$, with the proviso that the heterocycle cannot contain 2 contiguous atoms selected from O and S. $Z^1$ may be selected from pyrrolidinyl, piperidinyl, imidazolidinyl, pyrazolidinyl, piperazinyl, oxazolidinyl, isooxazolidinyl, 4,5-dihydrooxazolyl, morpholinyl, thiazolidinyl, thiazolinyl, thiomorpholinyl.

Preferably, $Z^1$ optionally comprises 1 additional ring member selected from O, S, N, $NR^7$, C(O), or $S(O)_2$, and more preferably, O or S. According to an embodiment of the invention, $Z^1$ is a heterocyclyl moiety comprising a 5- or 6-membered non-aromatic ring with 1 nitrogen in the ring system.

$Z^2$ represents a heteroaryl linked to $C(R^5)(R^6)$ via a C—C bond, wherein the heteroaryl moiety is a 5- or 6-membered aromatic ring which contains 1 nitrogen atom in the ring system and optionally comprises 1, 2, or 3 additional ring members independently selected from the group consisting of O, S, N, or $NR^7$. $Z^2$ may be selected from pyrrolyl, pyrazolyl, imidazolyl, triazolyl, tetrazolyl, oxazolyl, isoxazolyl, thiazolyl, isothiazolyl, oxadiazolyl, thiadiazolyl, pyridinyl, pyrazinyl, pyrimidinyl, pyridazinyl, triazinyl. Preferably, $Z^2$ optionally comprises 1 or 2 additional ring members selected from O, S, N, or $NR^7$. More preferably, $Z^2$ is pyridinyl, in particular, pyridin-2-yl, pyridin-3-yl or pyridin-4-yl.

According to an embodiment of the invention, $Z^2$ is a heteroaryl moiety which is a 5- or 6-membered aromatic ring with 1 nitrogen in the ring system.

For $Z^1$ and $Z^2$, the heterocyclyl or heteroaryl moiety is optionally substituted by 1, 2 or 3 substituents, which may be the same or different, selected from $R^8$. Preferably, for $Z^1$ and $Z^2$, the heterocyclyl or heteroaryl moiety is optionally substituted by 1 or 2 substituents, which may be the same or different, selected from $R^8$. More preferably, for $Z^1$ and $Z^2$, the heterocyclyl or heteroaryl moiety is optionally substituted by 1 substituent selected from $R^8$.

$R^7$ is hydrogen, $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, N,N-di$C_{1-4}$alkylaminocarbonyl, $C_{1-4}$alkylsulfonyl, N—$C_{1-2}$alkylaminosulfonyl, or N,N-di$C_{1-2}$alkylaminosulfonyl. Preferably, $R^7$ is hydrogen or methyl.

$R^8$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{1-4}$alkoxycarbonylamino. Preferably, $R^8$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy.

More preferably, $R^8$ represents cyano, chloro, fluoro, hydroxy, methyl, ethyl, difluoromethyl, trifluoroethyl, methoxy, ethoxy, trifluormethoxy.

$Z^3$ represents a heterocyclyl linked to $C(R^5)(R^6)$ via a C—N bond, wherein the heterocyclyl moiety is a 5- or 6-membered non-aromatic ring which contains 1 nitrogen in the ring system and optionally comprises 1, 2, or 3 additional ring members independently selected from the group consisting of O, S, N, $NR^9$ or $C(=N-O-C_{1-4}alkyl)$, with the proviso that the heterocycle cannot contain 2 contiguous atoms selected from O and S. Preferably, $Z^3$ optionally comprises 1 additional ring member selected from O, S, N, or $NR^9$. $Z^3$ may be selected from pyrrolidinyl, piperidinyl, imidazolidinyl, pyrazolidinyl, piperazinyl, oxazolidinyl, isooxazolidinyl, 4,5-dihydrooxazolyl, morpholinyl, thiazolidinyl, thiazolinyl, thiomorpholinyl.

According to an embodiment of the invention, $Z^3$ is a heterocycle moiety comprising a 5- or 6-membered non-aromatic ring with one nitrogen in the ring system.

$Z^4$ represents a heteroaryl linked to $C(R^5)(R^6)$ via a C—N bond, wherein the heteroaryl moiety is a 5-membered aromatic ring which contains 1 to 4 nitrogen atoms in the ring system. Preferably, $Z^4$ is pyrrolyl, pyrazolyl, imidazolyl, triazolyl, tetrazolyl.

In particular, $Z^4$ (optionally substituted according to the invention) may be selected from:

More preferably, $Z^4$ is pyrazol-1-yl or triazolyl. When $Z^4$ is triazolyl, it may be 1,2,3-triazol-1-yl, 1,2,3-triazol-2-yl, 1,2,4-triazol-4-yl or 1,2,4-triazol-1-yl, and most preferably, 1,2,4-triazol-1-yl or 1,2,3-triazol-1-yl.

$Z^4$ may be a heteroaryl moiety which is a 5-membered aromatic ring with a single nitrogen in the ring system. However, in some embodiments, $Z^4$ may further comprise 1 or 2 additional ring members selected from O, S and N.

For $Z^3$ and $Z^4$, the heterocyclyl or heteroaryl moiety is optionally substituted by 1, 2 or 3 substituents, which may be the same or different, selected from $R^{10}$, or for $Z^4$, the heteroaryl moiety is optionally substituted by 1 substituent selected from $R^{11}$ and further optionally substituted by 1 or 2 substituents, which may be the same or different, selected from $R^{10}$.

Preferably, for $Z^4$, the heteroaryl moiety is optionally substituted by 1 substituent or 2 substituents, which may be the same or different, selected from $R^{10}$, or the heteroaryl moiety is optionally substituted by 1 substituent selected from $R^{11}$ and further optionally substituted by 1 substituent selected from $R^{10}$. For $Z^4$, the heteroaryl moiety may optionally be substituted by 1 substituent selected from $R^{10}$, or the heteroaryl moiety may optionally be substituted by 1 substituent selected from $R^{11}$.

$R^9$ is hydrogen, $C_{1-4}alkyl$, $C_{1-4}alkoxy$, formyl, $C_{1-4}alkylcarbonyl$, $C_{1-4}alkoxycarbonyl$, $N-C_{1-4}alkylaminocarbonyl$, or $N,N-diC_{1-4}alkylaminocarbonyl$. Preferably, $R^9$ is hydrogen or methyl.

$R^{10}$ represents (i), (ii) or (iii), wherein:

(i) cyano, halogen, hydroxy, amino, $C_{1-4}alkyl$, $C_{2-4}alkenyl$, $C_{2-4}alkynyl$, $C_{1-4}haloalkyl$, $C_{2-4}haloalkenyl$, $C_{1-4}alkoxy$, $C_{1-4}alkoxyC_{1-4}alkyl$, $C_{1-4}haloalkoxy$, $C_{1-4}alkylsulfanyl$, $C_{1-4}alkylsulfinyl$, $C_{1-4}alkylsulfonyl$, $C_{3-4}alkenyloxy$, $C_{3-4}alkynyloxy$, $N-C_{1-4}alkylamino$, $N,N-diC_{1-4}alkylamino$, formyl, hydroxycarbonyl, $C_{1-4}alkylcarbonyl$, $C_{1-4}alkoxycarbonyl$, $C_{1-4}alkylcarbonylamino$, aminocarbonyl, $N-C_{1-4}alkylaminocarbonyl$, $N-C_{2-4}alkenylaminocarbonyl$, $N-C_{2-4}alkynylaminocarbonyl$, $N,N-diC_{1-4}alkylaminocarbonyl$, N-morpholinoaminocarbonyl, $N-C_{1-4}alkoxyaminocarbonyl$, $N-C_{1-4}alkyl-N-C_{1-4}alkoxyaminocarbonyl$, $C_{1-4}alkoxycarbonylamino$, $C_{1-4}alkoxycarbonylaminoC_{1-4}alkyl$, $N-C_{1-4}alkoxyC_{1-4}alkylaminocarbonyl$, phenylcarbonyloxyC$_{1-4}$alkyl, phenylcarbonylamino C$_{1-4}$alkyl, $C_{1-4}alkylcarbonyloxy$, $C_{1-4}haloalkylcarbonyloxy$, $C_{1-4}alkylcarbonyloxyC_{1-4}alkyl$, $C_{1-4}alkylcarbonylamino$ $C_{1-4}alkyl$, $(C_{1-4}alkyl)_3Si-$; or (ii) $-C(O)N(R^a)(R^b)$, wherein:

$R^a$ is hydrogen, $C_{1-4}alkyl$, $C_{1-4}haloalkyl$, $C_{1-4}cyanoalkyl$, hydroxyC$_{1-4}$alkyl, $C_{1-2}alkoxyC_{1-4}alkyl$, $C_{1-2}haloalkoxyC_{1-4}alkyl$, $C_{3-5}alkenyl$, $C_{3-5}alkynyl$, aminoC$_{1-4}$alkyl, $N-C_{1-4}alkylaminoC_{1-4}alkyl$, $N,N-diC_{1-4}alkylaminoC_{1-4}alkyl$, formyl, $C_{1-4}alkylcarbonyl$, $C_{3-4}cycloalkylcarbonyl$, $C_{1-4}haloalkylcarbonyl$, $C_{1-4}alkylcarbonylC_{1-4}alkyl$, $C_{1-4}alkoxycarbonyl$, $C_{1-4}alkylcarbonyloxyC_{1-4}alkyl$, $N-C_{1-4}alkylaminocarbonylC_{1-4}alkyl$, $N,N-diC_{1-4}alkylaminocarbonylC_{1-4}alkyl$, $C_{1-4}alkylsulfanylC_{1-4}alkyl$, $C_{1-4}alkylsulfonyl$, $C_{1-4}alkylsulfonylC_{1-4}alkyl$, $C_{1-4}alkylsulfonylaminoC_{1-4}alkyl$, $C_{1-4}alkoxycarbonylaminoC_{1-4}alkyl$, $C_{1-4}alkylcarbonylaminoC_{1-4}alkyl$, $C_{1-4}alkoxycarbonylaminoC_{1-4}alkyl$, $C_{1-4}haloalkylcarbonylaminoC_{1-4}alkyl$, and $R^b$ is hydrogen, hydroxyl, $C_{1-4}alkyl$, $C_{1-4}haloalkyl$, $C_{1-4}cyanoalkyl$, hydroxyC$_{1-4}$alkyl, $C_{1-2}alkoxyC_{1-4}alkyl$, $C_{3-4}alkenyl$, $C_{3-4}alkynyl$, $C_{3-4}cycloalkyl$, $C_{3-4}cycloalkylC_{1-2}alkyl$, $C_{1-4}alkoxy$, $C_{3-4}alkenyloxy$, $C_{3-4}haloalkenyloxy$, $C_{3-4}alkynyloxy$; or $R^a$ and $R^b$ together with the nitrogen atom to which they are bonded, form a 4-, 5- or 6-membered cycle optionally containing an additional heteroatom or group selected from O, S, $S(O)_2$, C(O) and $NR^c$, wherein $R^c$ is hydrogen, methyl, methoxy, formyl or acyl; or (iii) $-C(O)O-R^d$, wherein:

$R^d$ is hydrogen, $C_{1-4}alkyl$, $C_{1-4}haloalkyl$, $C_{1-4}cyanoalkyl$, hydroxyC$_{1-4}$alkyl, $C_{1-2}alkoxyC_{1-4}alkyl$, $C_{1-2}alkoxyC_{1-2}alkoxyC_{1-4}alkyl$, $C_{1-2}haloalkoxyC_{1-4}alkyl$, $C_{3-5}alkenyl$, $C_{3-4}haloalkenyl$, $C_{3-4}alkenyloxyC_{1-4}alkyl$, $C_{3-5}alkynyl$, $C_{3-4}alkynyloxyC_{1-4}alkyl$, $N-C_{1-3}alkylaminoC_{1-4}alkyl$, $N,N-di-C_{1-3}alkylaminoC_{1-4}alkyl$, $C_{1-4}alkoxycarbonylaminoC_{1-4}alkyl$ or $C_{1-4}alkylcarbonylaminoC_{1-4}alkyl$.

Preferably, $R^{10}$ (particularly, when Z is $Z^4$) represents cyano, halogen, hydroxy, amino, $C_{1-4}alkyl$, $C_{1-4}haloalkyl$, $C_{1-4}alkoxy$, $C_{1-4}alkoxyC_{1-4}alkyl$, $C_{1-4}alkylsulfanyl$, $C_{1-4}haloalkylsulfanyl$, $N,N-diC_{1-4}alkylamino$, formyl, hydroxycarbonyl, $C_{1-4}alkylcarbonyl$, $C_{1-4}alkoxycarbonyl$, aminocarbonyl, $N-C_{1-4}alkylaminocarbonyl$, $N-C_{2-4}$ alkynylaminocarbonyl, $N,N-diC_{1-4}alkylaminocarbonyl$, N-morpholinoaminocarbonyl, $N-C_{1-4}alkoxyaminocarbonyl$, $N-C_{1-4}alkyl-N-C_{1-4}alkoxyaminocarbonyl$, $C_{1-4}alkoxycarbonylaminoC_{1-4}alkyl$, $N-C_{1-4}alkoxyC_{1-4}alkylaminocarbonyl$, phenylcarbonylaminoC$_{1-4}$alkyl, $C_{1-4}alkylcarbonyloxyC_{1-4}alkyl$, $C_{1-4}alkylcarbonylaminoC_{1-4}alkyl$, $(C_{1-4}alkyl)_3Si-$.

More preferably, $R^{10}$ (particularly, when Z is $Z^4$) represents cyano, fluoro, chloro, bromo, iodo, hydroxy, amino, methyl, ethyl, n-propyl, iso-propyl, n-butyl, s-butyl, t-butyl, difluoromethyl, trifluoromethyl, methoxy, ethoxy, ethoxymethyl, methoxyethyl, methylsulfanyl, ethylsulfanyl, n-propylsulfanyl, difluoromethylsulfanyl, trifluoromethylsulfanyl, dimethylamino, formyl, hydroxycarbonyl, methylcarbonyl, methoxycarbonyl, ethoxycarbonyl, n-propoxycarbonyl, i-propoxycarbonyl, t-butoxycarbonyl, aminocarbonyl, methylaminocarbonyl, ethylaminocarbonyl, propynylaminocarbonyl (including propargylaminocarbonyl), morpholinoaminocarbonyl, N-methoxyaminocarbonyl, N-methyl-N-methoxyaminocarbonyl, N,N-dimethylaminocarbonyl, N,N-diethylaminocarbonyl, t-butoxycarbonylaminomethyl, methoxyethylaminocarbonyl, phenylcarbonylamino(dimethyl)methyl, methylcarbonyloxymethyl, methylcarbonylaminoethyl, trimethylsilyl.

In some preferred embodiments of the invention, $R^{10}$ is selected from hydroxycarbonyl, methoxycarbonyl, ethoxycarbonyl, n-propoxycarbonyl, i-propoxycarbonyl, t-butoxycarbonyl, aminocarbonyl, methylaminocarbonyl, ethylaminocarbonyl, propargylaminocarbonyl, N-morpholinoaminocarbonyl, N,N-dimethylaminocarbonyl, N,N-diethylaminocarbonyl, N-methyl-N-methoxyaminocarbonyl or N-methoxyaminocarbonyl. In some further preferred embodiments, $R^{10}$ is selected from hydroxycarbonyl, methoxycarbonyl, ethoxycarbonyl, i-propoxycarbonyl, t-butoxycarbonyl, methylaminocarbonyl and ethylaminocarbonyl.

In other embodiments of the invention, $R^{10}$ is cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkyl, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl, $C_{1-4}$alkoxycarbonylamino, $C_{1-4}$alkoxycarbonylamino$C_{1-4}$alkyl, phenylcarbonyloxy$C_{1-4}$alkyl phenylcarbonylamino$C_{1-4}$alkyl, $C_{1-4}$alkylcarbonyloxy, $C_{1-4}$alkylcarbonyloxy$C_{1-4}$alkyl, or $(C_{1-4}$alkyl$)_3$Si—.

$R^{11}$ represents (i), (ii), (iii) or (iv), wherein:
(i) $C_{3-8}$cycloalkyl, $C_3$-acycloalkyl$C_{1-2}$alkyl, N—$C_{3-8}$cycloalkylaminocarbonyl, N—$C_{3-8}$cycloalkyl$C_{1-2}$alkylaminocarbonyl, phenyl, phenyl$C_{1-2}$alkyl, phenoxy$C_{1-2}$alkyl, phenyl$C_{1-2}$alkylsulfanyl, heteroaryl, heteroaryl$C_{1-2}$alkyl, heteroaryloxy$C_{1-2}$alkyl, N-heteroarylaminocarbonyl, heterocyclylcarbonyl, wherein the heteroaryl moiety is a 5- or 6-membered aromatic ring which comprises 1, 2, 3 or 4 heteroatoms individually selected from N, O and S, heterocyclyl, heterocyclyl$C_{1-6}$alkyl wherein the heterocyclyl moiety is a 4- to 6-membered non-aromatic ring which comprises 1 or 2 heteroatoms individually selected from N, O and S, benzodioxolyl, and wherein any of said cycloalkyl, phenyl, heteroaryl, heterocyclyl and benzodioxolyl moieties are optionally substituted by 1, 2 or 3 substituents, which may be the same or different, selected from $R^{12}$; or
(ii) —C(O)N($R^e$)($R^f$), wherein:
$R^e$ is $C_{3-5}$cycloalkyl, $C_{3-5}$cycloalkyl$C_{1-2}$alkyl, phenyl, phenyl$C_{1-2}$alkyl, heterocyclyl, heterocyclyl$C_{1-2}$alkyl, wherein the heterocyclyl moiety is a 4- to 6-membered non-aromatic ring which comprises 1, 2, or 3 ring members independently selected from the group consisting of O, S, N or $S(O)_2$, with the proviso that the heterocycle cannot contain 2 contiguous atoms selected from O and S, heteroaryl, heteroaryl$C_{1-2}$alkyl, wherein the heteroaryl moiety is a 5- or 6-membered aromatic ring which comprises 1, 2, 3 or 4 heteroatoms individually selected from N, O and S,
and wherein the cycloalkyl, phenyl, heterocyclyl or heteroaryl moiety is optionally substituted by 1 or 2 substituents, which may be the same or different, selected from hydroxyl, amino, formyl, acyl, cyano, halogen, methyl, difluoromethyl, trifluoromethyl, methoxy, ethoxy, or difluoromethoxy, or the cycloalkyl or heterocyclyl moiety is optionally substituted by 1 or 2 groups which are oxo (=O), and $R^f$ is hydrogen, $C_{1-4}$alkyl, $C_{1-4}$alkoxy $C_{1-4}$haloalkyl, $C_{3-4}$alkenyl, $C_{3-4}$alkynyl, $C_{3-4}$cycloalkyl, or $C_{3-4}$cycloalkyl$C_{1-2}$alkyl; or
(iii) —C(O)O—$R^g$, wherein:
$R^g$ is $C_{3-5}$cycloalkyl, $C_{3-5}$cycloalkyl$C_{1-2}$alkyl, phenyl, phenyl$C_{1-2}$alkyl, heterocyclyl, heterocyclyl$C_{1-2}$alkyl, wherein the heterocyclyl moiety is a 4- to 6-membered non-aromatic ring which comprises 1, 2, or 3 ring members independently selected from the group consisting of O, S, N or $S(O)_2$, with the proviso that the heterocycle cannot contain 2 contiguous atoms selected from O and S, heteroaryl, heteroaryl$C_{1-2}$alkyl, wherein the heteroaryl moiety is a 5- or 6-membered aromatic ring which comprises 1, 2, 3 or 4 heteroatoms individually selected from N, O and S,
and wherein the cycloalkyl, phenyl, heterocyclyl or heteroaryl moiety is optionally substituted by 1 or 2 substituents, which may be the same or different, selected from hydroxyl, formyl, acyl, cyano, halogen, methyl, difluoromethyl, trifluoromethyl, methoxy, ethoxy, or difluoromethoxy, or the cycloalkyl or heterocyclyl moiety is optionally substituted by 1 or 2 groups which are oxo (=O); or
(iv) $(C_{1-4}$alkyl$)$-O—N=C($R^h$)—, $(C_{1-4}$haloalkyl$)$-O—N=C($R^h$)—, $(C_{2-4}$alkenyl$)$-O—N=C($R^h$), $(C_{2-4}$alkynyl$)$-O—N=C($R^h$)—, benzyl-O—N=C($R^h$)—, wherein $R^h$ is hydrogen or methyl;

Preferably, $R^{11}$ (particularly, when Z is $Z^4$) represents cyclopropyl, cyclobutyl, cyclopentyl, cyclohexyl, phenyl, cyclopropylaminocarbonyl, cyclopropylmethylaminocarbonyl, phenoxymethyl, benzylsulfanyl, pyrazolyl, imidazolyl, thienyl, pyridinyl, pyridinyloxymethyl, benzodioxolyl.

Preferably, $R^{11}$ is $C_{3-8}$cycloalkyl, $C_{3-8}$cycloalkyl$C_{1-2}$alkyl, phenyl, phenyl$C_{1-2}$alkyl, phenyloxy$C_{1-2}$alkyl, heteroaryl, heteroaryl$C_{1-2}$alkyl, heteroaryloxy$C_{1-2}$alkyl, heterocyclyl, or heterocyclyl$C_{1-6}$alkyl.

$R^{12}$ represents cyano, fluoro, chloro, bromo, methyl, ethyl, formyl, methoxy, ethoxy, difluoromethyl, trifluoromethyl, difluoromethoxy or ethoxycarbonyl. Preferably, $R^{12}$ is cyano, fluoro, chloro, bromo, methyl, ethyl, methoxy, ethoxy, difluoromethyl, trifluoromethyl or difluoromethoxy.

$Z^5$ represents a heterobicyclyl linked to $C(R^5)(R^6)$ via a C—N bond, wherein the heterobicyclyl moiety is a 7- to 10-membered saturated, partially saturated or partially aromatic fused ring system which contains 1 nitrogen in the ring system and optionally comprises 1, 2, or 3 additional ring members independently selected from the group consisting of O, S, N, $NR^{13}$, C(O) or $S(O)_2$, with the proviso that the heterobicyclyl cannot contain 2 contiguous atoms selected from O and S. $Z^5$ may be selected from cyclopentapyrrolyl, tetrahydropurinyl.

$Z^6$ represents a heterdioaryl linked to $C(R^5)(R^6)$ via a C—N bond, wherein the heterdioaryl moiety is a 9-membered di-aromatic system which contains 1 to 4 nitrogen atoms in the ring system. Preferably, $Z^6$ represents a heterdioaryl which contains 1, 2 or 3 nitrogen atoms in the ring system. $Z^6$ may be selected from indolyl, benzimidazolyl, benzotriazolyl (including benzotriazol-1-yl and benzotriazol-2-yl), indazolyl, pyrrolopyridinyl.

For $Z^5$ and $Z^6$, the heterobicyclyl or heterodiaryl moiety is optionally substituted by 1, 2, 3 or 4 substituents, which may be the same or different, selected from $R^{14}$, or for $Z^5$ and $Z^6$, the heterobicyclyl or heterodiaryl moiety is optionally substituted by 1 substituent selected from $R^{15}$ and further optionally substituted by 1 or 2 substituents, which may be the same or different, selected from $R^{14}$. For $Z^6$, the heterodiaryl moiety may be optionally substituted by 1 or 2 substituents, which may be the same or different, selected from $R^{14}$, or for $Z^6$, the heterodiaryl moiety may optionally be substituted by 1 substituent selected from $R^{15}$ and further optionally substituted by 1 substituent selected from $R^{14}$.

$R^{13}$ is hydrogen, $C_{1-4}$alkyl, $C_{1-4}$alkoxy, formyl, $C_{1-4}$alkylcarbonyl, $C_{1-4}$alkoxycarbonyl, N—$C_{1-4}$alkylaminocarbonyl, or N,N-di$C_{1-4}$alkylaminocarbonyl. Preferably, $R^{13}$ is hydrogen or methyl.

$R^{14}$ represents cyano, halogen, hydroxy, formyl, $C_{1-4}$alkyl, $C_{2-4}$alkenyl, $C_{2-4}$alkynyl, $C_{1-4}$haloalkyl, cyano$C_{1-4}$ alkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{1-4}$alkoxycarbonylamino, and additionally oxo (=O) for $Z^5$. Preferably, $R^{14}$ represents fluoro, chloro, bromo, methyl, ethyl, formyl, difluoromethyl, trifluoromethyl, cyanomethyl, methoxy, ethoxy, methylcarbonyl, methoxycarbonyl, ethoxycarbonyl.

Preferably, $R^{14}$ is cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{1-4}$alkoxycarbonylamino.

$R^{15}$ is pyridinyl, benzodioxolyloxy, phenoxy or phenylsulfanyl, wherein phenoxy and phenylsulfanyl are optionally substituted by 1, 2 or 3 substituents, which may be the same or different, selected from chloro, fluoro, bromo, methyl, ethyl, methoxy and ethoxy.

Preferably, the compound according to Formula (I) is selected from a compound 1.1 to 1.312 listed in Table T1 (below).

Preferably, in a compound according to formula (I) of the invention:

n is 1;

$A^1$ is N or $CR^1$ wherein $R^1$ represents hydrogen, chloro, fluoro, methyl, methoxy or trifluoromethyl;

$A^2$, $A^3$ and $A^4$ are C—H;

$R^5$ and $R^6$ are hydrogen, or $R^5$ is hydrogen and $R^6$ is methyl;

Z is $Z^4$ selected from pyrrolyl, pyrazolyl, imidazolyl, triazolyl, tetrazolyl and is optionally substituted by 1, 2 or 3 substituents, which may be the same or different, selected from $R^{10}$, or is optionally substituted by 1 substituent selected from $R^{11}$ and further optionally substituted by 1 or 2 substituents selected from $R^{10}$;

$R^{10}$ represents cyano, fluoro, chloro, bromo, iodo, hydroxy, amino, methyl, ethyl, n-propyl, iso-propyl, n-butyl, s-butyl, t-butyl, difluoromethyl, trifluoromethyl, methoxy, ethoxy, ethoxymethyl, methoxyethyl, methylsulfanyl, ethylsulfanyl, n-propylsulfanyl, difluoromethylsulfanyl, trifluoromethylsulfanyl, formyl, hydroxycarbonyl, methylcarbonyl, methoxycarbonyl, ethoxycarbonyl, i-propoxycarbonyl, t-butoxycarbonyl, methylaminocarbonyl, ethylaminocarbonyl, propylaminocarbonyl, dimethylaminocarbonyl, t-butoxycarbonylaminomethyl, methoxyethylaminocarbonyl, phenylcarbonylamino(dimethyl)methyl, methylcarbonyloxymethyl, methylcarbonylaminoethyl, trimethylsilyl;

$R^{11}$ is cyclopropyl, cyclobutyl, cyclopentyl, cyclohexyl, phenyl, cyclopropylaminocarbonyl, cyclopropylmethylaminocarbonyl, phenoxymethyl, benzylsulfanyl, imidazolyl, thienyl, pyridinyl, pyridinyloxymethyl, benzodioxolyl, wherein any of said cycloalkyl, phenyl, heteroaryl and benzodioxolyl moieties are optionally substituted by 1, 2 or 3 substituents, which may be the same or different, selected from $R^{12}$; and $R^{12}$ is cyano, fluoro, chloro, bromo, methyl, ethyl, formyl, methoxy, ethoxy, difluoromethyl, trifluoromethyl or difluoromethoxy.

More preferably, n is 1;

$A^1$ is N and $A^2$, $A^3$ and $A^4$ are C—H; or $A^1$ is C—F and $A^2$, $A^3$ and $A^4$ are C—H; or $A^1$ is C—Cl and $A^2$, $A^3$ and $A^4$ are C—H; or $A^1$, $A^2$, $A^3$ and $A^4$ are C—H;

$R^5$ and $R^6$ are hydrogen;

Z is $Z^4$ selected from $Z^4$ is pyrazol-1-yl or triazolyl, and is optionally substituted by 1 or 2 substituents, which may be the same or different, selected from $R^{10}$, or is optionally substituted by 1 substituent selected from $R^{11}$ and further optionally substituted by 1 substituent selected from $R^{10}$;

$R^{10}$ represents cyano, fluoro, chloro, bromo, iodo, hydroxy, amino, methyl, ethyl, n-propyl, iso-propyl, n-butyl, s-butyl, t-butyl, difluoromethyl, trifluoromethyl, methoxy, ethoxy, ethoxymethyl, methoxyethyl, methylsulfanyl, ethylsulfanyl, n-propylsulfanyl, difluoromethylsulfanyl, trifluoromethylsulfanyl, formyl, hydroxycarbonyl, methylcarbonyl, methoxycarbonyl, ethoxycarbonyl, i-propoxycarbonyl, t-butoxycarbonyl, methylaminocarbonyl, ethylaminocarbonyl, propylaminocarbonyl, dimethylaminocarbonyl, t-butoxycarbonylaminomethyl, methoxyethylaminocarbonyl, phenylcarbonylamino(dimethyl)methyl, methylcarbonyloxymethyl, methylcarbonylaminoethyl, trimethylsilyl;

$R^{11}$ is cyclopropyl, cyclobutyl, cyclopentyl, cyclohexyl, phenyl, cyclopropylaminocarbonyl, cyclopropylmethylaminocarbonyl, phenoxymethyl, benzylsulfanyl, imidazolyl, thienyl, pyridinyl, pyridinyloxymethyl, benzodioxolyl, wherein any of said cycloalkyl, phenyl, heteroaryl and benzodioxolyl moieties are optionally substituted by 1, 2 or 3 substituents, which may be the same or different, selected from $R^{12}$; and $R^{12}$ is cyano, fluoro, chloro, bromo, methyl, ethyl, formyl, methoxy, ethoxy, difluoromethyl, trifluoromethyl or difluoromethoxy.

Even more preferably, n is 1;

$A^1$, $A^2$, $A^3$ and $A^4$ are C—H;

$R^5$ and $R^6$ are hydrogen;

Z is $Z^4$ selected from pyrazol-1-yl, 1,2,3-triazol-1-yl or 1,2,4-triazol-1-yl, wherein pyrazol-1-yl is optionally substituted by 1 substituent selected from $R^{10}$ or $R^{11}$, wherein $R^{10}$ is hydroxycarbonyl, methoxycarbonyl, ethoxycarbonyl, i-propoxycarbonyl, t-butoxycarbonyl, methylaminocarbonyl or ethylaminocarbonyl and $R^{11}$ is cyclopropylaminocarbonyl, cyclobutylaminocarbonyl, cyclopentylaminocarbonyl or cyclohexylaminocarbonyl, and 1,2,3-triazol-1-yl or 1,2,4-triazol-1-yl is optionally substituted by 1 substituent selected from $R^{10}$ or $R^{11}$, wherein $R^{10}$ is cyano, ethynyl, fluoro, chloro, methyl, ethyl, trifluoromethyl, methoxy, ethoxycarbonyl or ethoxymethyl, and $R^{11}$ is cyclopropyl.

Preferably, in a compound according to formula (I) of the invention:

n is 1;

$A^1$ is N or $CR^1$ wherein $R^1$ represents hydrogen, chloro, fluoro, methyl, methoxy or trifluoromethyl;

$A^2$, $A^3$ and $A^4$ are C—H;

$R^5$ and $R^6$ are hydrogen, or $R^5$ is hydrogen and $R^6$ is methyl;

Z is $Z^6$ selected from indolyl, indazolyl, benzimidazolyl, pyrrolopyridinyl or triazolopyridinyl and is optionally substituted by 1, 2 or 3 substituents, which may be the same or different, selected from $R^{14}$, or is optionally substituted by 1 substituent selected from $R^{15}$ and further optionally substituted by 1 or 2 substituents selected from $R^{14}$;

$R^{14}$ represents fluoro, chloro, bromo, methyl, ethyl, formyl, difluoromethyl, trifluoromethyl, cyanomethyl, methoxy, ethoxy, methylcarbonyl, methoxycarbonyl, ethoxycarbonyl; and $R^{15}$ is pyridinyl, benzodioxolyloxy, phenoxy or phenylsulfanyl, wherein phenoxy and phenylsulfanyl are optionally substituted by 1, 2 or 3 substituents, which may be the same or different, selected from chloro, fluoro, bromo, methyl, ethyl, methoxy and ethoxy.

More preferably, n is 1;

$A^1$, $A^2$, $A^3$ and $A^4$ are C—H;

$R^5$ and $R^6$ are hydrogen;

Z is $Z^6$ selected from indolyl, indazolyl, benzimidazolyl, pyrrolopyridinyl or triazolopyridinyl and is optionally substituted by 1 or 2 substituents, which may be the same or different, selected from $R^{14}$, or is optionally substituted by 1 substituent selected from $R^{15}$ and further optionally substituted by 1 substituent selected from $R^{14}$;

$R^{14}$ represents fluoro, chloro, bromo, methyl, ethyl, formyl, difluoromethyl, trifluoromethyl, cyanomethyl, methoxy, ethoxy, methylcarbonyl, methoxycarbonyl, ethoxycarbonyl; and $R^{15}$ is pyridinyl, benzodioxolyloxy, phenoxy or phenylsulfanyl, wherein phenoxy and phenylsulfanyl are optionally substituted by 1, 2 or 3 substituents, which may be the same or different, selected from chloro, fluoro, bromo, methyl, ethyl, methoxy and ethoxy.

The compounds of the present invention may be enantiomers of the compound of Formula (I) (when n=1) as represented by a Formula (Ia) or a Formula (Ib), wherein $R^5$ and $R^6$ are different substituents.

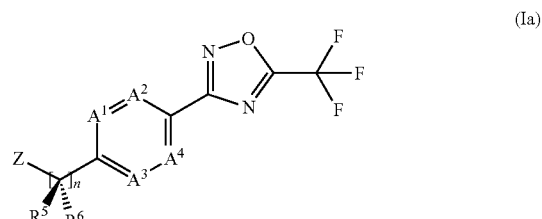

(Ia)

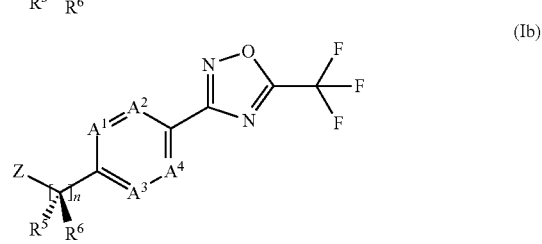

(Ib)

Likewise, the compounds of the present invention may be enantiomers (when n=2) when at one of the two carbon positions bound to $R^5$ and $R^6$, $R^5$ and $R^6$ are different substituents and at the other carbon position, $R^5$ and $R^6$ are the same. Alternatively, the compounds of Formula (I) may be diastereomers (when n=2) when at each of the two carbon positions bound to $R^5$ and $R^6$, $R^5$ and $R^6$ are different.

It is understood that when in aqueous media, the compounds of formula (I) according to the invention may be present in a reversible equilibrium with the corresponding covalently hydrated forms (ie, the compounds of formula (I-I) and formula (I-II) as shown below) at the $CF_3$-oxadiazole motif. This dynamic equilibrium may be important for the biological activity of the compounds of Formula (I). The designations of n, $A^1$, $A^2$, $A^3$, $A^4$, $R^1$, $R^2$, $R^3$, $R^4$, $R^5$, $R^6$, Z ($Z^1$, $Z^2$, $Z^3$, $Z^4$, $Z^5$, $Z^6$), $R^7$, $R^8$, $R^9$, $R^{10}$ (including $R^a$, $R^b$, $R^c$, $R^d$), $R^{11}$ (including $R^e$, $R^f$, $R^g$, $R^h$), $R^{12}$, $R^{13}$, $R^{14}$, and $R^{15}$ with reference to the compounds of formula (I) of the present invention apply generally to the compounds of Formula (I-I) and Formula (I-I), as well as to the specific disclosures of combinations of n, $A^1$, $A^2$, $A^3$, $A^4$, $R^1$, $R^2$, $R^3$, $R^4$, $R^5$, $R^6$, Z ($Z^1$, $Z^2$, $Z^3$, $Z^4$, $Z^5$, $Z^6$), $R^7$, $R^8$, $R^9$, $R^{10}$ (including $R^a$, $R^b$, $R^c$, $R^d$), $R^{11}$ (including $R^e$, $R^f$, $R^g$, $R^h$), $R^{12}$, $R^{13}$, $R^{14}$, and $R^{15}$ as represented in Tables 1.1 to 1.12 (below) or the compounds 1.1 to 1.312 according to the invention listed in Table T1 (below).

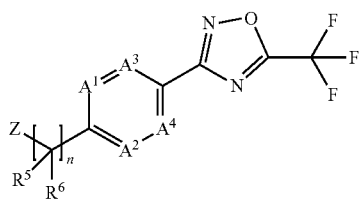

(I)

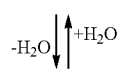

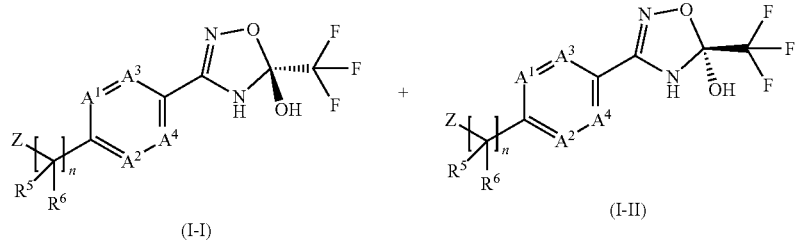

(I-I)   +   (I-II)

Compounds of the present invention can be made as shown in the following schemes 1 to 10, in which, unless otherwise stated, the definition of each variable is as defined above for a compound of formula (I).

Compounds of formula (I) can be prepared from compounds of formula (II), wherein X is a halogen, preferably Cl, Br or I, via treatment with compounds of formula (III), in the presence of a base (e.g. K₂CO₃, Cs₂CO₃, or NaH) in a suitable solvent (e.g. dimethylformamide or tetrahydrofuran) at a temperature between 25° C. and 110° C. In some cases, a better reaction performance may be gained from the use of a catalyst (eg, NaI or 4-dimethylaminopyridine) and with microwave irradiation. For related examples, see: WO 2013/132253 and Garcia, M. et al *Org. Biomol. Chem.* (2004), 11, 1633. This reaction is shown in Scheme 1.

Scheme 1

(II) + Z—H (III) → (I)

Additionally, compounds of formula (I), wherein preferably n is 1, can be prepared from compounds of formula (IV) by treatment with trifluoroacetic anhydride in the presence of a base (eg, pyridine or 4-dimethylaminopyridine) in a suitable solvent, such as tetrahydrofuran or ethanol, at a temperature between 25° C. and 75° C. For related examples, see WO 2003/028729 and WO 2010/045251. This reaction is shown in Scheme 2.

Scheme 2

(IV) → (I)

Compounds of formula (IV) can be prepared from compounds of formula (V) by treatment with a hydroxylamine hydrochloride salt in the presence of a base, such as triethylamine, in a suitable solvent, such as methanol, at a temperature between 0° C. and 100° C. For related examples, see Kitamura, S. et al *Chem. Pharm. Bull.* (2001), 49, 268 and WO 2013/066838. This reaction is shown in Scheme 3.

Scheme 3

(V) → (IV)

Compounds of formula (V) can be prepared from compounds of formula (VI), wherein Y is Br or I, via metal-promoted reaction with a suitable cyanide reagent, such as Pd(0)/Zn(CN)₂ or CuCN, in a suitable solvent (eg, dimethylformamide or N-methylpyrrolidone) at elevated temperature between 100° C. and 120° C. For related examples, see US 2007/0155739 and WO 2009/022746. This reaction is shown in Scheme 4.

Scheme 4

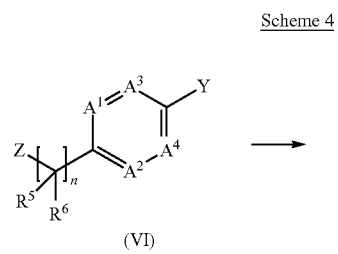

(VI)    (V)

Compounds of formula (VI), wherein preferably n is 1, can be prepared from compounds of formula (VII), wherein X is a halogen, preferably Cl, Br or I, via treatment with compounds of formula (III), in the presence of a base (e.g. K₂CO₃, Cs₂CO₃, or NaH) in a suitable solvent (e.g. dimethylformamide or tetrahydrofuran) at a temperature between 25° C. and 110° C. In some cases, a better reaction performance may be gained from the use of a catalyst (eg, NaI or 4-dimethylaminopyridine) and with microwave irradiation. For related examples, see: WO 2013/132253 and Garcia, M. et al *Org. Biomol. Chem.* (2004), 11, 1633. This reaction is shown in Scheme 5.

Scheme 5

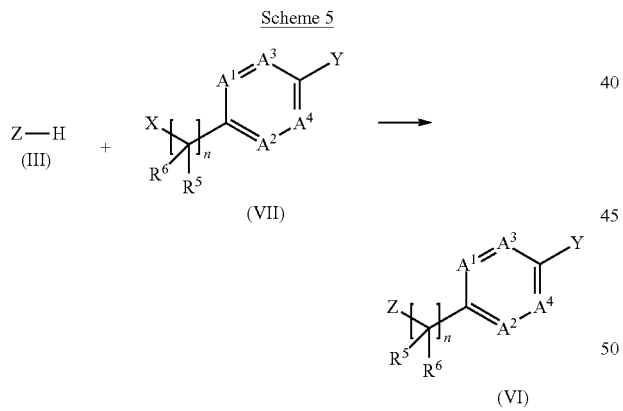

(VI)

Compounds of formula (II), wherein n is 1 and X is Cl or Br, can be prepared from compounds of formula (VIII) by treatment with a halogen source (eg, N-bromosuccinimide (NBS) or N-chlorosuccinimide (NCS)) and a radical initiator (eg, (PhCO₂)₂ or azobisisobutyronitrile (AIBN)) in a suitable solvent, such as tetrachloromethane, at temperatures between 55° and 100° C. in the presence of ultraviolet light. For related examples, see Liu, S. et al *Synthesis* (2001), 14, 2078 and Kompella, A. et al *Org. Proc. Res. Dev.* (2012), 16, 1794. This reaction is shown in Scheme 6.

Scheme 6

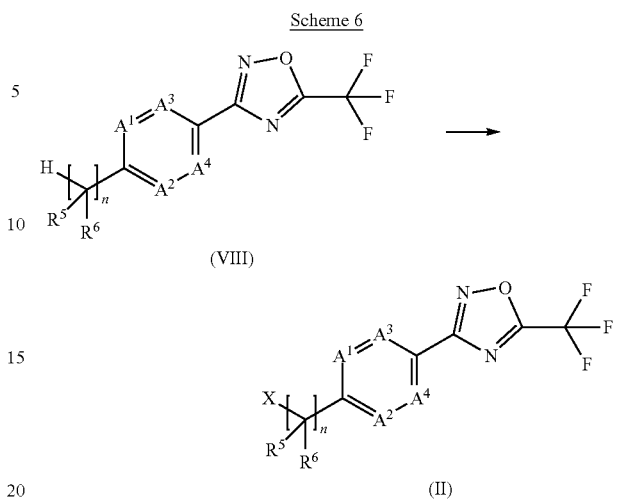

(VIII)

(II)

Alternatively, compounds of formula (II) can be prepared from compounds of formula (IX) by treatment with trifluoroacetic anhydride in the presence of a base (eg, pyridine or 4-dimethylaminopyridine) in a suitable solvent, such as tetrahydrofuran or ethanol, at a temperature between 25° C. and 75° C. For related examples, see WO 2003/028729 and WO 2010/045251. This reaction is shown in Scheme 7.

Scheme 7

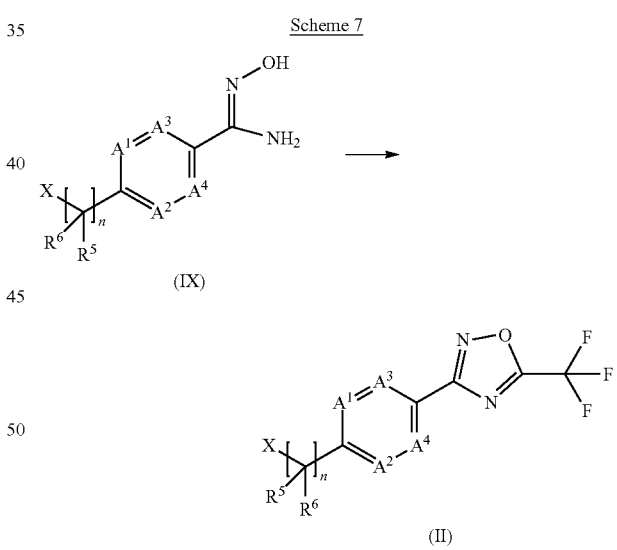

(IX)

(II)

Compounds of formula (IX) can be prepared from compounds of formula (X) by treatment with a hydroxylamine hydrochloride salt in the presence of a base, such as triethylamine, in a suitable solvent, such as methanol, at a temperature between 0° C. and 100° C. For related examples, see Kitamura, S. et al *Chem. Pharm. Bull.* (2001), 49, 268 and WO 2013/066838. This reaction is shown in Scheme 8.

Scheme 8

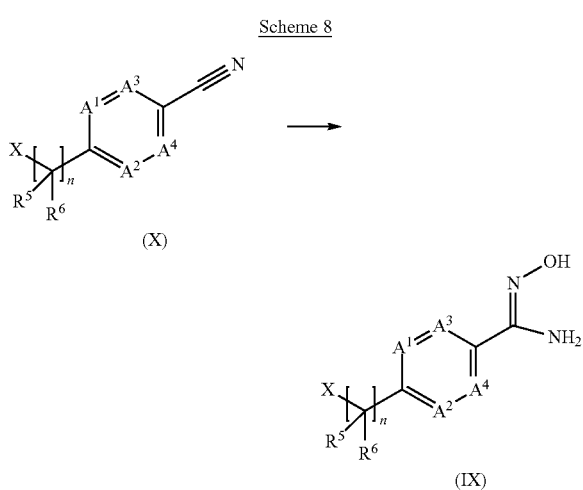

Compounds of formula (VII), wherein Y is Br, I or CN and X is Cl, Br or I, are either commercially available or can be prepared from compounds of formula (XI), by treatment with a halogen source, (eg, N-bromosuccinimide (NBS) or N-chlorosuccinimide (NCS)) and a radical initiator, such as (PhCO$_2$)$_2$ or azobisisobutyronitrile (AIBN), in the presence of ultraviolet light, in a suitable solvent, such as tetrachloromethane, at temperatures between 55° C. and 100° C. For related examples, see Liu, S. et al *Synthesis* (2001), 14, 2078 and Kompella, A. et al *Org. Proc. Res. Dev.* (2012), 16, 1794. This reaction is shown in Scheme 9.

Scheme 9

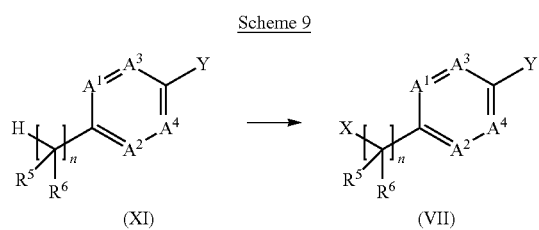

Alternatively, compounds of formula (VII), wherein n is 1 and X is Cl, Br, I or OSO$_2$Me and Y is Br, I or CN, are either commercially available or can be prepared from compounds of formula (XII), by treatment with a halogen source (eg, CCl$_3$Br, CCl$_4$ or I$_2$) in the presence of triphenylphosphine, or with methanesulfonyl chloride (ClSO$_2$Me), in a suitable solvent, (eg, dichloromethane) at a temperature between 0° C. and 100° C. For related examples, see Liu, H. et al *Bioorg. Med. Chem.* (2008), 16, 10013, WO 2014/020350 and Kompella, A. et al *Bioorg. Med. Chem. Lett.* (2001), 1, 3161. Compounds of formula (XII) are commercially available. This reaction is shown in Scheme 10.

Scheme 10

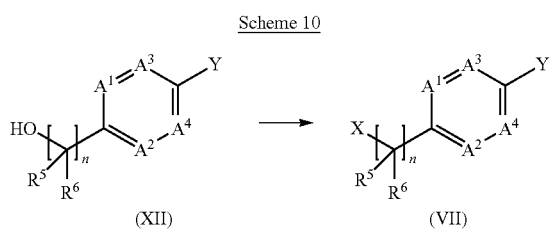

The compounds of formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use compounds of formula (I) as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising a compound of formula (I) before planting: seed, for example, can be dressed before being sown. The active compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, the compounds of formula (I) can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

The compounds of formula (I) are for example, effective against fungi and fungal vectors of disease as well as phytopathogenic bacteria and viruses. These fungi and fungal vectors of disease as well as phytopathogenic bacteria and viruses are for example:

*Absidia corymbifera*, *Alternaria* spp, *Aphanomyces* spp, *Ascochyta* spp, *Aspergillus* spp. including *A. flavus*, *A. fumigatus*, *A. nidulans*, *A. niger*, *A. terrus*, *Aureobasidium* spp. including *A. pullulans*, *Blastomyces dermatitidis*, *Blumeria graminis*, *Bremia lactucae*, *Botryosphaeria* spp. including *B. dothidea*, *B. obtusa*, *Botrytis* spp. including *B.*

*cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca* (*Sphaerotheca fuliginea*), *Sporothorix* spp, *Stagonospora nodorum, Stemphylium* spp. *Stereum hirsutum, Thanatephorus cucumeris, Thielaviopsis basicola, Tilletia* spp, *Trichoderma* spp. including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

The compounds of formula (I) may be used for example on turf, ornamentals, such as flowers, shrubs, broad-leaved trees or evergreens, for example conifers, as well as for tree injection, pest management and the like.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by 6-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein CryIF for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (in the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophillite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "The Pesticide Manual", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as defined herein, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2,5-dimethylphenoxymethyl) phenyl]-2-methoxy-iminoacetamide, 4-bromo-2-cyano-N, N-dimethyl-6-trifluoromethylbenzimidazole-1-sulphonamide, a-[N-(3-chloro-2,6-xylyl)-2-methoxyacetamido]-γ-butyrolactone, 4-chloro-2-cyano-N,-dimethyl-5-p-tolylimidazole-1-sulfonamide, N-allyl-4,5,-dimethyl-2-trimethylsilylthiophene-3-carboxamide, N-(I-cyano-1,2-dimethylpropyl)-2-(2,4-dichlorophenoxy) propionamide, N-(2-methoxy-5-pyridyl)-cyclopropane carboxamide, (.+−.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy] phenyl]-3-methoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E), (E)-2-[2-(5,6-dimethylpyrazin-2-ylmethyloximinomethyl) phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2(5H)-furanone; 4,5-dichlorodithiazolinone, 4,5-benzodithiazolinone, 4,5-trimethylened ithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1,1'-dioxide, dichlofluanid, diclomezine, dichlone, dicloran, dichlorophen, dichlozoline, diclobutrazol, diclocymet, diethofencarb, difenoconazole, difenzoquat, diflumetorim, O, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N ([methyl (methyl-thioethylideneamino-oxycarbonyl) amino] thio)-β-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-iso-propyl, nuarimol, octhilinone, ofurace, organomercury compounds, orysastrobin, osthol, oxadixyl, oxasulfuron, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-AI, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, solatenol, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following: Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai*, *kurstaki*, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Another aspect of invention is related to the use of a compound of formula (I) or of a preferred individual compound as defined herein, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula I per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) optionally together with other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

Table 1.1: This table discloses 206 specific compounds of the formula (T-1):

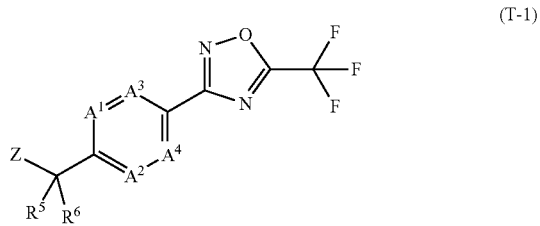

(T-1)

wherein $A^1$ is C—$R^1$, $A^2$ is C—$R^2$, $A^3$ is C—$R^3$, $A^4$ is C—$R^4$ and $R^1$, $R^2$, $R^3$, $R^4$, $R^5$, and $R^6$ are hydrogen, and Z is as defined below in Table 1.

Each of Tables 1.2 to 1.12 (which follow Table 1) make available 206 individual compounds of the formula (T-1) in which $A^1$, $A^2$, $A^3$, $A^4$, $R^1$, $R^2$, $R^3$, $R^4$, $R^5$, and $R^6$ are as specifically defined in Tables 1.2 to 1.12, which refer to Table 1 wherein Z is specifically defined.

TABLE 1

| Compound no. | Z |
| --- | --- |
| 1.001 | (3-pyridyl)triazol-1-yl |
| 1.002 | (4-chlorophenyl)tetrazol-2-yl |
| 1.003 | (4-methoxyphenyl)triazol-1-yl |
| 1.004 | [(5-chloro-3-methoxy-2-pyridyl)-oxymethyl]triazol-1-yl |
| 1.005 | [1-(2,6-diethylphenyl)-5-methyl-pyrazol-4-yl]triazol-1-yl |
| 1.006 | [1-triazol-4-yl]methyl acetate |
| 1.007 | 1,2,4-triazol-1-yl |
| 1.008 | 1,2,4-triazol-1-yl-3-carbonitrile |
| 1.009 | 1,2,4-triazol-2-yl-3-amine |
| 1.010 | 1,2,4-triazol-2-yl-3-carbonitrile |
| 1.011 | 1,2,4-triazol-4-yl |
| 1.012 | 1,2,4-triazol-4yl-3-amine |

TABLE 1-continued

| Compound no. | Z |
| --- | --- |
| 1.013 | 1-[pyrrol-2-yl]ethanone |
| 1.014 | 1H-triazol-4-ylmethyl acetate |
| 1.015 | 2-(4-pyridyl)benzimidazol-1-yl |
| 1.016 | 2-(trifluoromethyl)benzimidazol-1-yl |
| 1.017 | 2,4-dimethylimidazol-1-yl |
| 1.018 | 2-bromoimidazol-1-yl |
| 1.019 | 2-ethylbenzimidazol-1-yl |
| 1.020 | 2-isopropylimidazol-1-yl |
| 1.021 | 2-methylimidazol-1-yl |
| 1.022 | 2-phenylimidazol-1-yl |
| 1.023 | 3-(cyano)-1,2,4-triazol-1-yl |
| 1.024 | 3-(trifluoromethyl)-1,2,4-triazol-1-yl |
| 1.025 | 3-(trifluoromethyl)pyrazol-1-yl |
| 1.026 | 3,4,5-trimethylpyrazol-1-yl |
| 1.027 | 3,5-bis(difluoromethyl)pyrazol-1-yl |
| 1.028 | 3,5-bis(trifluoromethyl)pyrazol-1-yl |
| 1.029 | 3,5-dimethylpyrazol-1-yl |
| 1.030 | 3,5-ethylpyrazol-1-yl |
| 1.031 | 3-[4-[[4-(1-ethyl-3-methyl-pyrazol-4-yl)triazol-1-yl |
| 1.032 | 3-[4-[[4-(1-ethyl-5-methyl-pyrazol-4-yl)triazol-1-yl |
| 1.033 | 3-benzylsulfanyl-1,2,4-triazol-1-yl |
| 1.034 | 3-benzylsulfanyl-1,2,4-triazol-4-yl |
| 1.035 | 3-bromo-5-methoxy-1,2,4-triazol-1-yl |
| 1.036 | 3-chloropyrazol-1-yl |
| 1.037 | 3-ethylsulfanyl-1,2,4-triazol-1-yl |
| 1.038 | 3-propylsulfanyl-1,2,4-triazol-1-yl |
| 1.039 | 4-(1-ethyl-3-methylpyrazol-4-yl)triazol-1-yl |
| 1.040 | 4-(1-ethyl-5-methylpyrazol-4-yl)triazol-1-yl |
| 1.041 | 4-(2-pyridyl)triazol-1-yl |
| 1.042 | 4-(3-methylimidazol-4-yl)triazol-1-yl |
| 1.043 | 4-(3-methylimidazol-4-yl)triazol-1-yl |
| 1.044 | 4-(3-pyridyl)triazol-1-yl |
| 1.045 | 4-(3-thienyl)triazol-1-yl |
| 1.046 | 4-(4-fluorophenyl)triazol-1-yl |
| 1.047 | 4-(4-methoxyphenyl)triazol-1-yl |
| 1.048 | 4-(ethoxymethyl)triazol-1-yl |
| 1.049 | 4-(phenoxymethyl)triazol-1-yl |
| 1.050 | 4-(p-tolyl)triazol-1-yl |
| 1.051 | 4-(triazolo[4,5-b]pyridin-1-yl |
| 1.052 | 4-(triazolo[4,5-b]pyridin-3-yl |
| 1.053 | 4-(triazolo[4,5-b]pyridin-4-yl |
| 1.054 | 4-(trifluoromethyl)imidazol-1-yl |
| 1.055 | 4-(trifluoromethyl)pyrazol-1-yl |
| 1.056 | 4,5-dichloroimidazol-1-yl |
| 1.057 | 4-[(5-chloro-3-methoxy-2-pyridyl)oxymethyl]triazol-1-yl |
| 1.058 | 4-bromo-2-methyl-imidazol-1-yl |
| 1.059 | 4-bromoimidazol-1-yl |
| 1.060 | 4-bromopyrazol-1-yl |
| 1.061 | 4-chlorobenzimidazol-1-yl |
| 1.062 | 4-chlorophenyl)imidazol-1-yl |
| 1.063 | 4-chloropyrazol-1-yl |
| 1.064 | 4-cyclopentyltriazol-1-yl |
| 1.065 | 4-cyclopropyltriazol-1-yl |
| 1.066 | 4-fluorophenyl)imidazol-1-yl |
| 1.067 | 4-iodoimidazol-1-yl |
| 1.068 | 4-iodopyrazol-1-yl |
| 1.069 | 4-isobutyltriazol-1-yl |
| 1.070 | 4-methylimidazol-1-yl |
| 1.071 | 4-phenylimidazol-1-yl |
| 1.072 | 4-phenyltriazol-1-yl |
| 1.073 | 4-pyrazol-1-yl |
| 1.074 | 4-tert-butyltriazol-1-yl |
| 1.075 | 4-trimethylsilyltriazol-1-yl |
| 1.076 | 5-(cyano)-1,2,4-triazol-1-yl |
| 1.077 | 5-(trifluoromethyl)-1,2,4-triazol-1-yl |
| 1.078 | 5,5-dimethyl-4H-oxazol-2-yl |
| 1.079 | 5,6-dichlorobenzotriazol-1-yl |
| 1.080 | 5,6-dihydrocyclopenta[c]pyrrol-1-yl-4-one |
| 1.081 | 5-bromo-3-methoxy-1,2,4-triazol-1-yl |
| 1.082 | 5-chloro-3-(trifluoromethyl)-1,2,4-triazol-1-yl |
| 1.083 | 5-chlorobenzotriazol-2-yl |

TABLE 1-continued

| Compound no. | Z |
|---|---|
| 1.084 | 5-ethylsulfanyl-1,2,4-triazol-1-yl |
| 1.085 | 5-iodoimidazol-1-yl |
| 1.086 | 5-methoxy-1,2,4-triazol-1-yl-3-amine |
| 1.087 | 5-methoxy-1,2,4-triazol-2-yl-3-amine |
| 1.088 | 5-methoxyindol-1-yl |
| 1.089 | 5-methyl-3-(trifluoromethyl)pyrazol-1-yl |
| 1.090 | 5-methylindol-1-yl |
| 1.091 | 5-methyl-pyrazol-1-yl-3-carbonitrile |
| 1.092 | 5-methyl-pyrazol-1-yl-3-ol |
| 1.093 | 5-phenylimidazol-1-yl |
| 1.094 | 5-phenyltriazol-1-yl |
| 1.095 | 5-propylsulfanyl-1,2,4-triazol-1-yl |
| 1.096 | 6-chloro-5-fluoro-benzimidazol-1-yl |
| 1.097 | 6-chloroindol-1-yl |
| 1.098 | 6-fluoroindol-1-yl |
| 1.099 | 6-methoxypyrid-3-yl |
| 1.100 | 7-chlorobenzimidazol-1-yl |
| 1.101 | benzotriazol-1-yl |
| 1.102 | benzotriazol-2-yl |
| 1.103 | dimethyl imidazol-1-yl-4,5-dicarboxylate |
| 1.104 | ethyl 2-[1-pyrazol-3-yl]pyridine-3-carboxylate |
| 1.105 | ethyl 3-(difluoromethyl)-pyrazol-1-yl-4-carboxylate |
| 1.106 | ethyl 3-(trifluoromethyl)-pyrazol-1-yl-4-carboxylate |
| 1.107 | ethyl 4-phenyl-pyrazol-1-yl-3-carboxylate |
| 1.108 | ethyl 5-(difluoromethyl)-pyrazol-1-yl-4-carboxylate |
| 1.109 | ethyl 5-cyclopropyl-pyrazol-1-yl-3-carboxylate |
| 1.110 | ethyl 5-cyclopropyl-pyrazol-2-yl-3-carboxylate |
| 1.111 | ethyl 5-methyl-imidazol-3-yl-4-carboxylate |
| 1.112 | ethyl 5-propyl-imidazol-3-yl-4-carboxylate |
| 1.113 | ethyl 5-propyl-imidazol-4-yl-4-carboxylate |
| 1.114 | ethyl pyrazl-1-yl-4-carboxylate |
| 1.115 | imidazo-1-yl-carbonitrile |
| 1.116 | imidazol-1-yl |
| 1.117 | imidazol-1-yl-4,5-dicarbonitrile |
| 1.118 | imidazol-1-yl-4-carbaldehyde |
| 1.119 | imidazol-3-yl-4-carbaldehyde |
| 1.120 | indazol-1-yl |
| 1.121 | indazol-1-yl-3-carbonitrile |
| 1.122 | indazol-2-yl |
| 1.123 | methyl 1,2,4-triazol-1-yl-3-carboxylate |
| 1.124 | methyl 1,2,4-triazol-2-yl-3-carboxylate |
| 1.125 | methyl 1,2,4-triazol-4-yl-3-carboxylate |
| 1.126 | methyl 1H-1,2,4-triazole-3-carboxylate |
| 1.127 | methyl 1H-1,2,4-triazole-5-carboxylate |
| 1.128 | methyl 2-methyl-pyrrole-1-yl-3-carboxylate |
| 1.129 | methyl 3-(methoxymethyl)-pyrazol-1-yl-4-carboxylate |
| 1.130 | methyl 3-cyclopropyl-pyrazol-4-yl-4-carboxylate |
| 1.131 | methyl 3-imidazol-3-yl-4-carboxylate |
| 1.132 | methyl 5-(methoxymethyl)-pyrazol-1-yl-4-carboxylate |
| 1.133 | methyl 5-cyclopropyl-pyrazol-1-yl-4-carboxylate" |
| 1.134 | methyl imidazol-1-yl-4-carboxylate |
| 1.135 | methyl indazol-1-yl-4-carboxylate |
| 1.136 | methyl indazol-2-yl-4-carboxylate |
| 1.137 | methyl indol-1-yl-4-carboxylate |
| 1.138 | methyl pyrazol-yl-e-4-carboxylate |
| 1.139 | N-(2-methoxyethyl) pyrazol-1-yl 4-carboxamide |
| 1.140 | N-(cyclopropylmethyl) pyrazol-4-yl-4-carboxamide |
| 1.141 | N,N-dimethyl-1,2,4-triazol-1-yl-3-amine |
| 1.142 | N,N-dimethyl-pyrazol-1-yl-4-carboxamide |
| 1.143 | N-[1-methyl-1-(1H-triazol-4-yl)ethyl]benzamide |
| 1.144 | N-2-[1-[imidazol-4-yl]ethyl] acetamide |
| 1.145 | N-cyclopropyl-pyrazol-1-yl-4-carboxamide |
| 1.146 | N-methyl-pyrazol-yl-4-carboxamide |
| 1.147 | N-prop-2-ynyl pyrazol-1-yl-4-carboxamide |
| 1.148 | pyrazol-1-yl |
| 1.149 | pyrazol-1-yl-3-carbaldehyde |
| 1.150 | pyrazol-1-yl-4-carbonitrile |
| 1.151 | pyrazol-1-yl-4-carboxylic acid |
| 1.152 | pyrrol-1-yl-2-carbaldehyde |
| 1.153 | pyrrol-1-yl-3-carbonitrile |
| 1.154 | pyrrolo[2,3-b]pyridin-1-yl |
| 1.155 | pyrrolo[3,2-b]pyridin-1-yl-2-carbonitrile |
| 1.156 | pyrrolo[3,2-b]pyridin-4-yl-2-carbonitrile |
| 1.157 | tert-butyl N-(1H-triazol-4-ylmethyl)carbamate |
| 1.158 | triazol-1-yl |
| 1.159 | triazol-2-yl |
| 1.160 | triazolo[4,5-b]pyridin-2-yl |
| 1.161 | trimethyl-triazol-4-yl silane |
| 1.162 | 1,2,4-triazol-1-yl-3-carbonitrile |
| 1.163 | N,N-diethyl-pyrazol-1-yl-4-carboxamide |
| 1.164 | N-methoxy-N-methyl-pyrazol-1-yl-4-carboxamide |
| 1.165 | morpholino-[pyrazol-4-yl]methanone |
| 1.166 | tert-butyl pyrazol-1-yl-4-carboxylate |
| 1.167 | isopropyl pyrazol-1-yl-4-carboxylate |
| 1.168 | propyl pyrazol-1-yl-4-carboxylate |
| 1.169 | 2-(dimethylamino)ethyl pyrazol-1-yl-4-carboxylate |
| 1.170 | N-methoxy-pyrazol-1-yl-4-carboxamide |
| 1.171 | N-ethyl-pyrazol-1-yl-4-carboxamide |
| 1.172 | pyrazol-1-yl-4-carboxamide |
| 1.173 | methyl triazol-1-yl-4-carboxylate |
| 1.174 | triazol-1-yl-4-carboxylic acid |
| 1.175 | N-methyl-triazol-1-yl-4-carboxamide |
| 1.176 | pyrazol-1-yl-4-carbaldehyde |
| 1.177 | N-ethyl-1-triazol-1-yl-4-carboxamide |
| 1.178 | N-methoxy-N-methyl-triazol-1-yl-4-carboxamide |
| 1.179 | ethyl triazol-1-yl-4-carboxylate |
| 1.180 | N-methoxy-triazol-1-yl-4-carboxamide |
| 1.181 | isopropyl triazol-1-yl-4-carboxylate |
| 1.182 | methyl triazol-3-yl-4-carboxylate |
| 1.183 | N,N-dimethyl-triazol-1-yl-4-carboxamide |
| 1.184 | N-(4-methoxyphenyl)-triazol-1-yl-4-carboxamide |
| 1.185 | N-(4-chlorophenyl)-triazol-1-yl-4-carboxamide |
| 1.186 | N-(4-pyridyl)-triazol-1-yl-4-carboxamide |
| 1.187 | N-methoxy-pyrazol-1-yl-4-methanimine |
| 1.188 | N-ethoxy-pyrazol-1-yl-4-methanimine |
| 1.189 | N-propoxy-pyrazol-1-yl-4-methaninmine |
| 1.190 | N-isopropoxy-pyrazol-1-yl-4-methanimine |
| 1.191 | N-benzyloxy-pyrazol-1-yl-4-methanimine |
| 1.192 | N-prop-2-ynoxy-pyrazol-1-yl-4-methanimine |
| 1.193 | N-methyl-triazol-3-yl-4-carboxamide |
| 1.194 | N-methoxy-pyrrolidin-1-yl-3-imine |
| 1.195 | N-methoxy-piperidin-1-yl-4-imine |
| 1.196 | 5-methylsulfonyl-1,2,4-triazol-1-yl |
| 1.197 | 5-methylsulfinyl-1,2,4-triazol-1-yl |
| 1.198 | 3-methylsulfonyl-1,2,4-triazol-1-yl |
| 1.199 | 3-methylsulfinyl-1,2,4-triazol-1-yl |
| 1.200 | 5-methylsulfanyl-1,2,4-triazol-1-yl |
| 1.201 | 3-methylsulfanyl-1,2,4-triazol-1-yl |
| 1.202 | 1-piperidin-1-yl |
| 1.203 | 4-morpholin-1-yl |

TABLE 1-continued

| Compound no. | Z |
|---|---|
| 1.204 | 4-thiomorpholin-1-yl |
| 1.205 | 4-methylsulfonyl-piperazin-1-yl |
| 1.206 | 2,6-dimethyl-4-morpholin-1-yl |

Table 1.2: This table discloses 206 specific compounds of formula (T-1) wherein $A^1$ is C—$R^1$, $A^2$ is C—$R^2$, $A^3$ is C—$R^3$, $A^4$ is C—$R^4$ and $R^2$, $R^3$, $R^4$, $R^5$, and $R^6$ are hydrogen, $R^1$ is fluorine, and Z is as defined above in Table 1.
Table 1.3: This table discloses 206 specific compounds of formula (T-1) wherein $A^1$ is C—$R^1$, $A^2$ is C—$R^2$, $A^3$ is C—$R^3$, $A^4$ is C—$R^4$ and $R^2$, $R^3$, $R^4$, $R^5$, and $R^6$ are hydrogen, $R^1$ is chlorine, and Z is as defined above in Table 1.
Table 1.4: This table discloses 206 specific compounds of formula (T-1) wherein $A^1$ is C—$R^1$, $A^2$ is C—$R^2$, $A^3$ is C—$R^3$, $A^4$ is C—$R^4$ and $R^2$, $R^3$, $R^4$, $R^5$, and $R^6$ are hydrogen, $R^1$ is methyl, and Z is as defined above in Table 1.
Table 1.5: This table discloses 206 specific compounds of formula (T-1) wherein $A^1$ is N, $A^2$ is C—$R^2$, $A^3$ is C—$R^3$, $A^4$ is C—$R^4$ and $R^2$, $R^3$, $R^4$, $R^5$, and $R^6$ are hydrogen, and Z is as defined above in Table 1.
Table 1.6: This table discloses 206 specific compounds of formula (T-1) wherein, $A^1$ is C—$R^1$, $A^2$ is C—$R^2$, $A^3$ is C—$R^3$, $A^4$ is C—$R^4$ and $R^1$, $R^2$, $R^4$, $R^5$, and $R^6$ are hydrogen, $R^3$ is fluorine, and Z is as defined above in Table 1.
Table 1.7: This table discloses 206 specific compounds of formula (T-1) wherein $A^1$ is C—$R^1$, $A^2$ is C—$R^2$, $A^3$ is C—$R^3$, $A^4$ is C—$R^4$ and $R^2$, $R^4$, $R^5$, $R^6$, and $R^7$ are hydrogen, $R^1$ and $R^3$ are fluorine, and Z is as defined above in Table 1.
Table 1.8: This table discloses 206 specific compounds of formula (T-1) wherein, $A^1$ is C—$R^1$, $A^2$ is C—$R^2$, $A^3$ is C—$R^3$, $A^4$ is C—$R^4$ and $R^3$, $R^4$, $R^5$, and $R^6$ are hydrogen, $R^1$ and $R^2$ are fluorine, and Z is as defined above in Table 1.
Table 1.9: This table discloses 206 specific compounds of formula (T-1) wherein $A^1$ is C—$R^1$, $A^2$ is C—$R^2$, $A^3$ is C—$R^3$, $A^4$ is C—$R^4$ and $R^1$, $R^2$, $R^3$ $R^4$, and $R^5$ are hydrogen, $R^6$ is methyl, and Z is as defined above in Table 1.
Table 1.10: This table discloses 206 specific compounds of formula (T-1) wherein $A^1$ is C—$R^1$, $A^2$ is C—$R^2$, $A^3$ is C—$R^3$, $A^4$ is C—$R^4$ and $R^2$, $R^4$ and $R^5$ are hydrogen, $R^3$ is fluorine, $R^6$ is methyl, and Z is as defined above in Table 1.
Table 1.11: This table discloses 206 specific compounds of formula (T-1) wherein $A^1$ is C—$R^1$, $A^2$ is C—$R^2$, $A^3$ is C—$R^3$, $A^4$ is C—$R^4$ and $R^1$, $R^2$, $R^5$ and $R^6$ are hydrogen, $R^3$ and $R^4$ are fluorine, and Z is as defined above in Table 1.
Table 1.12: This table discloses 206 specific compounds of formula (T-1) wherein $A^1$ is C—$R^1$, $A^2$ is C—$R^2$, $A^3$ is C—$R^3$, $A^4$ is C—$R^4$ and $R^2$, $R^3$, $R^5$ and $R^6$ are hydrogen, $R^1$ and $R^4$ are fluorine, and Z is as defined above in Table 1.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of Formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

Throughout this description, temperatures are given in degrees Celsius (° C.) and "mp." means melting point. LC/MS means Liquid Chromatography Mass Spectrometry and the description of the apparatus and the method (Methods A, B and C) is as follows:
The description of the LC/MS apparatus and the method A is:
SQ Detector 2 from Waters
Ionisation method: Electrospray
Polarity: positive and negative ions
Capillary (kV) 3.0, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650 Mass range: 100 to 900 Da
DAD Wavelength range (nm): 210 to 500
Method Waters ACQUITY UPLC with the following HPLC gradient conditions:
(Solvent A: Water/Methanol 20:1+0.05% formic acid and Solvent B: Acetonitrile+0.05% formic acid)

| Time (minutes) | A (%) | B (%) | Flow rate (ml/min) |
|---|---|---|---|
| 0 | 100 | 0 | 0.85 |
| 1.2 | 0 | 100 | 0.85 |
| 1.5 | 0 | 100 | 0.85 |

Type of column: Waters ACQUITY UPLC HSS T3; Column length: 30 mm; Internal diameter of column: 2.1 mm; Particle Size: 1.8 micron; Temperature: 60° C.
The Description of the LC/MS Apparatus and the Method B is:
SQ Detector 2 from Waters
Ionisation method: Electrospray
Polarity: positive ions
Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 140 to 800 Da
DAD Wavelength range (nm): 210 to 400
Method Waters ACQUITY UPLC with the following HPLC gradient conditions
(Solvent A: Water/Methanol 9:1+0.1% formic acid and Solvent B: Acetonitrile+0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.
The description of the LC/MS apparatus and the method C is:
SQ Detector 2 from Waters
Ionisation method: Electrospray
ACQUITY H Class UPLC, Mass Spectrometer from Waters
Polarity: positive and Negative Polarity Switch Scan Type MS1 Scan
Capillary (kV) 3.00, Cone (V) 40.00, Desolvation Temperature (° C.) 500, Cone Gas Flow (L/Hr) 50, Desolvation Gas Flow (L/Hr) 1000
Mass range: 0 to 2000 Da
DAD Wavelength range (nm): 200 to 350
Method Waters ACQUITY UPLC with the following HPLC gradient conditions
(Solvent A: Water +, 0.1% formic acid and Solvent B: Acetonitrile)

| Time (minutes) | A (%) | B (%) | Flow rate (ml/min) |
| --- | --- | --- | --- |
| 0 | 70 | 30 | 0.5 |
| 0.05 | 70 | 30 | 0.5 |
| 0.8 | 5 | 95 | 0.5 |
| 1.8 | 5 | 95 | 0.5 |
| 2.45 | 70 | 30 | 0.5 |
| 2.50 | 70 | 30 | 0.5 |

Type of column: Waters ACQUITY UPLC BEH C18; Column length: 50 mm; Internal diameter of column: 2.1 mm; Particle Size: 1.7 micron; Temperature: 35° C.

Where necessary, enantiomerically pure final compounds may be obtained from racemic materials as appropriate via standard physical separation techniques, such as reverse phase chiral chromatography, or through stereoselective synthetic techniques, eg, by using chiral starting materials.

FORMULATION EXAMPLES

| Wettable powders | a) | b) | c) |
| --- | --- | --- | --- |
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
| --- | --- |
| active ingredient [compound of formula (I)] | 10% |
| octylphenol polyethylene glycol ether (4-5 mol of ethylene oxide) | 3% |
| calcium dodecylbenzenesulfonate | 3% |

| Emulsifiable concentrate | |
| --- | --- |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredient [compound of formula (I)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
| --- | --- |
| Active ingredient [compound of formula (I)] | 15% |
| sodium lignosulfonate | 2% |
| Carboxymethylcellulose | 1% |
| Kaolin | 82% |

The active ingredient is mixed and ground with the adjuvants and the mixture is moistened with water. The mixture is extruded and then dried in a stream of air.

| Coated granules | |
| --- | --- |
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
| --- | --- |
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow-Release Capsule Suspension 28 parts of a combination of the compound of formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

List of Abbreviations

AIBN=azobisisobutyronitrile

DMF=dimethylformamide

DIPEA=N,N-di-isopropylethylamine

EtOAc=ethyl acetate

HCl=hydrochloric acid mp=melting point

° C.=degrees Celsius

MeOH=methyl alcohol

NaOH=sodium hydroxide

NBS=N-bromosuccinimide min=minutes

RT=room temperature h=hour(s)

TFAA=trifluoroacetic acid anhydride

THF=tetrahydrofuran $t_R$=retention time (in minutes)

LC/MS=Liquid Chromatography Mass Spectrometry (description of the apparatus and the methods used for LC/MS analysis are given above)

Example 1

This example illustrates the preparation 3-[4-(imidazol-1-ylmethyl)phenyl]-5-(trifluoromethyl)-1,2,4-oxadiazole (Compound 1.18 of Table T1)

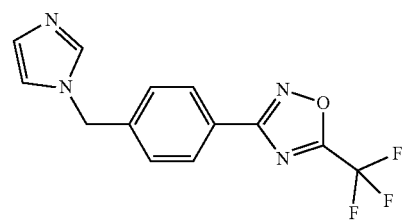 [SMILES: FC(F)(F)c1nc(-c2ccc(Cn3ccnc3)cc2)no1]

Step 1: Preparation of N'-hydroxy-4-methyl-benzamidine

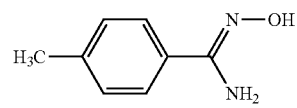

To a stirred suspension of 4-methylbenzonitrile (35 g, 0.29 mol) in ethanol (220 mL) and water (440 mL) at RT was added hydroxylamine hydrochloride (41.1 g, 0.58 mol), potassium carbonate (65.4 g, 0.47 mol) and 8-hydroxyquinoline (0.22 g, 1.5 mmol). The reaction mixture was heated at 80° C. for 4 hours. The mixture was cooled to RT and diluted with 2N HCl until pH 8. Ethanol was evaporated under reduced pressure. The mixture was filtered, washed with water and dried under vacuum to afford the title compound. LC/MS (Method A) retention time=0.23 minutes, 151.0 (M+H).

Step 2: Preparation of 3-(p-tolyl)-5-(trifluoromethyl)-1,2,4-oxadiazole

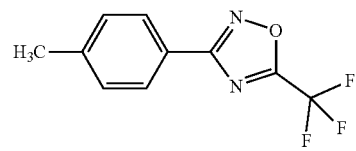 [SMILES: Cc1ccc(-c2noc(C(F)(F)F)n2)cc1]

To a stirred solution of N'-hydroxy-4-methyl-benzamidine (38.7 g, 0.25 mol) in 2-methyltetrahydrofuran (750 mL) was added TFAA at 0° C. The reaction mixture was stirred at 15° C. for two hours and then diluted with water. The organic layer was separated, washed successively with sodium bicarbonate solution, ammonium chloride solution, water, dried over sodium sulfate, filtered and evaporated to dryness. The crude product was subjected to flash chromatography over silica gel (750 g pre-packed column) with heptane/EtOAc 99:1 to 90:10 to afford the title compound as a clear oil, which solidified after storage.

LC/MS (Method A) retention time=1.15 minutes, mass not detected.

$^1$H NMR (400 MHz, CDCl$_3$) δ ppm: 8.00 (d, 2H), 7.32 (d, 2H), 2.45 (s, 3H).

$^{19}$F NMR (400 MHz, CDCl$_3$) δ ppm: −65.41 (s).

Step 3a: Preparation of 3-[4-(bromomethyl)phenyl]-5-(trifluoromethyl)-1,2,4-oxadiazole

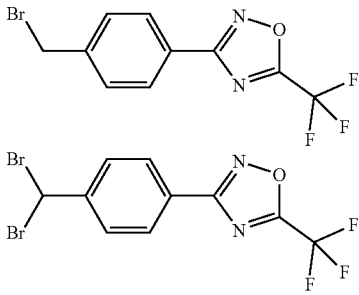

A stirred mixture of 3-(p-tolyl)-5-(trifluoromethyl)-1,2,4-oxadiazole (56.0 g, 0.24 mol) and NBS (45.4 g, 0.25 mol) in tetrachloromethane (480 mL) under argon was heated to 70° C. AIBN (4.03 g, 24 mmol) was added and the reaction mixture stirred at 65° C. for 18 hours. The mixture was cooled to RT and diluted with dichloromethane and water and the layers were separated. The organic layer was washed with sodium bicarbonate solution, dried over sodium sulfate, filtered and evaporated to dryness. The crude residue was subjected to flash chromatography over silica gel (750 g pre-packed column) with cyclohexane/EtOAc 100:0 to 95:5 to afford the title compound as a white solid mp: 58-63° C.

$^1$H NMR (400 MHz, CDCl$_3$) δ ppm: 8.11 (d, 2H), 7.55 (d, 2H), 4.53 (s, 2H).

$^{19}$F NMR (400 MHz, CDCl$_3$) δ ppm: −65.32 (s).

3-[4-(dibromomethyl)phenyl]-5-(trifluoromethyl)-1,2,4-oxadiazole was isolated as by-product as a white solid mp: 61-66° C.

$^1$H NMR (400 MHz, CDCl$_3$) δ ppm: 8.15 (d, 2H), 7.73 (d, 2H), 6.68 (s, 1H).

$^{19}$F NMR (400 MHz, CDCl$_3$) δ ppm: −65.34 (s).

Step 3b: Preparation of 3-[4-(bromomethyl)phenyl]-5-(trifluoromethyl)-1,2,4-oxadiazole from 3-[4-(dibromomethyl)phenyl]-5-(trifluoromethyl)-1,2,4-oxadiazole

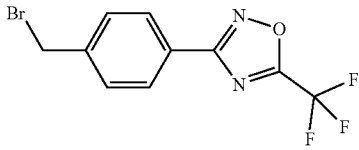 [SMILES: FC(F)(F)c1nc(-c2ccc(CBr)cc2)no1]

To a stirred 1:9 ratio mixture of 3-[4-(bromomethyl)phenyl]-5-(trifluoromethyl)-1,2,4-oxadiazole and 3-[4-(dibromomethyl)phenyl]-5-(trifluoromethyl)-1,2,4-oxadiazole (10.2 g) in acetonitrile (95 mL), water (1.9 mL) and DIPEA (6.20 ml, 35.7 mmol) was added diethylphosphite (4.7 mL, 35.7 mmol) at 5° C. The mixture was stirred at 5-10° C. for two hours, water and 1M HCl was added and acetonitrile evaporated under reduced pressure. The white slurry was extracted three times with dichloromethane. The combined organic layers were dried over sodium sulfate, and filtered. The solvent was removed under reduced pressure and the resultant crude residue subjected to flash chromatography over silica gel (40 g pre-packed column) with cyclohexane/EtOAc 99:1 to 9:1 to afford 3-[4-(bromomethyl)phenyl]-5-(trifluoromethyl)-1,2,4-oxadiazole.

$^1$H NMR (400 MHz, CDCl$_3$) δ ppm: 8.11 (d, 2H), 7.55 (d, 2H), 4.53 (s, 2H).

$^{19}$F NMR (400 MHz, CDCl$_3$) δ ppm: −65.32 (s).

Step 4: Preparation of 3-[4-(imidazol-1-ylmethyl)phenyl]-5-(trifluoromethyl)-1,2,4-oxadiazole A solution of 3-[4-(bromomethyl)phenyl]-5-(trifluoromethyl)-1,2,4-oxadiazole (100 mg, 0.31 mmol), imidazole (1.5 equiv., 0.46 mmol), and potassium carbonate (2 equiv., 0.62 mmol) in acetonitrile (3.0 mL) was heated in a microwave oven for 30 minutes at 120° C. Solids were removed by filtration and washed with ethyl acetate and the mother liquors evaporated to give a crude residue. Further solvent was removed under reduced pressure and the resultant residue purified by flash chromatography over silica gel (cyclohexane:EtOAc eluent gradient 1:0 to 0:1) to afford 3-[4-(imidazol-1-ylmethyl)phenyl]-5-(trifluoromethyl)-1,2,4-oxadiazole as a yellow solid. LC/MS (Method A) retention time=0.69 minutes, 295 (M+H). mp: 45-55° C.

$^1$H NMR (400 MHz, CDCl$_3$) δ ppm: 8.22 (d, 2H), 7.61 (d, 2H), 7.28 (d, 2H), 7.14 (s, 1H), 5.20 (s, 2H).

$^{19}$F NMR (400 MHz, CDCl$_3$) δ ppm: −65.39 (s).

Example 2

This example illustrates the preparation 3-[4-[(4-cyclopentyltriazol-1-yl)methyl]phenyl]-5-(trifluoromethyl)-1,2,4-oxadiazole (Compound 1.24 of Table T1)

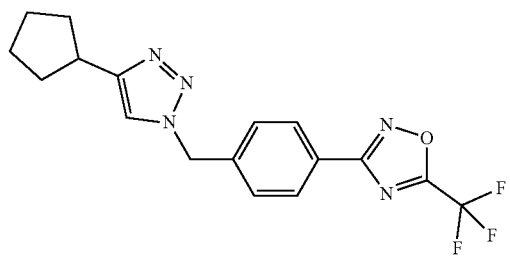 [SMILES: FC(F)(F)c1nc(-c2ccc(Cn3cc(C4CCCC4)nn3)cc2)no1]

A solution of 3-[4-(bromomethyl)phenyl]-5-(trifluoromethyl)-1,2,4-oxadiazole (153 mg, 0.49 mmol) was dissolved in dimethylformamide (1.5 mL), isopropanol (1 mL) and water (1 mL). To the resultant white suspension was introduced sodium azide (64 mg), copper (II) sulfate (28 mg), and copper cyanide (18 mg). To the fine beige suspension was introduced ethynyl cyclopentane (0.06 mL) and triethylamine (1 mL) and the light green, cloudy solution was stirred over night at RT. The mixture was poured into a separatory funnel containing water and EtOAc, the layers were separated, and the aqueous fraction was then extracted with ethyl acetate. The combined organics were dried over sodium sulfate and concentrated under reduced pressure to afford the crude as a green oil. The crude was subject to combiflash chromatography over silicagel (heptane:EtOAc eluent gradient 99:1 to 1:1) to afford 3-[4-[(4-cyclopentyltriazol-1-yl)methyl]phenyl]-5-(trifluoromethyl)-1,2,4-oxadiazole as a white solid. LC/MS (Method A) retention time=1.10 minutes, 364 (M+H). mp: 117-119° C.

$^1$H NMR (400 MHz, CDCl$_3$) δ ppm: 8.12 (d, 2H), 7.39 (d, 2H), 7.22 (s, 1H), 5.57 (s, 1H), 3.18 (m, 1H), 2.09 (m, 2H), 1.75 (m, 2H), 1.70 (m, 4H).

$^{19}$F NMR (400 MHz, CDCl$_3$) δ ppm: −65.39 (s).

Example 3

This example illustrates the preparation of 3-[4-[1-(6-methoxy-3-pyridyl)ethyl]phenyl]-5-(trifluoromethyl)-1,2,4-oxadiazole (Compound 1.42 of Table T1 below)

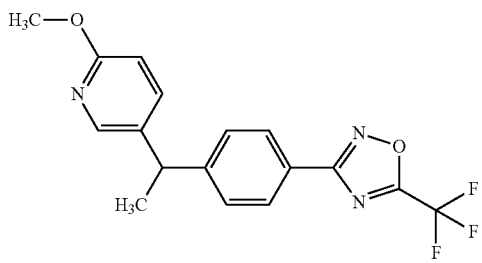 [SMILES: COc1ccc(C(C)c2ccc(-c3noc(C(F)(F)F)n3)cc2)cn1]

Step 1: Preparation of 4-[5-(trifluoromethyl)-1,2,4-oxadiazol-3-yl]benzoyl chloride

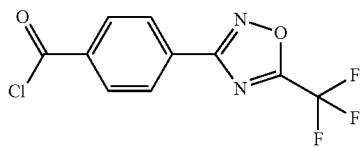 [SMILES: O=C(Cl)c1ccc(-c2noc(C(F)(F)F)n2)cc1]

4-[5-(trifluoromethyl)-1,2,4-oxadiazol-3-yl]benzoic acid (4.00 g, 15.0 mmol) was suspended in dichloromethane (90 mL) DMF (0.01 mL, 0.150 mmol) was added followed by oxalyl chloride (1.46 mL, 16.5 mmol). The mixture was heated at reflux for 2 hours. The mixture was evaporated under reduced pressure to afford 4.15 g of 4-[5-(trifluoromethyl)-1,2,4-oxadiazol-3-yl]benzoyl chloride as a yellow solid.

Step 2: Preparation of N-methoxy-N-methyl-4-[5-(trifluoromethyl)-1,2,4-oxadiazol-3-yl]benzamide

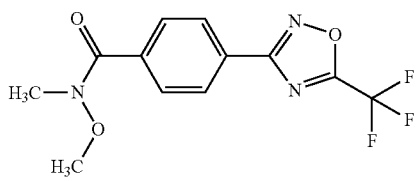 [SMILES: CON(C)C(=O)c1ccc(-c2noc(C(F)(F)F)n2)cc1]

A solution of 4-[5-(trifluoromethyl)-1,2,4-oxadiazol-3-yl]benzoyl chloride from Step 1 (4.15 g, 14.6 mmol) in dichloromethane (20 mL) was added drop wise at room temperature to a stirred solution of N-methoxymethanamine (1.10 g, 17.5 mmol) and triethylamine (3.10 ml, 21.8 mmol) in dichloromethane (80 mL). The mixture was stirred at room temperature for 18 hours. The reaction mixture was poured into water extracted twice with dichloromethane. The combined organic layers were washed with brine, dried over sodium sulfate, and filtered. The solvent was removed under reduced pressure and the resultant crude residue was subjected to flash chromatography over silica gel (heptane:EtOAc eluent gradient 9:1 to 65:35) to afford 4.12 g of N-methoxy-N-methyl-4-[5-(trifluoromethyl)-1,2,4-oxadi- azol-3-yl]benzamide as a solid. LC/MS (Method A) retention time=0.97 minutes, 302 (M+H).

$^1$H NMR (400 MHz, CDCl$_3$) δ ppm: 8.18 (d, 2H), 7.84 (d, 2H), 3.56 (s, 3H), 3.40 (s, 3H).

Step 3: Preparation of 4-[5-(trifluoromethyl)-1,2,4-oxadiazol-3-yl]benzaldehyde

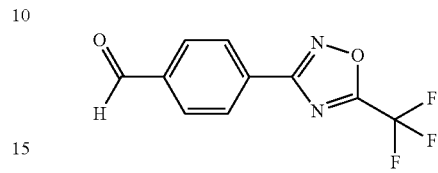

In a 75-mL multi neck flask equipped with stirrer, thermometer at −78° C. under argon, DIBAL-H, 1.0M in toluene (16 mL, 16.0 mmol) was added drop-wise to a solution of N-methoxy-N-methyl-4-[5-(trifluoromethyl)-1,2,4-oxadi- azol-3-yl]benzamide (4.10 g, 13.3 mmol) in 2-methyltetra- hydrofuran (90 mL). The mixture was stirred two hours at −78° C. and for one hour temperature was let increase to 0° C. Complete conversion observed by LC-MS. The mixture was quenched by drop wise addition of sat. ammonium chloride solution. Precipitation of a white solid occurred. 4 M HCl was added until full solubilisation. The mixture was extracted thrice with ethyl acetate. Combined organics were dried over magnesium sulfate and evaporated to afford the crude as beige solid. The crude was subject to combiflash chromatography over silica gel (heptane:EtOAc eluent gradient 99:1 to 90:10) to afford 2.93 g of 4-[5-(trifluorom- ethyl)-1,2,4-oxadiazol-3-yl]benzaldehyde as a white solid. mp: 40-50° C.

$^1$H NMR (400 MHz, CDCl$_3$) δ ppm: 10.12 (s, 1H), 8.31 (d, 2H), 8.05 (d, 2H).

$^{19}$F NMR (400 MHz, CDCl$_3$) δ ppm: −65.29 (s).

Step 4: Preparation of 1-[4-[5-(trifluoromethyl)-1,2,4-oxadiazol-3-yl]phenyl]ethanol

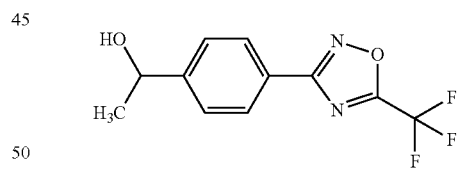

In a 50 mL flask dried and under argon, 4-[5-(trifluorom- ethyl)-1,2,4-oxadiazol-3-yl]benzaldehyde (1.36 mol) was dissolved in THF (10 mL) and cooled to −78° C. via a dry ice acetone bath. To this solution was introduced dropwise methyl magnesium bromide (0.70 mL, 2.03M in diethyl ether). The mixture was stirred for 1 h at −78° C. and then was quenched with a saturated aqueous ammonium chloride solution. The dry ice bath was removed, and the reaction was stirred at rt 5 min. it was then extracted with ethyl acetate. The combined organics were dried over sodium sulfate and concentrated under reduced pressure to afford the crude as a colourless oil. The crude was subject to combiflash chromatography over silicagel (heptane:EtOAc eluent gradient 99:1 to 1:1) to afford 1-[4-[5-(trifluoromethyl)-1,2,4-oxadi- azol-3-yl]phenyl]ethanol as a white solid.

¹H NMR (400 MHz, CDCl₃) δ ppm: 8.12 (d, 2H), 7.54 (d, 2H), 5.00 (s, 1H), 1.54 (d, 3H).
¹⁹F NMR (400 MHz, CDCl₃) δ ppm: −65.31 (s).

Step 5: Preparation of 1-[4-[5-(trifluoromethyl)-1,2,4-oxadiazol-3-yl]phenyl]ethanone

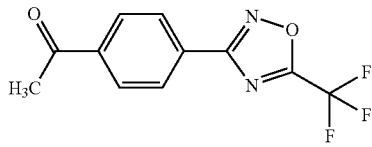 [SMILES: CC(=O)c1ccc(-c2noc(C(F)(F)F)n2)cc1]

In a 50 mL flask dried and under argon, 1-[4-[5-(trifluoromethyl)-1,2,4-oxadiazol-3-yl]phenyl]ethanol (1.36 mol) was dissolved in dichloromethane (10 mL). To this solution was introduced manganese oxide (40.6 mmol) and the heterogenous mixture was stirred for overnight at RT. The reaction solution was then filtered over a pad of celite and after washings with dichloromethane the combined organics were concentrated under reduced pressure to afford crude 1-[4-[5-(trifluoromethyl)-1,2,4-oxadiazol-3-yl]phenyl]ethanone as a white solid which was used directly without further purification.
¹H NMR (400 MHz, CDCl₃) δ ppm: 8.24 (d, 2H), 8.12 (d, 2H), 2.67 (s, 1H), 1.56 (d, 3H).
¹⁹F NMR (400 MHz, CDCl₃) δ ppm: −65.39 (s).

Step 6: Preparation of 4-methyl-N-[(E)-1-[4-[5-(trifluoromethyl)-1,2,4-oxadiazol-3-yl]phenyl]ethylideneamino]benzenesulfonamide

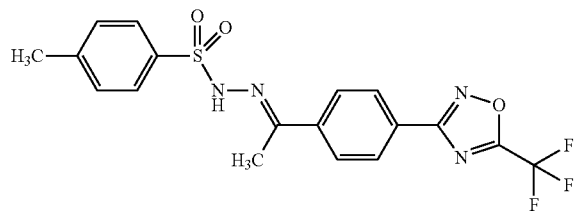 [SMILES: C/C(=N\NS(=O)(=O)c1ccc(C)cc1)c1ccc(-c2noc(C(F)(F)F)n2)cc1]

In a 50 mL flask dried and under argon, 1-[4-[5-(trifluoromethyl)-1,2,4-oxadiazol-3-yl]phenyl]ethanone (1.05 mol) was dissolved in methanol (10 mL). To this solution was introduced 4-methylbenzenesulfonohydrazide (1.16 mmol) and the resultant white suspension was stirred for overnight at RT. The reaction solution was then concentrated under reduced pressure to afford crude 4-methyl-N-[(E)-1-[4-[5-(trifluoromethyl)-1,2,4-oxadiazol-3-yl]phenyl]ethylideneamino]benzenesulfonamide as a white solid which was used directly without further purification.
¹H NMR (400 MHz, CDCl₃) δ ppm: 8.12 (d, 2H), 7.93 (d, 2H), 7.81 (d, 2H), 7.60 (s_{br}, 1H), 7.36 (d, 2H), 2.44 (s, 3H), 2.17 (s, 3H).
¹⁹F NMR (400 MHz, CDCl₃) δ ppm: −65.34 (s).

Step 7: Preparation of 3-[4-[1-(6-methoxy-3-pyridyl)ethyl]phenyl]-5-(trifluoromethyl)-1,2,4-oxadiazole In a 10 mL flask dried and under argon, 4-methyl-N-[(E)-1-[4-[5-(trifluoromethyl)-1,2,4-oxadiazol-3-yl]phenyl]ethylideneamino]benzenesulfonamide (0.47 mol) was dissolved in dioxane (1.4 mL). To this solution was introduced 2-methoxypyridine boronic acid (0.71 mmol) and the resultant beige suspension was stirred for 3 h at 110° C. After cooling to RT, the reaction solution was then concentrated under reduced pressure and the crude was subject to combiflash chromatography over silicagel (cyclohexane:EtOAc eluent gradient 99:1 to 4:1) to afford 3-[4-[1-(6-methoxy-3-pyridyl)ethyl]phenyl]-5-(trifluoromethyl)-1,2,4-oxadiazole as a yellow oil.
¹H NMR (400 MHz, CDCl₃) δ ppm: 8.07 (d, 1H), 8.03 (d, 2H), 7.38 (d, 1H), 7.36 (d, 2H), 6.69 (d, 1H), 4.18 (q, 1H), 3.92 (s, 3H), 1.67 (d, 3H).
¹⁹F NMR (400 MHz, CDCl₃) δ ppm: −65.38 (s).

Example 4

This example illustrates the preparation of 3-[4-[1-(3,5-dimethylpyrazol-1-yl)ethyl]phenyl]-5-(trifluoromethyl)-1,2,4-oxadiazole (Compound 1.303 of Table T1 below).

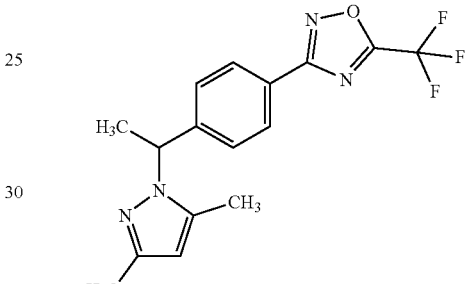

Step 1: Preparation of 3-[4-(1-bromoethyl)phenyl]-5-(trifluoromethyl)-1,2,4-oxadiazole

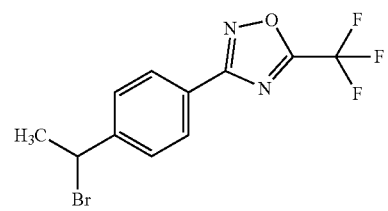 [SMILES: CC(Br)c1ccc(-c2noc(C(F)(F)F)n2)cc1]

To a solution of 1-[4-[5-(trifluoromethyl)-1,2,4-oxadiazol-3-yl]phenyl]ethanol (1.15 g, 4.45 mmol) in dichloromethane (15 mL) cooled to 0° C. using an ice bath was added tribromophosphane (0.465 ml, 4.90 mmol) over 30 minutes and the reaction mixture was stirred for 1.5 hrs. Then, an ice bath was used to cool the contents and a 10% sodium metabisulphite (50 ml) was introduced. After 15 minutes, the aqueous layer was extracted with dichloromethane and the total combined organic layer was washed with water and dried over Na₂SO₄, filtered and concentrated under reduced pressure. The resultant crude residue was purified by combiflash chromatography over silica gel using cyclohexane as eluent to afford pure 3-[4-(1-bromoethyl)phenyl]-5-(trifluoromethyl)-1,2,4-oxadiazole (1 g, 71% yield) as white solid.
¹H NMR (400 MHz, DMSO-d6) δ ppm: 8.07 (m, 2H), 7.75 (m, 2H), 5.76 (s, 1H), 5.59 (q, 1H), 2.02 (d, 3H).

Step 2: Preparation of 3-[4-[1-(3,5-dimethylpyrazol-1-yl)ethyl]phenyl]-5-(trifluoromethyl)-1,2,4-oxadiazole 3-[4-(1-bromoethyl)phenyl]-5-(trifluoromethyl)-1,2,4-oxadiazole (150 mg, 0.47 mmol), 3,5-dimethylpyrazole (0.07 g, 0.70 mmol) and potassium carbonate (0.130 g, 0.93 mmol) were dissolved in acetonitrile (5 mL) in a microwave vial. The mixture was then heated in the microwave at 100° C. for 30 minutes. The reaction mixture was diluted with water (20 mL) and extracted with ethyl acetate. The total combined organic layer was washed with brine solution, dried over anhydrous $Na_2SO_4$, filtered, and concentrated at reduced pressure. The resultant crude residue was purified by combiflash chromatography over silica gel (cyclohexane: EtOAc eluent gradient 92:8) to afford pure 3-[4-[1-(3,5-dimethylpyrazol-1-yl)ethyl]phenyl]-5-(trifluoromethyl)-1,2,4-oxadiazole (55 mg, 35%) as a light yellow gummy mass. LC/MS (Method C) retention time=1.61 minutes, 337 (M+H).

$^1$H NMR (400 MHz, $CDCl_3$) δ ppm: 8.04 (d, 2H), 7.25 (m, 2H), 5.87 (s, 1H), 5.41 (q, 1H), 2.30 (s, 3H), 2.12 (s, 3H), 1.95 (d, 3H).

Example 5

This example illustrates the preparation of 3-[4-[2-(3,5-dimethylpyrazol-1-yl)ethyl]phenyl]-5-(trifluoromethyl)-1,2,4-oxadiazole (Compound 1.309 of Table T1 below).

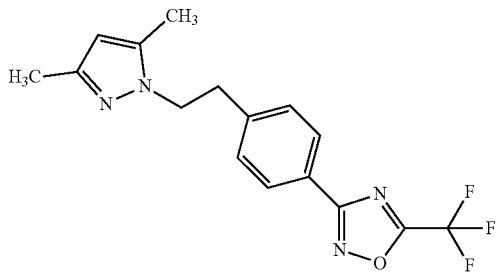 [SMILES: Cc1cc(C)n(CCc2ccc(-c3noc(C(F)(F)F)n3)cc2)n1]

Step 1 Preparation of 3-[4-(2-bromoethyl)phenyl]-5-(trifluoromethyl)-1,2,4-oxadiazole

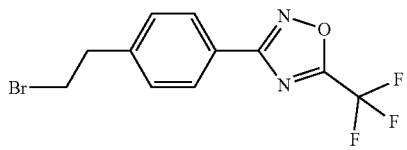 [SMILES: FC(F)(F)c1nc(-c2ccc(CCBr)cc2)no1]

To a solution of 4-(2-bromoethyl)benzonitrile (2.0 g, 9.5 mmol) in ethanol (32 mL) was added hydroxylamine hydrochloride (2 equiv., 19 mmol) followed by triethylamine (4.5 equiv., 43 mmol). The reaction contents were allowed to stir at ambient temperature for 12 hrs and the volatiles were then removed at reduced pressure. The resultant crude mass was dissolved in tetrahydrofuran (60 mL), cooled to 00° C. using an ice bath and trifluoroacetic anhydride (3 equiv., 29 mmol) was slowly introduced followed by the dropwise addition of pyridine (4 equiv., 38 mmol) at 0° C. After warming to 25° C. and stirring for 5 hours the reaction mixture was diluted with water (100 mL) and extracted with ethyl acetate. The combined total organic layer was washed with 1N HCl and brine solution. The organic layer thus obtained was dried over anhydrous $Na_2SO_4$, filtered, and concentrated under reduced pressure. The resultant crude residue was purified by flash chromatography over silica gel using 30% ethyl acetate in hexane as eluent to afford pure 3-[4-(2-bromoethyl)phenyl]-5-(trifluoromethyl)-1,2,4-oxadiazole (1.75 g, 57% yield) as colourless gummy mass.

$^1$H NMR (400 MHz, $CDCl_3$) δ ppm: 8.09 (d, 2H), 7.39 (d, 2H), 3.62 (t, 2H), 3.26 (t, 2H).

Step 2: Preparation of 3-[4-[2-(3,5-dimethylpyrazol-1-yl)ethyl]phenyl]-5-(trifluoromethyl)-1,2,4-oxadiazole 3-[4-(2-Bromoethyl)phenyl]-5-(trifluoromethyl)-1,2,4-oxadiazole (0.150 g, 0.467 mmol), 3,5-dimethyl-1H-pyrazole (1.5 equiv., 0.701 mmol) and potassium carbonate (0.30 g, 0.934 mmol) were dissolved in acetonitrile (5 mL) in a microwave vial and the mixture was heated in the presence of microwaves irradiation for 30 min at 100° C. Then the reaction mixture was diluted with water (20 mL) and extracted with ethyl acetate. The total combined organic layer was washed with water and brine solution. The organic layer thus obtained was dried over anhydrous $Na_2SO_4$, filtered, and concentrated under reduced pressure. The resultant crude residue was purified by flash chromatography over silica gel using 30% ethyl acetate in hexane as eluent to afford pure 3-[4-[2-(3,5-dimethylpyrazol-1-yl)ethyl]phenyl]-5-(trifluoromethyl)-1,2,4-oxadiazole (0.03 g, 16% yield) as a colorless gummy mass. LC/MS (Method C) retention time=1.67 minutes, 337 (M+H).

$^1$H NMR (400 MHz, $CDCl_3$) δ ppm: 8.03 (m, 2H), 7.19 (m, 2H), 5.73 (s, 1H), 4.21 (t, 2H), 3.21 (t, 2H), 2.28 (s, 3H), 1.88 (s, 3H).

Example 6

This example illustrates the preparation of ethyl 1-[2-[4-[5-(trifluoromethyl)-1,2,4-oxadiazolyl]phenyl]ethyl]pyrazole-4-carboxylate (Compound 1.310 of Table T1 below).

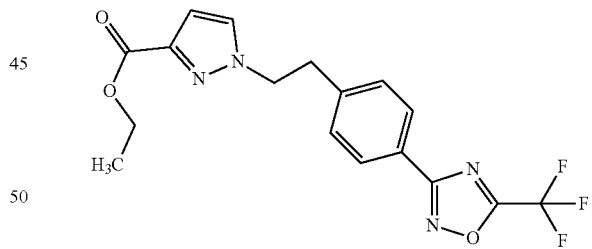

3-[4-(2-Bromoethyl)phenyl]-5-(trifluoromethyl)-1,2,4-oxadiazole (0.150 g, 0.467 mmol) and ethyl 1H-pyrazole-4-carboxylate (0.03 g, 0.08 mmol) were suspended in acetonitrile (1 mL) and potassium carbonate (0.30 g, 0.934 mmol) was introduced and the mixture was stirred for 16 hours. Then the reaction mixture was diluted with water (20 mL) and extracted with ethyl acetate. The total combined organic layer was washed with water and brine solution. The organic layer thus obtained was dried over anhydrous $Na_2SO_4$, filtered and concentrated under reduced pressure. The resultant crude residue was purified by flash chromatography over silica gel using 30% ethyl acetate in hexane as eluent to afford pure ethyl 1-[2-[4-[5-(trifluoromethyl)-1,2,4-oxadiazol-3-yl]phenyl]ethyl]pyrazole-4-carboxylate (0.03 g, 20% yield) as a white solid. MP: 108-110° C. LC/MS (Method C) retention time=1.57 minutes, 381 (M+H).

¹H NMR (400 MHz, CDCl₃) δ ppm: 8.05 (m, 2H), 7.96 (s, 1H), 7.69 (s, 1H), 7.23 (m, 2H), 4.41 (t, 2H), 4.28 (q, 2H) 3.30 (t, 2H), 1.33 (m, 3H).

The following general procedure was performed in a combinatorial fashion using appropriate building blocks (compounds of Formulae (II) and (III)) to provide the compounds of Formula (I). The compounds prepared via the following combinatorial protocol were analyzed using LC/MS Method B.

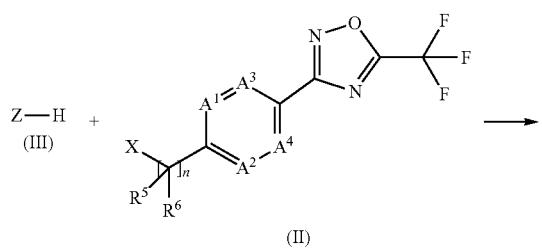

(II)

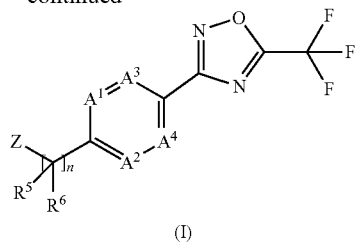

(I)

By way of exemplification, 3-[4-(bromomethyl)phenyl]-5-(trifluoromethyl)-1,2,4-oxadiazole (0.03 mmol in 1000 μL acetonitrile) were transferred to microwave vials containing amine derivative of formula (II) (0.03 mmol), potassium carbonate (0.06 mmol), and were stirred under microwaves irradiation at 120° C. for 20 minutes in the parallel microwave apparatus. The solvent was removed under a stream of nitrogen. The resultant crude residues were solubilized in a mixture of MeOH (250 μL) and DMA (500 μL) and directly submitted for preparative LC/MS purification which provided the compounds of formula (I). Structures of Isomers were assigned by NMR techniques.

TABLE T1

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.1 | 3-[4-[[4-(1-ethyl-3-methyl-pyrazol-4-yl)triazol-1-yl]methyl]phenyl]-5-(trifluoromethyl)-1,2,4-oxadiazole | 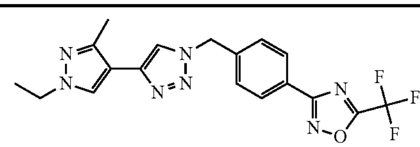 | | | | 116.2-118.2 |
| 1.2 | 3-[4-[[4-(1-ethyl-5-methyl-pyrazol-4-yl)triazol-1-yl]methyl]phenyl]-5-(trifluoromethyl)-1,2,4-oxadiazole | 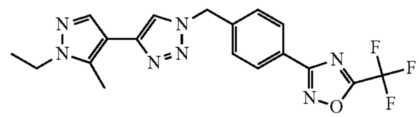 [SMILES: CCn1ncc(-c2cn(Cc3ccc(-c4noc(C(F)(F)F)n4)cc3)nn2)c1C] | | | | 138.3-140.1 |
| 1.3 | 3-[4-[(5-phenyltriazol-1-yl)methyl]phenyl]-5-(trifluoromethyl)-1,2,4-oxadiazole | 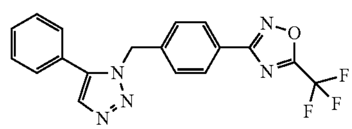 [SMILES: FC(F)(F)c1nc(-c2ccc(Cn3nncc3-c3ccccc3)cc2)no1] | 1.08 | 272.3 | A | |
| 1.4 | 3-[4-[(4-phenyltriazol-1-yl)methyl]phenyl]-5-(trifluoromethyl)-1,2,4-oxadiazole | 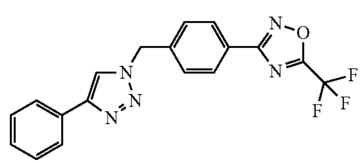 [SMILES: FC(F)(F)c1nc(-c2ccc(Cn3cc(-c4ccccc4)nn3)cc2)no1] | | | | 161.5-164.4 |
| 1.5 | 3-[4-[(4-cyclopropyltriazol-1-yl)methyl]phenyl]-5-(trifluoromethyl)-1,2,4-oxadiazole | 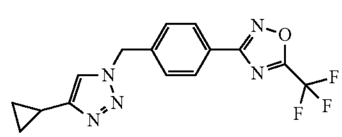 [SMILES: FC(F)(F)c1nc(-c2ccc(Cn3cc(C4CC4)nn3)cc2)no1] | | | | 115.5-117.2 |
| 1.6 | 3-[4-[[4-(3-methylimidazol-4-yl)triazol-1-yl]methyl]phenyl]-5-(trifluoromethyl)-1,2,4-oxadiazole | 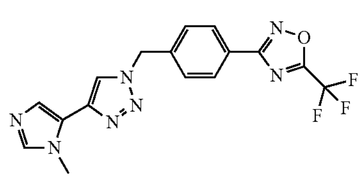 [SMILES: Cn1cncc1-c1cn(Cc2ccc(-c3noc(C(F)(F)F)n3)cc2)nn1] | | | | 108.7-110.3 |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.7 | [1-[[4-[5-(trifluoromethyl)-1,2,4-oxadiazol-3-yl]phenyl]methyl]triazol-4-yl]methyl acetate | 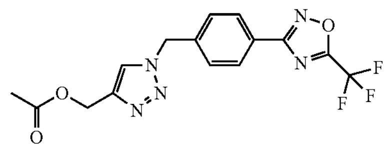 [SMILES: CC(=O)OCc1cn(Cc2ccc(-c3noc(C(F)(F)F)n3)cc2)nn1] | | | | 157.4-160.4 |
| 1.8 | 3-[4-[[4-(3-thienyl)triazol-1-yl]methyl]phenyl]-5-(trifluoromethyl)-1,2,4-oxadiazole | 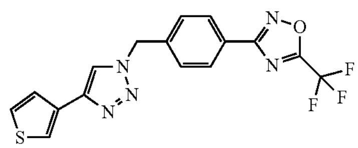 [SMILES: FC(F)(F)c1nc(-c2ccc(Cn3cc(-c4ccsc4)nn3)cc2)no1] | | | | 160.2-163.9 |
| 1.9 | tert-butyl N-[[1-[[4-[5-(trifluoromethyl)-1,2,4-oxadiazol-3-yl]phenyl]methyl]triazol-4-yl]methyl]carbamate | 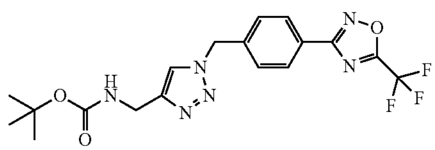 [SMILES: CC(C)(C)OC(=O)NCc1cn(Cc2ccc(-c3noc(C(F)(F)F)n3)cc2)nn1] | | | | 134.7-136.9 |
| 1.10 | 3-[4-[(5,5-dimethyl-4H-oxazol-2-yl)methyl]phenyl]-5-(trifluoromethyl)-1,2,4-oxadiazole | 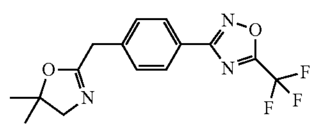 [SMILES: CC1(C)CN=C(Cc2ccc(-c3noc(C(F)(F)F)n3)cc2)O1] | 1.71 | 326.2 | A | |
| 1.11 | 3-[4-[[4-(ethoxymethyl)triazol-1-yl]methyl]phenyl]-5-(trifluoromethyl)-1,2,4-oxadiazole | 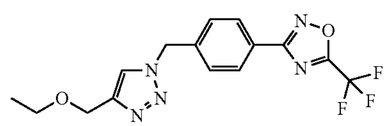 [SMILES: CCOCc1cn(Cc2ccc(-c3noc(C(F)(F)F)n3)cc2)nn1] | | | | 115.7-117.6 |
| 1.12 | 3-[4-[[4-(4-methoxyphenyl)triazol-1-yl]methyl]phenyl]-5-(trifluoromethyl)-1,2,4-oxadiazole | 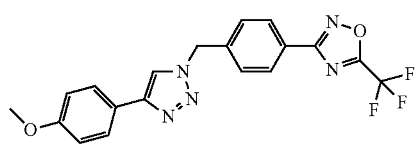 [SMILES: COc1ccc(-c2cn(Cc3ccc(-c4noc(C(F)(F)F)n4)cc3)nn2)cc1] | | | | 187.7-196.2 |
| 1.13 | 3-[4-[[4-(4-fluorophenyl)triazol-1-yl]methyl]phenyl]-5-(trifluoromethyl)-1,2,4-oxadiazole | 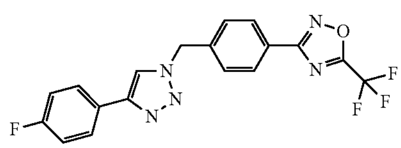 [SMILES: Fc1ccc(C2=CN(Cc3ccc(-c4noc(C(F)(F)F)n4)cc3)NN2)cc1] | | | | 185.3-189 |
| 1.14 | 3-[4-[[4-(p-tolyl)triazol-1-yl]methyl]phenyl]-5-(trifluoromethyl)-1,2,4-oxadiazole | 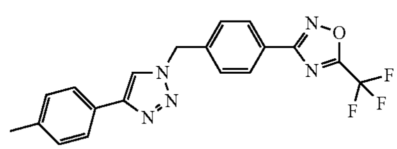 [SMILES: Cc1ccc(-c2cn(Cc3ccc(-c4noc(C(F)(F)F)n4)cc3)nn2)cc1] | | | | 200.6-204.2 |
| 1.15 | 3-[4-[(3,5-dimethylpyrazol-1-yl)methyl]phenyl]-5-(trifluoromethyl)-1,2,4-oxadiazole | 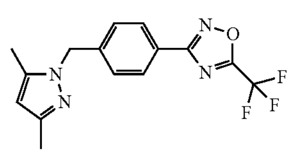 [SMILES: Cc1cc(C)n(Cc2ccc(-c3noc(C(F)(F)F)n3)cc2)n1] | | | | 53-58 |
| 1.16 | 3-[4-(pyrazol-1-ylmethyl)phenyl]-5-(trifluoromethyl)-1,2,4-oxadiazole | 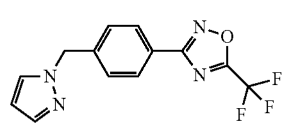 [SMILES: FC(F)(F)c1nc(-c2ccc(Cn3cccn3)cc2)no1] | | | | 36-41 |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.17 | 3-[4-[[3,5-bis(difluoromethyl)pyrazol-1-yl]methyl]phenyl]-5-(trifluoromethyl)-1,2,4-oxadiazole | 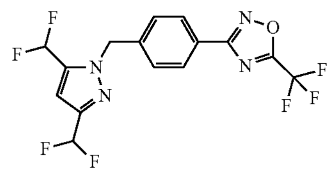 [SMILES: FC(F)c1cc(C(F)F)n(Cc2ccc(-c3noc(C(F)(F)F)n3)cc2)n1] | | | | 53-58 |
| 1.18 | 3-[4-(imidazol-1-ylmethyl)phenyl]-5-(trifluoromethyl)-1,2,4-oxadiazole | 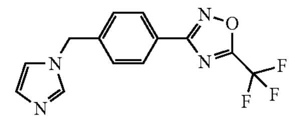 | | | | 45-55 |
| 1.19 | 3-[4-(1,2,4-triazol-1-ylmethyl)phenyl]-5-(trifluoromethyl)-1,2,4-oxadiazole | 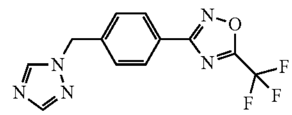 [SMILES: FC(F)(F)c1nc(-c2ccc(Cn3cncn3)cc2)no1] | 1.30 | 296.1 | B | 72-77 |
| 1.20 | 3-[4-[[5-methyl-3-(trifluoromethyl)pyrazol-1-yl]methyl]phenyl]-5-(trifluoromethyl)-1,2,4-oxadiazole | 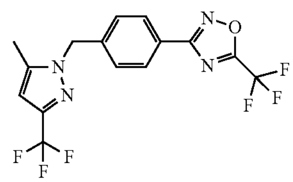 [SMILES: Cc1cc(C(F)(F)F)nn1Cc1ccc(-c2noc(C(F)(F)F)n2)cc1] | 1.17 | 377.4 | A | |
| 1.21 | 5-(trifluoromethyl)-3-[4-[[3-(trifluoromethyl)pyrazol-1-yl]methyl]phenyl]-1,2,4-oxadiazole | 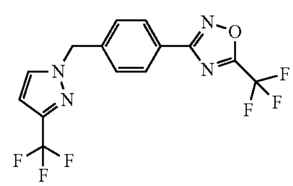 [SMILES: FC(F)(F)c1ccn(Cc2ccc(-c3noc(C(F)(F)F)n3)cc2)n1] | 1.14 | 363.2 | A | |
| 1.22 | 3-[4-[[4-(2-pyridyl)triazol-1-yl]methyl]phenyl]-5-(trifluoromethyl)-1,2,4-oxadiazole | 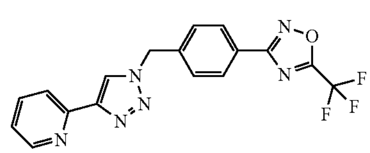 [SMILES: FC(F)(F)c1nc(-c2ccc(Cn3cc(-c4ccccn4)nn3)cc2)no1] | | | | 160.2-162.4 |
| 1.23 | 3-[4-[[4-(3-pyridyl)triazol-1-yl]methyl]phenyl]-5-(trifluoromethyl)-1,2,4-oxadiazole | 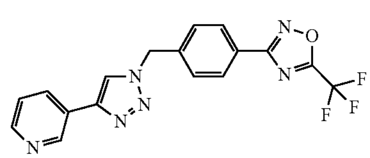 [SMILES: FC(F)(F)c1nc(-c2ccc(Cn3cc(-c4cccnc4)nn3)cc2)no1] | | | | 159.8-163.1 |
| 1.24 | 3-[4-[(4-cyclopentyltriazol-1-yl)methyl]phenyl]-5-(trifluoromethyl)-1,2,4-oxadiazole | 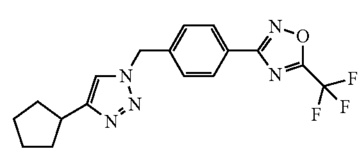 [SMILES: FC(F)(F)c1nc(-c2ccc(Cn3cc(C4CCCC4)nn3)cc2)no1] | | | | 117.9-118.8 |
| 1.25 | trimethyl-[1-[[4-[5-(trifluoromethyl)-1,2,4-oxadiazol-3-yl]phenyl]methyl]triazol-4-yl]silane | 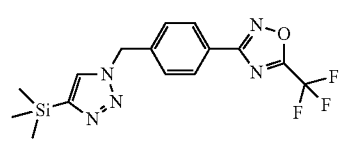 [SMILES: C[Si](C)(C)c1cn(Cc2ccc(-c3noc(C(F)(F)F)n3)cc2)nn1] | | | | 87.8-89.5 |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.26 | 3-[4-[(4-isobutyltriazol-1-yl)methyl]phenyl]-5-(trifluoromethyl)-1,2,4-oxadiazole | 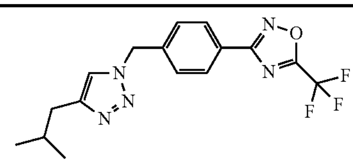 | | | | 113.9-115.7 |
| 1.27 | 3-[4-[(4-tert-butyltriazol-1-yl)methyl]phenyl]-5-(trifluoromethyl)-1,2,4-oxadiazole | 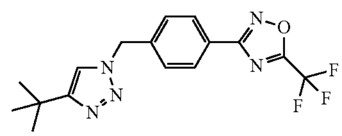 [SMILES: CC(C)(C)c1cn(Cc2ccc(-c3noc(C(F)(F)F)n3)cc2)nn1] | | | | 90.4-92.3 |
| 1.28 | 3-[4-[[4-(phenoxymethyl)triazol-1-yl]methyl]phenyl]-5-(trifluoromethyl)-1,2,4-oxadiazole | 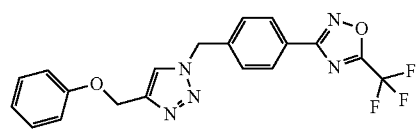 [SMILES: FC(F)(F)c1nc(-c2ccc(Cn3cc(COc4ccccc4)nn3)cc2)no1] | | | | 103.2-104.9 |
| 1.29 | 3-[4-[[4-[(5-chloro-3-methoxy-2-pyridyl)oxymethyl]triazol-1-yl]methyl]phenyl]-5-(trifluoromethyl)-1,2,4-oxadiazole | 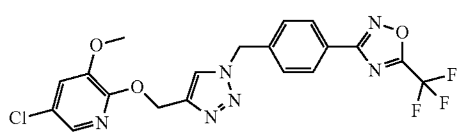 [SMILES: COc1cc(Cl)cnc1OCc1cn(Cc2ccc(-c3noc(C(F)(F)F)n3)cc2)nn1] | | | | 109.9-113.3 |
| 1.30 | N-[1-methyl-1-[1-[[4-[5-(trifluoromethyl)-1,2,4-oxadiazol-3-yl]phenyl]methyl]triazol-4-yl]ethyl]benzamide | 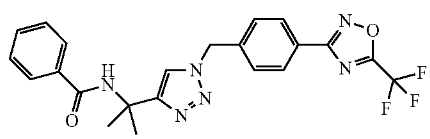 [SMILES: CC(C)(NC(=O)c1ccccc1)c1cn(Cc2ccc(-c3noc(C(F)(F)F)n3)cc2)nn1] | | | | 157.6-161.9 |
| 1.31 | 3-[4-[[4-[1-(2,6-diethylphenyl)-5-methyl-pyrazol-4-yl]triazol-1-yl]methyl]phenyl]-5-(trifluoromethyl)-1,2,4-oxadiazole | 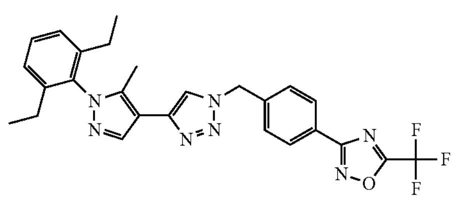 [SMILES: CCc1cccc(CC)c1-n1ncc(-c2cn(Cc3ccc(-c4noc(C(F)(F)F)n4)cc3)nn2)c1C] | | | | 157.6-161.9 |
| 1.32 | 3-[4-(triazol-1-ylmethyl)phenyl]-5-(trifluoromethyl)-1,2,4-oxadiazole | 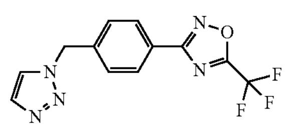 [SMILES: FC(F)(F)c1nc(-c2ccc(Cn3ccnn3)cc2)no1] | 1.33 | 296.1 | B | 107.6-109.5 |
| 1.33 | 3-[4-(triazol-2-ylmethyl)phenyl]-5-(trifluoromethyl)-1,2,4-oxadiazole | 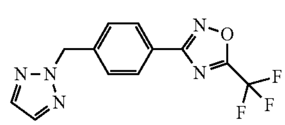 [SMILES: FC(F)(F)c1nc(-c2ccc(Cn3nccn3)cc2)no1] | | | | 105.4-107.9 |
| 1.34 | 3-[4-(benzotriazol-2-ylmethyl)phenyl]-5-(trifluoromethyl)-1,2,4-oxadiazole | 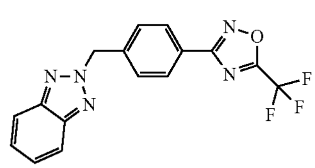 [SMILES: FC(F)(F)c1nc(-c2ccc(Cn3nc4ccccc4n3)cc2)no1] | 1.85 | 346.1 | B | 112.4-116.6 |
| 1.35 | 3-[4-(benzotriazol-1-ylmethyl)phenyl]-5-(trifluoromethyl)-1,2,4-oxadiazole | 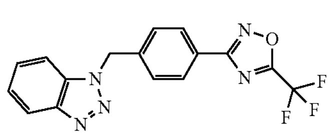 [SMILES: FC(F)(F)c1nc(-c2ccc(Cn3nnc4ccccc43)cc2)no1] | 1.67 | 346.1 | B | 142.3-143.2 |

TABLE T1-continued

Melting point (mp) and/or LC/MS data (retention time (t_R)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.36 | methyl 2-[[4-[5-(trifluoromethyl)-1,2,4-oxadiazol-3-yl]phenyl]methyl]-1,2,4-triazole-3-carboxylate | 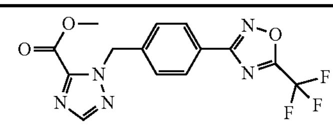 | 1.50 | 354.1 | B | 122.8-124.4 |
| 1.37 | methyl 1-[[4-[5-(trifluoromethyl)-1,2,4-oxadiazol-3-yl]phenyl]methyl]-1,2,4-triazole-3-carboxylate | 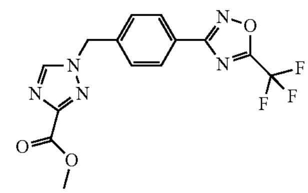 [SMILES: COC(=O)c1ncn(Cc2ccc(-c3noc(C(F)(F)F)n3)cc2)n1] | 1.35 | 354.1 | B | 174-177.2 |
| 1.38 | 5-(trifluoromethyl)-3-[4-[[5-(trifluoromethyl)-1,2,4-triazol-1-yl]methyl]phenyl]-1,2,4-oxadiazole | 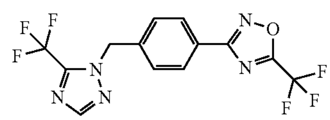 [SMILES: FC(F)(F)c1nc(-c2ccc(Cn3ncnc3C(F)(F)F)cc2)no1] | 1.09 | 405.2 | A | |
| 1.39 | 5-(trifluoromethyl)-3-(trifluoromethyl)-1,2,4-triazol-1-yl]methyl]phenyl]-1,2,4-oxadiazole | 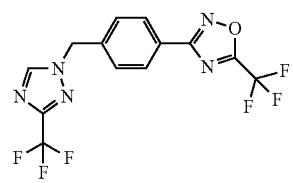 | 1.69 | 364.1 | B | 68.2-70.1 |
| 1.40 | 1-[[4-[5-(trifluoromethyl)-1,2,4-oxadiazol-3-yl]phenyl]methyl]-1,2,4-triazole-3-carbonitrile | 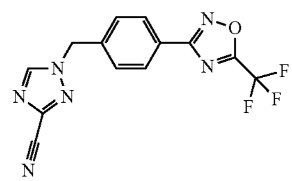 [SMILES: N#Cc1ncn(Cc2ccc(-c3noc(C(F)(F)F)n3)cc2)n1] | 1.56 | 321.1 | B | |
| 1.41 | 2-[[4-[5-(trifluoromethyl)-1,2,4-oxadiazol-3-yl]phenyl]methyl]-1,2,4-triazole-3-carbonitrile | 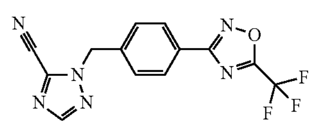 [SMILES: N#Cc1ncnn1Cc1ccc(-c2noc(C(F)(F)F)n2)cc1] | | | | 120-124 |
| 1.42 | 3-[4-[1-(6-methoxy-3-pyridyl)ethyl]phenyl]-5-(trifluoromethyl)-1,2,4-oxadiazole | 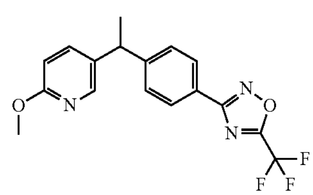 [SMILES: COc1ccc(C(C)c2ccc(-c3noc(C(F)(F)F)n3)cc2)cn1] | 1.26 | 350 | A | |
| 1.43 | dimethyl 1-[[4-[5-(trifluoromethyl)-1,2,4-oxadiazol-3-yl]phenyl]methyl] imidazole-4,5-dicarboxylate | 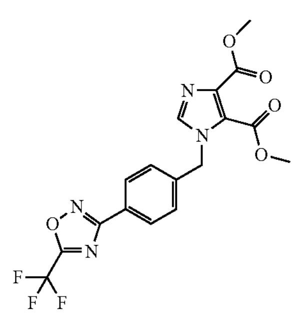 [SMILES: COC(=O)c1ncn(Cc2ccc(-c3noc(C(F)(F)F)n3)cc2)c1C(=O)OC] | 1.48 | 411.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.44 | 3-[4-[(4-iodopyrazol-1-yl)methyl]phenyl]-5-(trifluoromethyl)-1,2,4-oxadiazole | 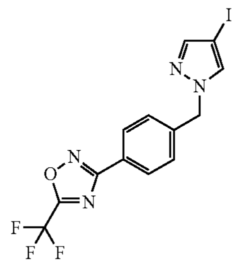 [SMILES: FC(F)(F)c1nc(-c2ccc(Cn3cc(I)cn3)cc2)no1] | 1.83 | 421.1 | B | |
| 1.45 | 1-[[4-[5-(trifluoromethyl)-1,2,4-oxadiazol-3-yl]phenyl]methyl]imidazole-4,5-dicarbonitrile | 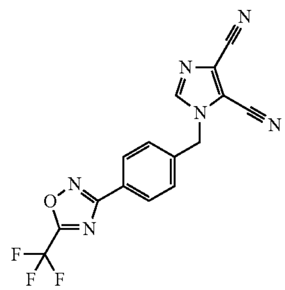 [SMILES: N#Cc1ncn(Cc2ccc(-c3noc(C(F)(F)F)n3)cc2)c1C#N] | 1.59 | 345.2 | B | |
| 1.46 | 3-[4-[(4,5-dichloroimidazol-1-yl)methyl]phenyl]-5-(trifluoromethyl)-1,2,4-oxadiazole | 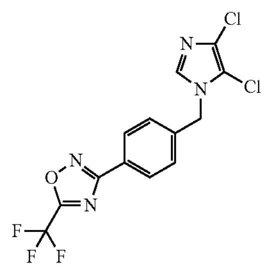 [SMILES: FC(F)(F)c1nc(-c2ccc(Cn3cnc(Cl)c3Cl)cc2)no1] | 1.76 | 363.1 | B | |
| 1.47 | 3-[4-[(2-phenylimidazol-1-yl)methyl]phenyl]-5-(trifluoromethyl)-1,2,4-oxadiazole | 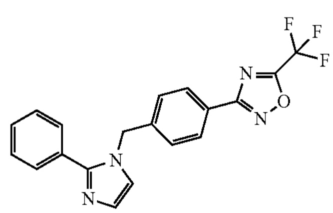 [SMILES: FC(F)(F)c1nc(-c2ccc(Cn3ccnc3-c3ccccc3)cc2)no1] | 1.14 | 371.2 | B | |
| 1.48 | 5-(trifluoromethyl)-3-[4-[[2-(trifluoromethyl)benzimidazol-1-yl]methyl]phenyl]-1,2,4-oxadiazole | 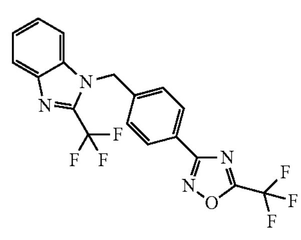 [SMILES: FC(F)(F)c1nc(-c2ccc(Cn3c(C(F)(F)F)nc4ccccc43)cc2)no1] | 1.93 | 413.2 | B | |
| 1.49 | 3-[4-[(2-bromoimidazol-1-yl)methyl]phenyl]-5-(trifluoromethyl)-1,2,4-oxadiazole | 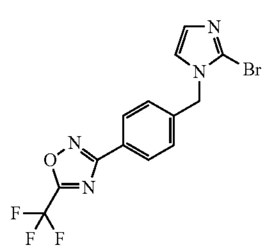 [SMILES: FC(F)(F)c1nc(-c2ccc(Cn3ccnc3Br)cc2)no1] | 1.54 | 373.1 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.50 | 1-[1-[[4-[5-(trifluoromethyl)-1,2,4-oxadiazol-3-yl]phenyl]methyl]indol-3-yl]ethanone | 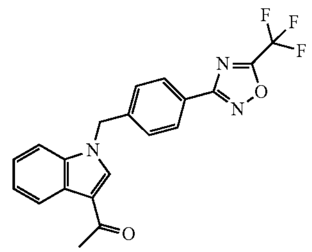 [SMILES: CC(=O)c1cn(Cc2ccc(-c3noc(C(F)(F)F)n3)cc2)c2ccccc12] | 1.80 | 386.2 | B | |
| 1.51 | 6-methyl-1-[[4-[5-(trifluoromethyl)-1,2,4-oxadiazol-3-yl]phenyl]methyl]indole-3-carbaldehyde | 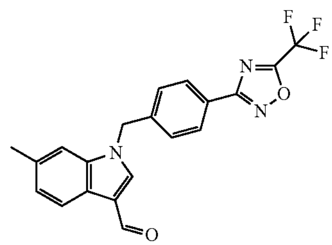 [SMILES: Cc1ccc2c(C=O)cn(Cc3ccc(-c4noc(C(F)(F)F)n4)cc3)c2c1] | 1.85 | 386.2 | B | |
| 1.52 | 3-[4-[(5-methylindol-1-yl)methyl]phenyl]-5-(trifluoromethyl)-1,2,4-oxadiazole | 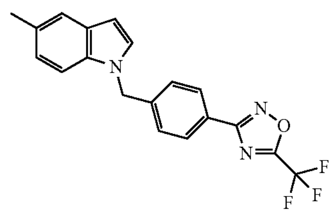 [SMILES: Cc1ccc2c(ccn2Cc2ccc(-c3noc(C(F)(F)F)n3)cc2)c1] | 2.05 | 358.2 | B | |
| 1.53 | 3-[4-[(2-methylimidazol-1-yl)methyl]phenyl]-5-(trifluoromethyl)-1,2,4-oxadiazole | 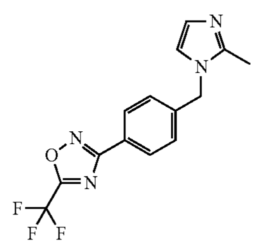 [SMILES: Cc1nccn1Cc1ccc(-c2noc(C(F)(F)F)n2)cc1] | 0.91 | 309.2 | B | |
| 1.54 | 3-[4-[(6-fluoroindol-1-yl)methyl]phenyl]-5-(trifluoromethyl)-1,2,4-oxadiazole | 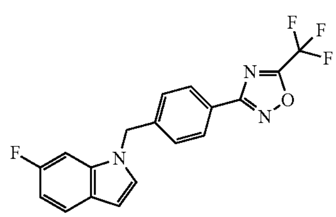 [SMILES: Fc1ccc2ccn(Cc3ccc(-c4noc(C(F)(F)F)n4)cc3)c2c1] | 2.05 | 362.2 | B | |
| 1.55 | 5-(trifluoromethyl)-3-[4-[[4-(trifluoromethyl)pyrazol-1-yl]methyl]phenyl]-1,2,4-oxadiazole | 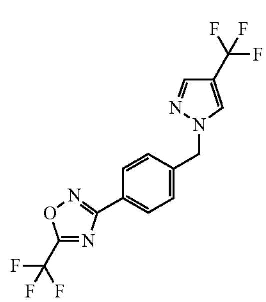 [SMILES: FC(F)(F)c1cnn(Cc2ccc(-c3noc(C(F)(F)F)n3)cc2)c1] | 1.84 | 363.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.56 | 3-[4-[(2-isopropylimidazol-1-yl)methyl]phenyl]-5-(trifluoromethyl)-1,2,4-oxadiazole | 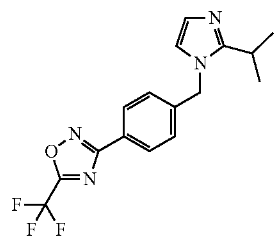 [SMILES: CC(C)c1nccn1Cc1ccc(-c2noc(C(F)(F)F)n2)cc1] | 1.03 | 337.2 | B | |
| 1.57 | 5-methoxy-1-[[4-[5-(trifluoromethyl)-1,2,4-oxadiazol-3-yl]phenyl]methyl]indole-3-carbaldehyde | 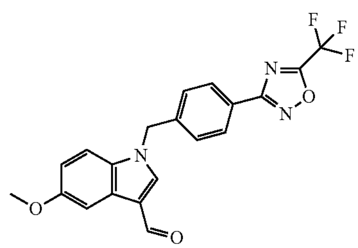 [SMILES: COc1ccc2c(c1)c(C=O)cn2Cc1ccc(-c2noc(C(F)(F)F)n2)cc1] | 1.75 | 402.2 | B | |
| 1.58 | 2-[1-[[4-[5-(trifluoromethyl)-1,2,4-oxadiazol-3-yl]phenyl]methyl]benzimidazol-2-yl]acetonitrile | 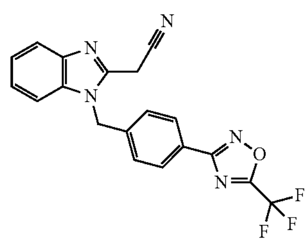 [SMILES: N#CCc1nc2ccccc2n1Cc1ccc(-c2noc(C(F)(F)F)n2)cc1] | 1.61 | 384.2 | B | |
| 1.59 | 1-[1-[[4-[5-(trifluoromethyl)-1,2,4-oxadiazol-3-yl]phenyl]methyl]pyrrol-2-yl]ethanone | 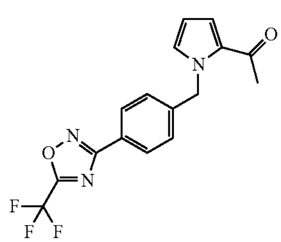 [SMILES: CC(=O)c1cccn1Cc1ccc(-c2noc(C(F)(F)F)n2)cc1] | 1.80 | 336.2 | B | |
| 1.60 | 1-[[4-[5-(trifluoromethyl)-1,2,4-oxadiazol-3-yl]phenyl]methyl]pyrrole-3-carbonitrile | 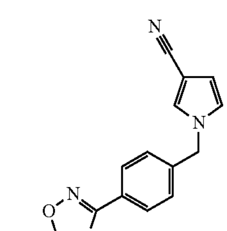 | 1.70 | 319.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.61 | ethyl 1-[[4-[5-(trifluoromethyl)-1,2,4-oxadiazol-3-yl]phenyl]methyl]pyrazole-4-carboxylate | 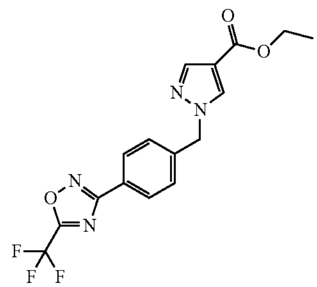 [SMILES: CCOC(=O)c1cnn(Cc2ccc(-c3noc(C(F)(F)F)n3)cc2)c1] | 1.71 | 367.2 | B | 120-130 |
| 1.62 | 1-[[4-[5-(trifluoromethyl)-1,2,4-oxadiazol-3-yl]phenyl]methyl]pyrrole-2-carbaldehyde | 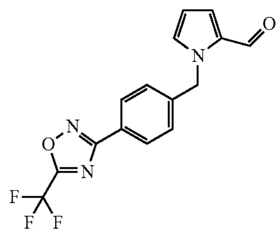 | 1.73 | 322.2 | B | |
| 1.63 | 3-[4-[(2-ethylbenzimidazol-1-yl)methyl]phenyl]-5-(trifluoromethyl)-1,2,4-oxadiazole | 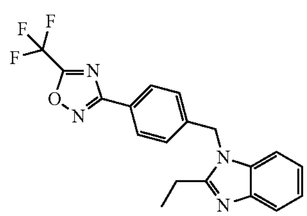 [SMILES: CCc1nc2ccccc2n1Cc1ccc(-c2noc(C(F)(F)F)n2)cc1] | 1.24 | 373.2 | B | |
| 1.64 | 3-[4-[(6-chloroindol-1-yl)methyl]phenyl]-5-(trifluoromethyl)-1,2,4-oxadiazole | 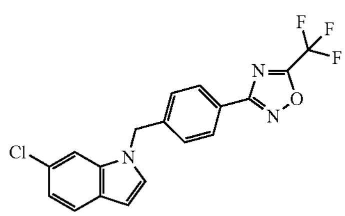 [SMILES: FC(F)(F)c1nc(-c2ccc(Cn3ccc4ccc(Cl)cc43)cc2)no1] | 2.14 | 378.2 | B | |
| 1.65 | 3-[4-[[2-(4-fluorophenyl)imidazol-1-yl]methyl]phenyl]-5-(trifluoromethyl)-1,2,4-oxadiazole | 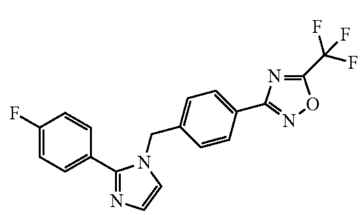 [SMILES: Fc1ccc(-c2nccn2Cc2ccc(-c3noc(C(F)(F)F)n3)cc2)cc1] | 1.18 | 389.2 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.66 | methyl 1-[[4-[5-(trifluoromethyl)-1,2,4-oxadiazol-3-yl]phenyl]methyl]indole-4-carboxylate | 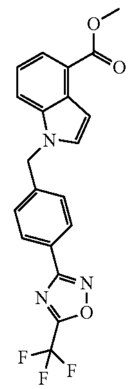 [SMILES: COC(=O)c1cccc2c1ccn2Cc1ccc(-c2noc(C(F)(F)F)n2)cc1] | 1.98 | 402.2 | B | |
| 1.67 | 3-[4-[(4-chloropyrazol-1-yl)methyl]phenyl]-5-(trifluoromethyl)-1,2,4-oxadiazole | 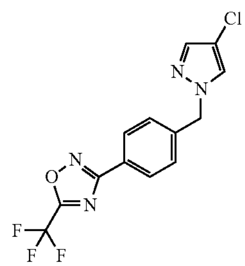 | 1.77 | 329.2 | B | |
| 1.68 | methyl 2-methyl-5-(trifluoromethyl)-1-[[4-[5-(trifluoromethyl)-1,2,4-oxadiazol-3-yl]phenyl]methyl]pyrrole-3-carboxylate | 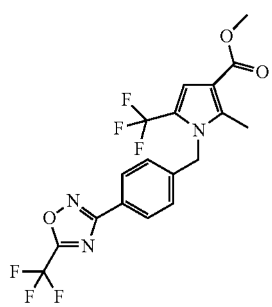 [SMILES: COC(=O)c1cc(C(F)(F)F)n(Cc2ccc(-c3noc(C(F)(F)F)n3)cc2)c1C] | 1.96 | 434.4 | B | |
| 1.69 | 3-[4-[(2,4,5-tribromoimidazol-1-yl)methyl]phenyl]-5-(trifluoromethyl)-1,2,4-oxadiazole | 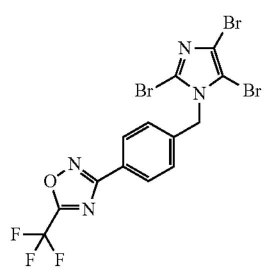 [SMILES: FC(F)(F)c1nc(-c2ccc(Cn3c(Br)nc(Br)c3Br)cc2)no1] | 1.98 | 528.5 | B | |
| 1.70 | 2-methyl-1-[[4-[5-(trifluoromethyl)-1,2,4-oxadiazol-3-yl]phenyl]methyl]indole-3-carbaldehyde | 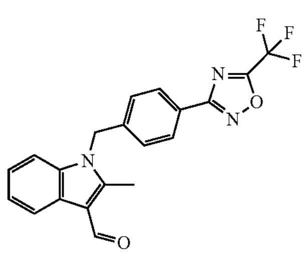 [SMILES: Cc1c(C=O)c2ccccc2n1Cc1ccc(-c2noc(C(F)(F)F)n2)cc1] | 1.81 | 386.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.71 | 1-[[4-[5-(trifluoromethyl)-1,2,4-oxadiazol-3-yl]phenyl]methyl]imidazole-2-carbaldehyde | 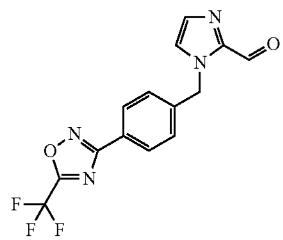 [SMILES: O=Cc1nccn1Cc1ccc(-c2noc(C(F)(F)F)n2)cc1] | 1.46 | 323.2 | B | |
| 1.72 | 3-[4-[(2-bromo-4,5-dichloro-imidazol-1-yl)methyl]phenyl]-5-(trifluoromethyl)-1,2,4-oxadiazole | 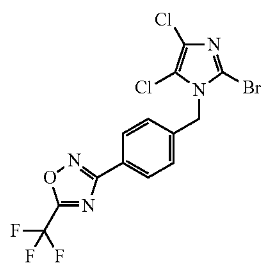 [SMILES: FC(F)(F)c1nc(-c2ccc(Cn3c(Br)nc(Cl)c3Cl)cc2)no1] | 1.97 | 441.0 | B | |
| 1.73 | 3-[4-[[2-(4-pyridyl)benzimidazol-1-yl]methyl]phenyl]-5-(trifluoromethyl)-1,2,4-oxadiazole | 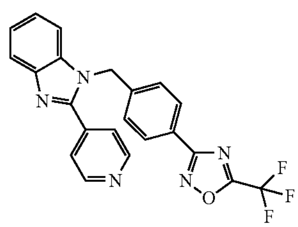 [SMILES: FC(F)(F)c1nc(-c2ccc(Cn3c(-c4ccncc4)nc4ccccc43)cc2)no1] | 1.59 | 422.3 | B | |
| 1.74 | 2-[[4-[5-(trifluoromethyl)-1,2,4-oxadiazol-3-yl]phenyl]methyl]-5,6-dihydrocyclopenta[c]pyrrol-4-one | 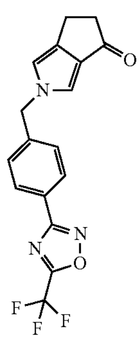 [SMILES: O=C1CCc2cn(Cc3ccc(-c4noc(C(F)(F)F)n4)cc3)cc21] | 1.61 | 348.2 | B | |
| 1.75 | 3-[4-[(5-methoxyindol-1-yl)methyl]phenyl]-5-(trifluoromethyl)-1,2,4-oxadiazole | 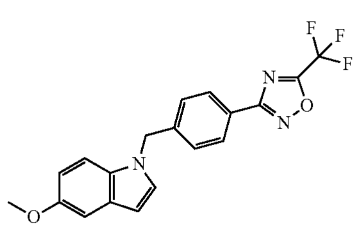 [SMILES: COc1ccc2c(ccn2Cc2ccc(-c3noc(C(F)(F)F)n3)cc2)c1] | 1.91 | 374.2 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.76 | 1-[[4-[5-(trifluoromethyl)-1,2,4-oxadiazol-3-yl]phenyl]methyl]pyrazole-4-carbonitrile | 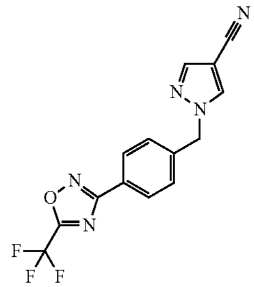 [SMILES: N#Cc1cnn(Cc2ccc(-c3noc(C(F)(F)F)n3)cc2)c1] | 1.57 | 320.2 | B | |
| 1.77 | 3-[4-[(4-bromopyrazol-1-yl)methyl]phenyl]-5-(trifluoromethyl)-1,2,4-oxadiazole | 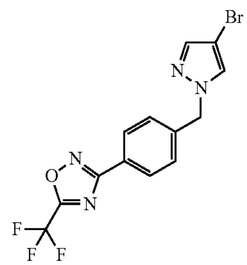 [SMILES: FC(F)(F)c1nc(-c2ccc(Cn3cc(Br)cn3)cc2)no1] | 1.80 | 373.1 | B | |
| 1.78 | 3-[4-[(2,4-dimethylimidazol-1-yl)methyl]phenyl]-5-(trifluoromethyl)-1,2,4-oxadiazole | 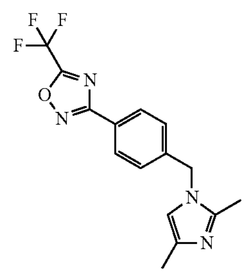 [SMILES: Cc1cn(Cc2ccc(-c3noc(C(F)(F)F)n3)cc2)c(C)n1] | 0.92 | 323.1 | B | |
| 1.79 | 3-[4-[(4-bromoimidazol-1-yl)methyl]phenyl]-5-(trifluoromethyl)-1,2,4-oxadiazole | 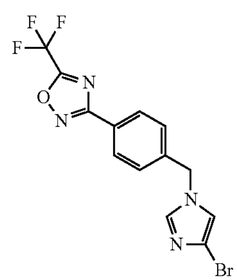 [SMILES: FC(F)(F)c1nc(-c2ccc(Cn3cnc(Br)c3)cc2)no1] | 1.55 | 373.0 | B | |
| 1.80 | ethyl 5-methyl-3-[[4-[5-(trifluoromethyl)-1,2,4-oxadiazol-3-yl]phenyl]methyl]imidazole-4-carboxylate | 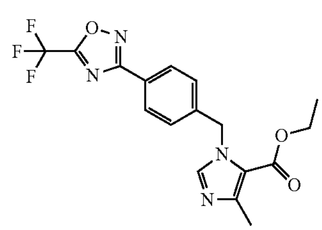 [SMILES: CCOC(=O)c1c(C)ncn1Cc1ccc(-c2noc(C(F)(F)F)n2)cc1] | 1.47 | 381.2 | B | |
| 1.81 | 1,3-dimethyl-7-[[4-[5-(trifluoromethyl)-1,2,4-oxadiazol-3-yl]phenyl]methyl]purine-2,6-dione | 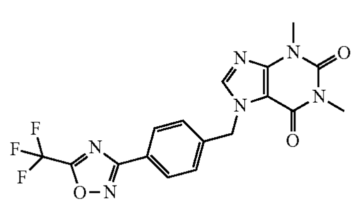 [SMILES: Cn1c(=O)c2c(ncn2Cc2ccc(-c3noc(C(F)(F)F)n3)cc2)n(C)c1=O] | 1.43 | 407.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.82 | 3-[4-[(4-phenylimidazol-1-yl)methyl]phenyl]-5-(trifluoromethyl)-1,2,4-oxadiazole | 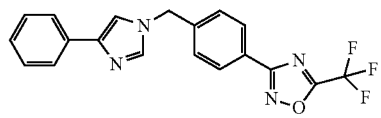 [SMILES: FC(F)(F)c1nc(-c2ccc(Cn3cnc(-c4ccccc4)c3)cc2)no1] | 1.26 | 371.2 | B | |
| 1.83 | 3-[4-[(4-methylimidazol-1-yl)methyl]phenyl]-5-(trifluoromethyl)-1,2,4-oxadiazole | 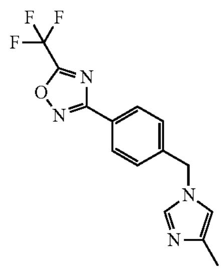 [SMILES: Cc1cn(Cc2ccc(-c3noc(C(F)(F)F)n3)cc2)cn1] | 0.88 | 309.1 | B | |
| 1.84 | ethyl 4-phenyl-1-[[4-[5-(trifluoromethyl)1,2,4-oxadiazol-3-yl]phenyl]methyl]pyrazole-3-carboxylate | 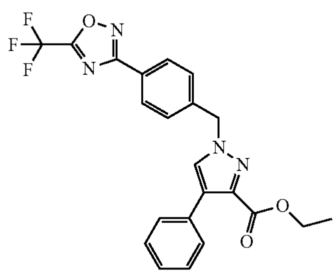 [SMILES: CCOC(=O)c1nn(Cc2ccc(-c3noc(C(F)(F)F)n3)cc2)cc1-c1ccccc1] | 1.92 | 443.2 | B | |
| 1.85 | 1-[[4-[5-(trifluoromethyl)-1,2,4-oxadiazol-3-yl]phenyl]methyl]pyrazole-3-carbaldehyde | 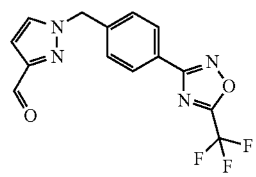 [SMILES: O=Cc1ccn(Cc2ccc(-c3noc(C(F)(F)F)n3)cc2)n1] | 1.53 | 323.1 | B | |
| 1.86 | 3-[4-(indazol-2-ylmethyl)phenyl]-5-(trifluoromethyl)-1,2,4-oxadiazole | 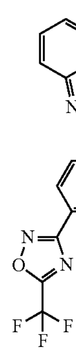 | 1.73 | 345.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.87 | 3-[4-(indazol-1-ylmethyl)phenyl]-5-(trifluoromethyl)-1,2,4-oxadiazole | 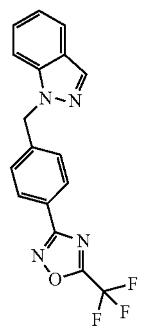 [SMILES: FC(F)(F)c1nc(-c2ccc(Cn3ncc4ccccc43)cc2)no1] | 1.86 | 345.2 | B | |
| 1.88 | methyl 1-[[4-[5-(trifluoromethyl)-1,2,4-oxadiazol-3-yl]phenyl]methyl]imidazole-4-carboxylate | 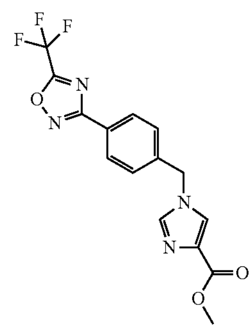 [SMILES: COC(=O)c1cn(Cc2ccc(-c3noc(C(F)(F)F)n3)cc2)cn1] | 1.34 | 353.1 | B | |
| 1.89 | methyl 3-[[4-[5-(trifluoromethyl)-1,2,4-oxadiazol-3-yl]phenyl]methyl]imidazole-4-carboxylate | 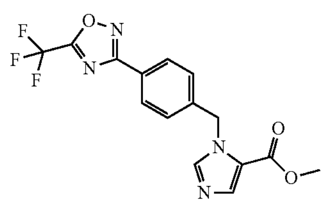 [SMILES: COC(=O)c1cncn1Cc1ccc(-c2noc(C(F)(F)F)n2)cc1] | 1.42 | 353.1 | B | |
| 1.90 | 5-(trifluoromethyl)-3-(trifluoromethyl)imidazol-1-yl]methyl]phenyl]-1,2,4-oxadiazole | 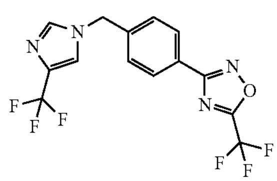 [SMILES: FC(F)(F)c1cn(Cc2ccc(-c3noc(C(F)(F)F)n3)cc2)cn1] | 1.63 | 363.1 | B | |
| 1.91 | 3-[4-[(4-bromo-2-methyl-imidazol-1-yl)methyl]phenyl]-5-(trifluoromethyl)-1,2,4-oxadiazole | 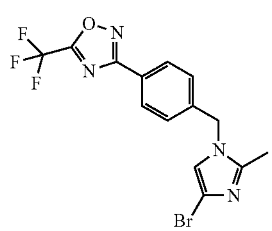 [SMILES: Cc1nc(Br)cn1Cc1ccc(-c2noc(C(F)(F)F)n2)cc1] | 1.53 | 387.0 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.92 | 3-[4-[(6-chloro-5-fluoro-benzimidazol-1-yl)methyl]phenyl]-5-(trifluoromethyl)-1,2,4-oxadiazole | 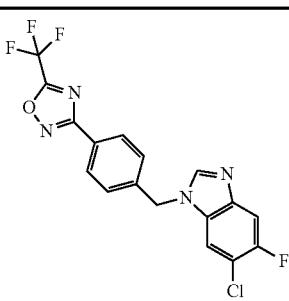 | 1.53 | 387.0 | B | |
| 1.93 | 5-methyl-1-[[4-[5-(trifluoromethyl)-1,2,4-oxadiazol-3-yl]phenyl]methyl]pyrazole-3-carbonitrile | 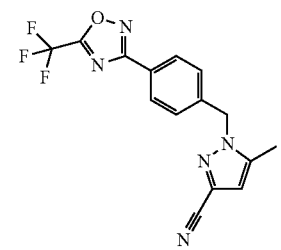 [SMILES: Cc1cc(C#N)nn1Cc1ccc(-c2noc(C(F)(F)F)n2)cc1] | 1.74 | 397.1 | B | |
| 1.94 | 3-[4-[(4-chlorobenzimidazol-1-yl)methyl]phenyl]-5-(trifluoromethyl)-1,2,4-oxadiazole | 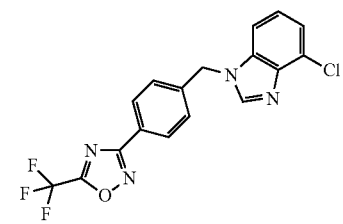 [SMILES: FC(F)(F)c1nc(-c2ccc(Cn3cnc4c(Cl)cccc43)cc2)no1] | 1.71 | 334.1 | B | |
| 1.95 | 3-[4-[(7-chlorobenzimidazol-1-yl)methyl]phenyl]-5-(trifluoromethyl)-1,2,4-oxadiazole | 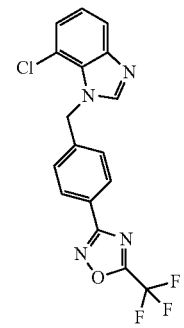 [SMILES: FC(F)(F)c1nc(-c2ccc(Cn3cnc4cccc(Cl)c43)cc2)no1] | 1.67 | 379.1 | B | |
| 1.96 | 3-[4-[(4-iodoimidazol-1-yl)methyl]phenyl]-5-(trifluoromethyl)-1,2,4-oxadiazole | 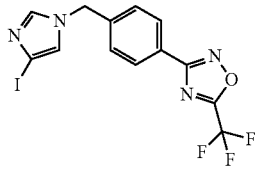 [SMILES: FC(F)(F)c1nc(-c2ccc(Cn3cnc(I)c3)cc2)no1] | 1.52 | 421.0 | B | |
| 1.97 | 3-[3-methoxy-4-(1,2,4-triazol-1-ylmethyl)phenyl]-5-(trifluoromethyl)-1,2,4-oxadiazole | 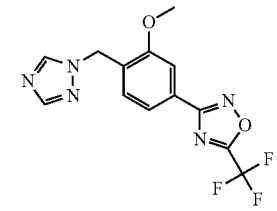 [SMILES: COc1cc(-c2noc(C(F)(F)F)n2)ccc1Cn1cncn1] | 1.38 | 325.1 | B | 102-106 |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.98 | 3-[4-(1,2,4-triazol-1-ylmethyl)-3-(trifluoromethyl)phenyl]-5-(trifluoromethyl)-1,2,4-oxadiazole | 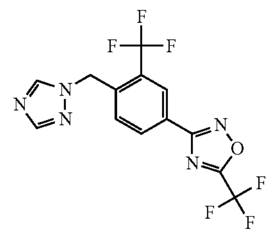 [SMILES: FC(F)(F)c1nc(-c2ccc(Cn3cncn3)c(C(F)(F)F)c2)no1] | 1.53 | 363.1 | B | |
| 1.99 | 3-[3-chloro-4-(1,2,4-triazol-1-ylmethyl)phenyl]-5-(trifluoromethyl)-1,2,4-oxadiazole | 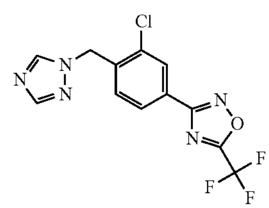 [SMILES: FC(F)(F)c1nc(-c2ccc(Cn3cncn3)c(Cl)c2)no1] | 1.44 | 329.0 | B | 63-71 |
| 1.100 | 3-[3-chloro-4-[(3,5-dimethylpyrazol-1-yl)methyl]phenyl]-5-(trifluoromethyl)-1,2,4-oxadiazole | 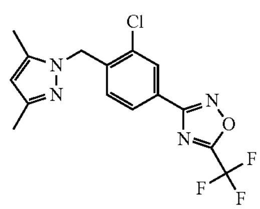 [SMILES: Cc1cc(C)n(Cc2ccc(-c3noc(C(F)(F)F)n3)cc2Cl)n1] | 1.89 | 356.1 | B | |
| 1.101 | 3-[3-fluoro-4-(1,2,4-triazol-1-ylmethyl)phenyl]-5-(trifluoromethyl)-1,2,4-oxadiazole | 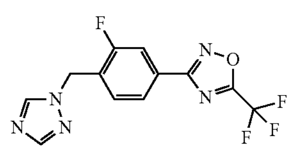 [SMILES: Fc1cc(-c2noc(C(F)(F)F)n2)ccc1Cn1cncn1] | 1.35 | 313.1 | B | 52-63 |
| 1.102 | 3-[4-[(3,5-dimethylpyrazol-1-yl)methyl]-3-fluorophenyl]-5-(trifluoromethyl)-1,2,4-oxadiazole | 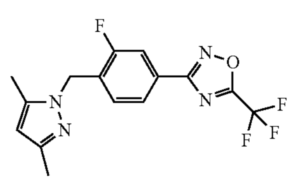 [SMILES: Cc1cc(C)n(Cc2ccc(-c3noc(C(F)(F)F)n3)cc2F)n1] | 1.89 | 356.1 | B | 50-56 |
| 1.103 | 3-[4-[(4-bromoimidazol-1-yl)methyl]-3-(trifluoromethyl)phenyl]-5-(trifluoromethyl)-1,2,4-oxadiazole | 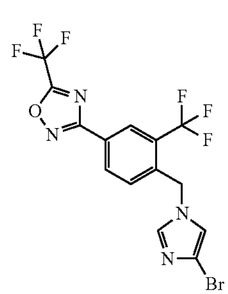 [SMILES: FC(F)(F)c1nc(-c2ccc(Cn3cnc(Br)c3)c(C(F)(F)F)c2)no1] | 1.99 | 440.0 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.104 | dimethyl 1-[[2-chloro-4-[5-(trifluoromethyl)-1,2,4-oxadiazol-3-yl]phenyl]methyl]imidazole-4,5-dicarboxylate | 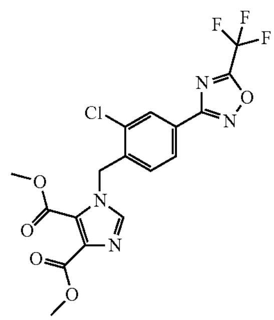 [SMILES: COC(=O)c1ncn(Cc2ccc(-c3noc(C(F)(F)F)n3)cc2Cl)c1C(=O)OC] | 1.60 | 444.0 | B | |
| 1.105 | 3-[3-chloro-4-[(2,4-dimethylimidazol-1-yl)methyl]phenyl]-5-(trifluoromethyl)-1,2,4-oxadiazole | 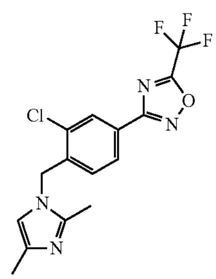 [SMILES: Cc1cn(Cc2ccc(-c3noc(C(F)(F)F)n3)cc2Cl)c(C)n1] | 1.02 | 356.1 | B | |
| 1.106 | 1-[[2-chloro-4-[5-(trifluoromethyl)-1,2,4-oxadiazol-3-yl]phenyl]methyl]imidazole-4,5-dicarbonitrile | 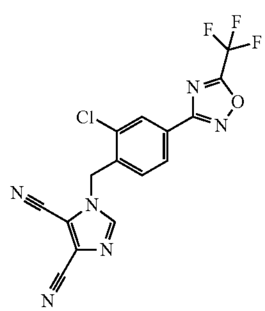 [SMILES: N#Cc1ncn(Cc2ccc(-c3noc(C(F)(F)F)n3)cc2Cl)c1C#N] | 1.69 | 378.0 | B | |
| 1.107 | 3-[4-[(4-bromoimidazol-1-yl)methyl]-3-chloro-phenyl]-5-(trifluoromethyl)-1,2,4-oxadiazole | 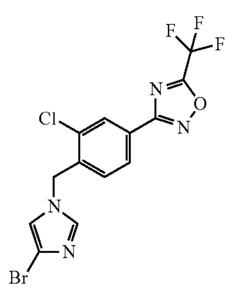 [SMILES: FC(F)(F)c1nc(-c2ccc(Cn3cnc(Br)c3)c(Cl)c2)no1] | 1.69 | 405.9 | B | |
| 1.108 | methyl 1-[[2-chloro-4-[5-(trifluoromethyl)-1,2,4-oxadiazol-3-yl]phenyl]methyl]-1,2,4-triazole-3-carboxylate | 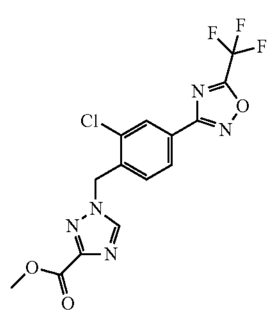 [SMILES: COC(=O)c1ncn(Cc2ccc(-c3noc(C(F)(F)F)n3)cc2Cl)n1] | 1.48 | 387.0 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.109 | 3-[3-chloro-4-[(4-methylimidazol-1-yl)methyl]phenyl]-5-(trifluoromethyl)-1,2,4-oxadiazole | 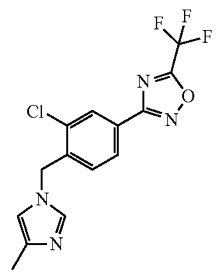 [SMILES: Cc1cn(Cc2ccc(-c3noc(C(F)(F)F)n3)cc2Cl)cn1] | 0.99 | 342.0 | B | |
| 1.110 | 3-[4-(benzimidazol-1-ylmethyl)-3-chloro-phenyl]-5-(trifluoromethyl)-1,2,4-oxadiazole | 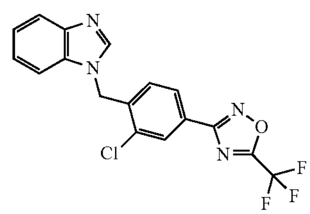 [SMILES: FC(F)(F)c1nc(-c2ccc(Cn3cnc4ccccc43)c(Cl)c2)no1] | 1.46 | 378.0 | B | |
| 1.111 | 3-[3-chloro-4-[(4-chloropyrazol-1-yl)methyl]phenyl]-5-(trifluoromethyl)-1,2,4-oxadiazole | 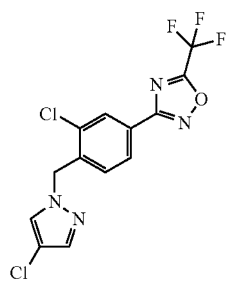 [SMILES: FC(F)(F)c1nc(-c2ccc(Cn3cc(Cl)cn3)c(Cl)c2)no1] | 1.91 | 362.0 | B | |
| 1.112 | 3-[3-chloro-4-(imidazol-1-ylmethyl)phenyl]-5-(trifluoromethyl)-1,2,4-oxadiazole | 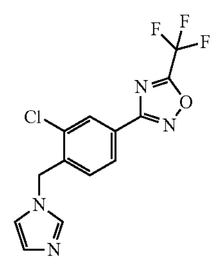 [SMILES: FC(F)(F)c1nc(-c2ccc(Cn3ccnc3)c(Cl)c2)no1] | 0.93 | 328.0 | B | |
| 1.113 | 3-[3-chloro-4-[[5-(4-chlorophenyl)tetrazol-1-yl]methyl]phenyl]-5-(trifluoromethyl)-1,2,4-oxadiazole | 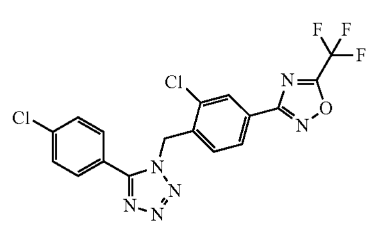 [SMILES: FC(F)(F)c1nc(-c2ccc(Cn3nnnc3-c3ccc(Cl)cc3)c(Cl)c2)no1] | 1.92 | 440.0 | B | |

TABLE T1-continued

Melting point (mp) and/or LC/MS data (retention time (t_R)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.114 | 3-[3-chloro-4-[(4-iodopyrazol-1-yl)methyl]phenyl]-5-(trifluoromethyl)-1,2,4-oxadiazole | 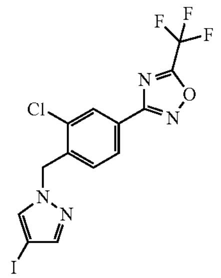 [SMILES: FC(F)(F)c1nc(-c2ccc(Cn3cc(I)cn3)c(Cl)c2)no1] | 1.97 | 453.9 | B | |
| 1.115 | 3-[4-[(4-bromopyrazol-1-yl)methyl]-3-chloro-phenyl]-5-(trifluoromethyl)-1,2,4-oxadiazole | 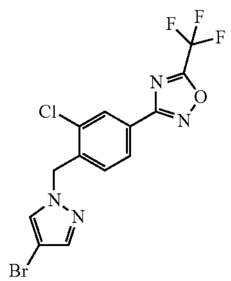 [SMILES: FC(F)(F)c1nc(-c2ccc(Cn3cc(Br)cn3)c(Cl)c2)no1] | 1.94 | 405.9 | B | |
| 1.116 | 3-[4-[(5-bromoimidazol-1-yl)methyl]-3-methoxy-phenyl]-5-(trifluoromethyl)-1,2,4-oxadiazole | 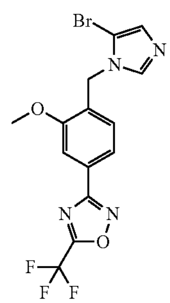 [SMILES: COc1cc(-c2noc(C(F)(F)F)n2)ccc1Cn1cncc1Br] | 1.38 | 402.0 | B | |
| 1.117 | 3-[4-[(4-bromoimidazol-1-yl)methyl]-3-methoxy-phenyl]-5-(trifluoromethyl)-1,2,4-oxadiazole | 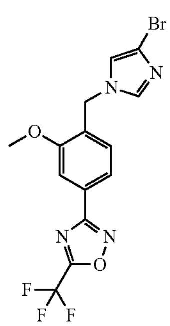 [SMILES: COc1cc(-c2noc(C(F)(F)F)n2)ccc1Cn1cnc(Br)c1] | 1.62 | 402.0 | B | |
| 1.118 | dimethyl 1-[[2-fluoro-4-[5-(trifluoromethyl)-1,2,4-oxadiazol-3-yl]phenyl]methyl] imidazole-4,5-dicarboxylate | 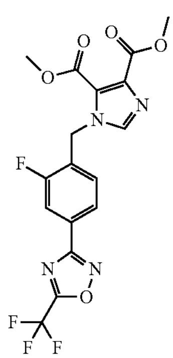 [SMILES: COC(=O)c1ncn(Cc2ccc(-c3noc(C(F)(F)F)n3)cc2F)c1C(=O)OC] | 1.52 | 428.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.119 | 1-[[2-fluoro-4-[5-(trifluoromethyl)-1,2,4-oxadiazol-3-yl]phenyl]methyl] imidazole-4,5-dicarbonitrile | 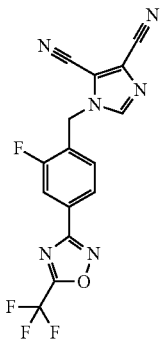 [SMILES: N#Cc1ncn(Cc2ccc(-c3noc(C(F)(F)F)n3)cc2F)c1C#N] | 1.62 | 362.1 | B | |
| 1.120 | 3-[4-[(4-bromoimidazol-1-yl)methyl]-3-fluoro-phenyl]-5-(trifluoromethyl)-1,2,4-oxadiazole | 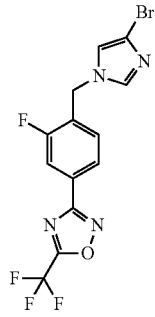 [SMILES: Fc1cc(-c2noc(C(F)(F)F)n2)ccc1Cn1cnc(Br)c1] | 1.60 | 390.0 | B | |
| 1.121 | 3-[4-[(4,5-dichloroimidazol-1-yl)methyl]-3-fluoro-phenyl]-5-(trifluoromethyl)-1,2,4-oxadiazole | 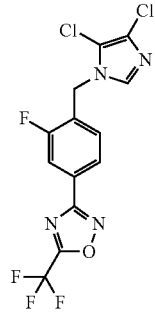 [SMILES: Fc1cc(-c2noc(C(F)(F)F)n2)ccc1Cn1cnc(Cl)c1Cl] | 1.80 | 380.0 | B | |
| 1.122 | methyl 1-[[2-fluoro-4-[5-(trifluoromethyl)-1,2,4-oxadiazol-3-yl]phenyl]methyl]-1,2,4-triazole-3-carboxylate | 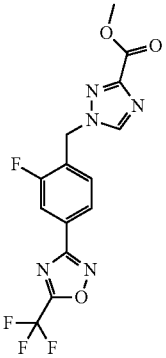 | 1.40 | 371.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.123 | 3-[3-fluoro-4-[(2-methylimidazol-1-yl)methyl]phenyl]-5-(trifluoromethyl)-1,2,4-oxadiazole | 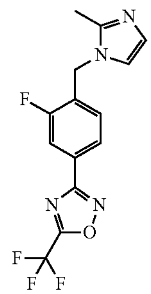 | 0.93 | 326.1 | B | |
| 1.124 | 3-[3-fluoro-4-[(4-methylimidazol-1-yl)methyl]phenyl]-5-(trifluoromethyl)-1,2,4-oxadiazole | 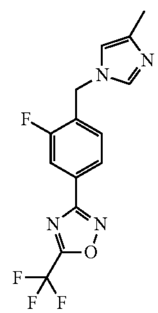 [SMILES: Cc1cn(Cc2ccc(-c3noc(C(F)(F)F)n3)cc2F)cn1] | 0.95 | 326.1 | B | |
| 1.125 | 3-[3-fluoro-4-(pyrrolo[2,3-b]pyridin-7-ylmethyl)phenyl]-5-(trifluoromethyl)-1,2,4-oxadiazole | 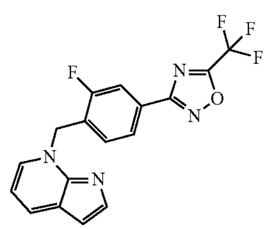 [SMILES: Fc1cc(-c2noc(C(F)(F)F)n2)ccc1Cn1cccc2ccnc1-2] | 0.97 | 362.1 | B | |
| 1.126 | 3-[4-(benzimidazol-1-ylmethyl)-3-fluoro-phenyl]-5-(trifluoromethyl)-1,2,4-oxadiazole | 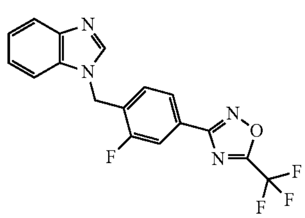 [SMILES: Fc1cc(-c2noc(C(F)(F)F)n2)ccc1Cn1cnc2ccccc21] | 1.33 | 362.1 | B | |
| 1.127 | 3-[4-[(4-chloro-3,5-dimethyl-pyrazol-1-yl)methyl]-3-fluoro-phenyl]-5-(trifluoromethyl)-1,2,4-oxadiazole | 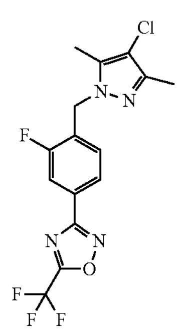 [SMILES: Cc1nn(Cc2ccc(-c3noc(C(F)(F)F)n3)cc2F)c(C)c1Cl] | 1.99 | 374.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.128 | 3-[4-[(4-chloropyrazol-1-yl)methyl]-3-fluoro-phenyl]-5-(trifluoromethyl)-1,2,4-oxadiazole | 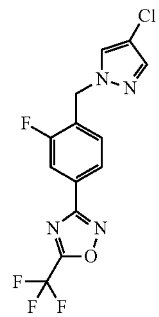 [SMILES: Fc1cc(-c2noc(C(F)(F)F)n2)ccc1Cn1cc(Cl)cn1] | 1.82 | 346.0 | B | |
| 1.129 | 3-[3-fluoro-4-(imidazol-1-ylmethyl)phenyl]-5-(trifluoromethyl)-1,2,4-oxadiazole | 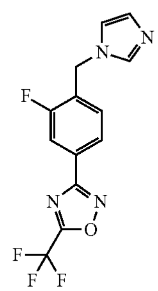 [SMILES: Fc1cc(-c2noc(C(F)(F)F)n2)ccc1Cn1ccnc1] | 0.89 | 312.1 | B | |
| 1.130 | 3-[4-[[5-(4-chlorophenyl)tetrazol-1-yl)methyl]-3-fluoro-phenyl]-5-(trifluoromethyl)-1,2,4-oxadiazole | 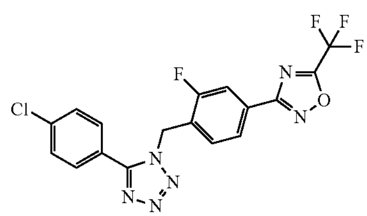 [SMILES: Fc1cc(-c2noc(C(F)(F)F)n2)ccc1Cn1nnnc1-c1ccc(Cl)cc1] | 1.84 | 424.0 | B | |
| 1.131 | 3-[3-fluoro-4-[(4-iodopyrazol-1-yl)methyl]phenyl]-5-(trifluoromethyl)-1,2,4-oxadiazole | 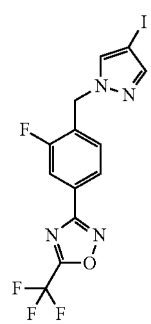 | 1.87 | 438.0 | B | |
| 1.132 | 3-[4-[(4-bromopyrazol-1-yl)methyl]-3-fluoro-phenyl]-5-(trifluoromethyl)-1,2,4-oxadiazole | 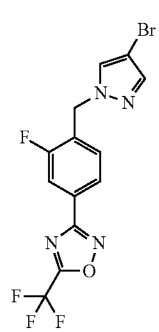 [SMILES: Fc1cc(-c2noc(C(F)(F)F)n2)ccc1Cn1cc(Br)cn1] | 1.84 | 390.0 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.133 | dimethyl 1-[[5-[5-(trifluoromethyl)-1,2,4-oxadiazol-3-yl]-2-pyridyl]methyl]imidazole-4,5-dicarboxylate | 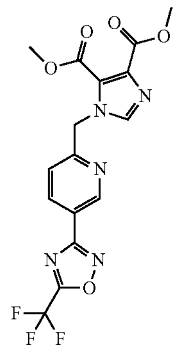 [SMILES: COC(=O)c1ncn(Cc2ccc(-c3noc(C(F)(F)F)n3)cn2)c1C(=O)OC] | 1.30 | 411.1 | B | |
| 1.134 | 3-[6-[(2,4-dimethylimidazol-1-yl)methyl]-3-pyridyl]-5-(trifluoromethyl)-1,2,4-oxadiazole | 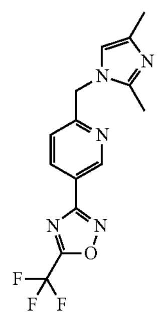 [SMILES: Cc1cn(Cc2ccc(-c3noc(C(F)(F)F)n3)cn2)c(C)n1] | 0.83 | 323.1 | B | |
| 1.135 | 1-[[5-[5-(trifluoromethyl)-1,2,4-oxadiazol-3-yl]-2-pyridyl]methyl]imidazole-4,5-dicarbonitrile | 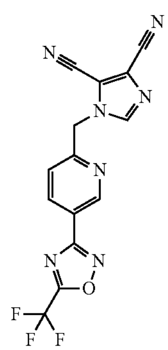 [SMILES: N#Cc1ncn(Cc2ccc(-c3noc(C(F)(F)F)n3)cn2)c1C#N] | 1.44 | 345.1 | B | |
| 1.136 | 3-[6-[(4-bromoimidazol-1-yl)methyl]-3-pyridyl]-5-(trifluoromethyl)-1,2,4-oxadiazole | 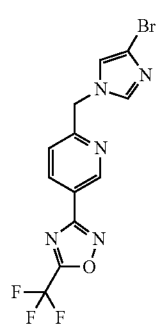 [SMILES: FC(F)(F)c1nc(-c2ccc(Cn3cnc(Br)c3)nc2)no1] | 1.74 | 397.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.137 | 3-[6-[(4,5-dichloroimidazol-1-yl)methyl]-3-pyridyl]-5-(trifluoromethyl)-1,2,4-oxadiazole | 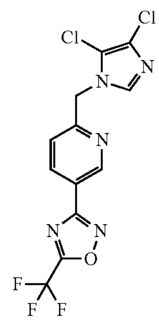 [SMILES: FC(F)(F)c1nc(-c2ccc(Cn3cnc(Cl)c3Cl)nc2)no1] | 1.56 | 363.0 | B | |
| 1.138 | methyl 1-[[5-[5-(trifluoromethyl)-1,2,4-oxadiazol-3-yl]-2-pyridyl]methyl]-1,2,4-triazole-3-carboxylate | 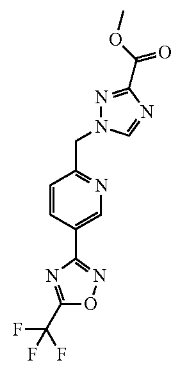 [SMILES: COC(=O)c1ncn(Cc2ccc(-c3noc(C(F)(F)F)n3)cn2)n1] | 1.16 | 354.1 | B | |
| 1.139 | 3-[6-[(2-methylimidazol-1-yl)methyl]-3-pyridyl]-5-(trifluoromethyl)-1,2,4-oxadiazole | 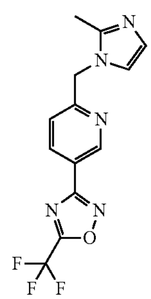 | 0.77 | 309.1 | B | |
| 1.140 | 3-[6-[(3,5-dimethylpyrazol-1-yl)methyl]-3-pyridyl]-5-(trifluoromethyl)-1,2,4-oxadiazole | 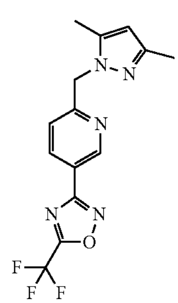 [SMILES: Cc1cc(C)n(Cc2ccc(-c3noc(C(F)(F)F)n3)cn2)n1] | 1.49 | 323.1 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.141 | 3-[6-(imidazol-1-ylmethyl)-3-pyridyl]-5-(trifluoromethyl)-1,2,4-oxadiazole | 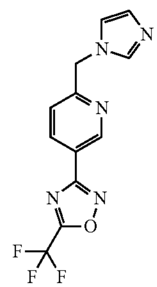 [SMILES: FC(F)(F)c1nc(-c2ccc(Cn3ccnc3)nc2)no1] | 0.72 | 295.1 | B | |
| 1.142 | 3-[6-[[5-(4-chlorophenyl)tetrazol-2-yl]methyl]-3-pyridyl]-5-(trifluoromethyl)-1,2,4-oxadiazole | 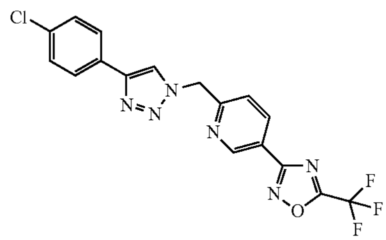 [SMILES: FC(F)(F)c1nc(-c2ccc(Cn3cc(-c4ccc(Cl)cc4)nn3)nc2)no1] | 1.89 | 407.1 | B | |
| 1.143 | 3-[6-(1,2,4-triazol-1-ylmethyl)-3-pyridyl]-5-(trifluoromethyl)-1,2,4-oxadiazole | 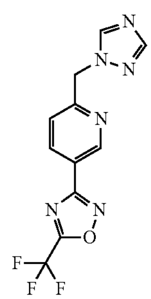 | 1.06 | 296.1 | B | |
| 1.144 | 3-[6-[(4-iodopyrazol-1-yl)methyl]-3-pyridyl]-5-(trifluoromethyl)-1,2,4-oxadiazole | 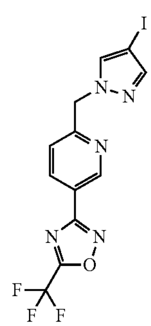 | 1.56 | 373.0 | B | |
| 1.145 | 3-[4-[(2,4-dimethylimidazol-1-yl)methyl]-3-fluoro-phenyl]-5-(trifluoromethyl)-1,2,4-oxadiazole | 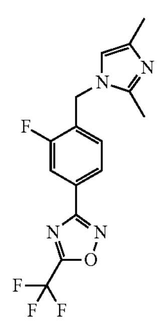 [SMILES: Cc1cn(Cc2ccc(-c3noc(C(F)(F)F)n3)cc2F)c(C)n1] | 1.01 | 340.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.146 | 5-(trifluoromethyl)-3-[4-[(3,4,5-trimethylpyrazol-1-yl)methyl]phenyl]-1,2,4-oxadiazole | 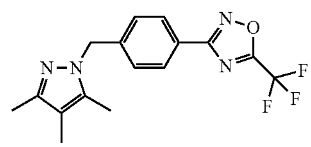 [SMILES: Cc1nn(Cc2ccc(-c3noc(C(F)(F)F)n3)cc2)c(C)c1C] | | | B | 99.4-102 |
| 1.147 | 1-[[4-[5-(trifluoromethyl)-1,2,4-oxadiazol-3-yl]phenyl]methyl]pyrazole-4-carboxylic acid | 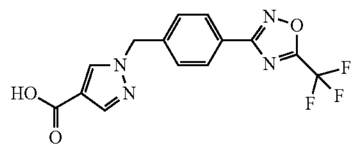 [SMILES: O=C(O)c1cnn(Cc2ccc(-c3noc(C(F)(F)F)n3)cc2)c1] | 0.83 | 323.1 | B | 182-192 |
| 1.148 | N-cyclopropyl-1-[[4-[5-(trifluoromethyl)-1,2,4-oxadiazol-3-yl]phenyl]methyl]pyrazole-4-carboxamide | 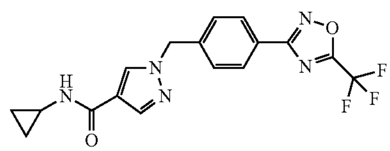 [SMILES: O=C(NC1CC1)c1cnn(Cc2ccc(-c3noc(C(F)(F)F)n3)cc2)c1] | 1.44 | 345.1 | B | 189-194 |
| 1.149 | N,N-dimethyl-1-[[4-[5-(trifluoromethyl)-1,2,4-oxadiazol-3-yl]phenyl]methyl]pyrazole-4-carboxamide | 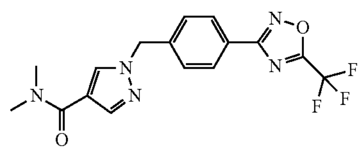 | | | | 124-129 |
| 1.150 | N-methyl-1-[[4-[5-(trifluoromethyl)-1,2,4-oxadiazol-3-yl]phenyl]methyl]pyrazole-4-carboxamide | 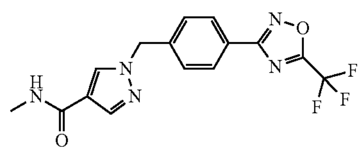 [SMILES: CNC(=O)c1cnn(Cc2ccc(-c3noc(C(F)(F)F)n3)cc2)c1] | | | | 156-161 |
| 1.151 | 1-[[4-[5-(trifluoromethyl)-1,2,4-oxadiazol-3-yl]phenyl]methyl]imidazole-4-carbaldehyde | 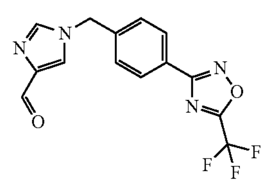 [SMILES: O=Cc1cn(Cc2ccc(-c3noc(C(F)(F)F)n3)cc2)cn1] | 1.26 | 323.1 | B | |
| 1.152 | 3-[4-[[5-(2-bromophenyl)tetrazol-1-yl]methyl]phenyl]-5-(trifluoromethyl)-1,2,4-oxadiazole | 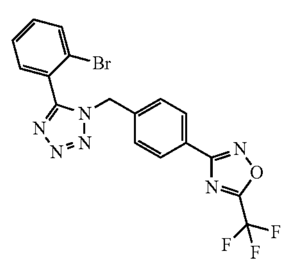 [SMILES: FC(F)(F)c1nc(-c2ccc(Cn3nnnc3-c3ccccc3Br)cc2)no1] | 1.77 | 451.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.153 | 3-[4-[[5-(2-bromophenyl)tetrazol-2-yl]methyl]phenyl]-5-(trifluoromethyl)-1,2,4-oxadiazole | 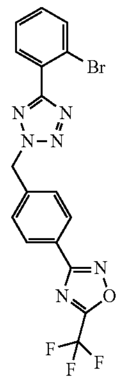 [SMILES: FC(F)(F)c1nc(-c2ccc(Cn3nnc(-c4ccccc4Br)n3)cc2)no1] | 1.98 | 451.1 | B | |
| 1.154 | 1-[[4-[5-(trifluoromethyl)-1,2,4-oxadiazol-3-yl]phenyl]methyl]imidazole-4-carbonitrile | 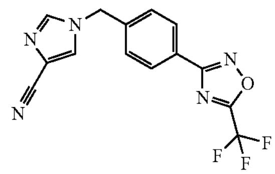 [SMILES: N#Cc1cn(Cc2ccc(-c3noc(C(F)(F)F)n3)cc2)cn1] | 1.41 | 320.1 | B | |
| 1.155 | 3-[4-[(5,6-dichlorobenzotriazol-1-yl)methyl]phenyl]-5-(trifluoromethyl)-1,2,4-oxadiazole | 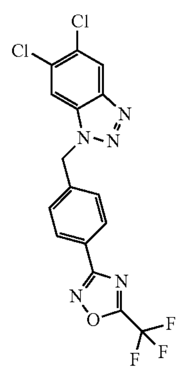 [SMILES: FC(F)(F)c1nc(-c2ccc(Cn3nnc4cc(Cl)c(Cl)cc43)cc2)no1] | 1.98 | 414.1 | B | |
| 1.156 | N-[2-[1-[[4-[5-(trifluoromethyl)-1,2,4-oxadiazol-3-yl]phenyl]methyl]imidazol-4-yl]ethyl]acetamide | 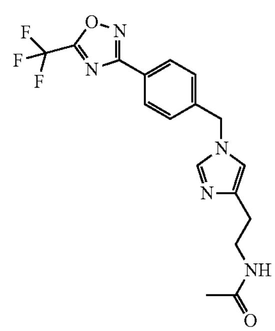 [SMILES: CC(=O)NCCc1cn(Cc2ccc(-c3noc(C(F)(F)F)n3)cc2)cn1] | 0.86 | 380.2 | B | |
| 1.157 | 4-[[4-[5-(trifluoromethyl)-1,2,4-oxadiazol-3-yl]phenyl]methyl]pyrrolo[3,2-b]pyridine-2-carbonitrile | 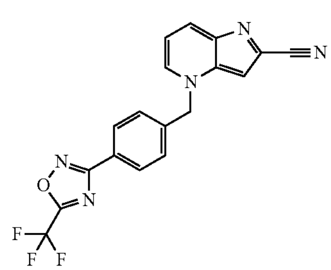 [SMILES: N#Cc1cc2n(Cc3ccc(-c4noc(C(F)(F)F)n4)cc3)cccc-2n1] | 1.02 | 370.1 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.158 | 1-[[4-[5-(trifluoromethyl)-1,2,4-oxadiazol-3-yl]phenyl]methyl]pyrrolo[3,2-b]pyridine-2-carbonitrile | 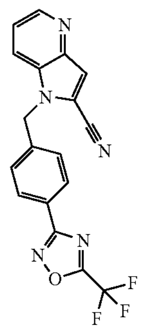 [SMILES: N#Cc1cc2ncccc2n1Cc1ccc(-c2noc(C(F)(F)F)n2)cc1] | 1.58 | 370.1 | B | |
| 1.159 | 3-[4-[[6-(4-bromophenyl)sulfanyl-5-chloro-benzotriazol-1-yl]methyl]phenyl]-5-(trifluoromethyl)-1,2,4-oxadiazole | 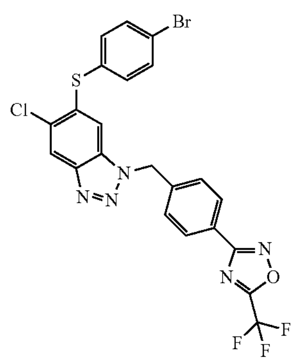 [SMILES: FC(F)(F)c1nc(-c2ccc(Cn3nnc4cc(Cl)c(Sc5ccc(Br)cc5)cc43)cc2)no1] | 2.31 | 566.0 | B | |
| 1.160 | 3-[4-[[5-(4-bromophenyl)sulfanyl-6-chloro-benzotriazol-2-yl]methyl]phenyl]-5-(trifluoromethyl)-1,2,4-oxadiazole | 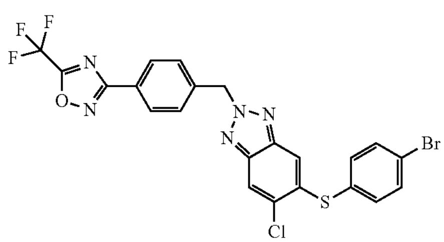 [SMILES: FC(F)(F)c1nc(-c2ccc(Cn3nc4cc(Cl)c(Sc5ccc(Br)cc5)cc4n3)cc2)no1] | 2.46 | 566.0 | B | |
| 1.161 | ethyl 5-(4-chlorophenyl)-2-(trifluoromethyl)-1-[[4-[5-(trifluoromethyl)-1,2,4-oxadiazol-3-yl]phenyl]methyl]imidazole-4-carboxylate | 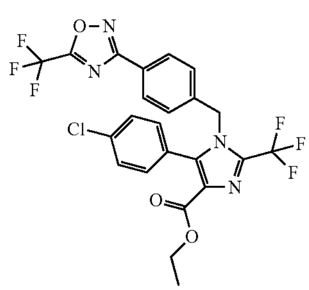 [SMILES: CCOC(=O)c1nc(C(F)(F)F)n(Cc2ccc(-c3noc(C(F)(F)F)n3)cc2)c1-c1ccc(Cl)cc1] | 2.08 | 545.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.162 | ethyl 5-(4-chlorophenyl)-2-(trifluoromethyl)-3-[[4-[5-(trifluoromethyl)-1,2,4-oxadiazol-3-yl]phenyl]methyl]imidazole-4-carboxylate | 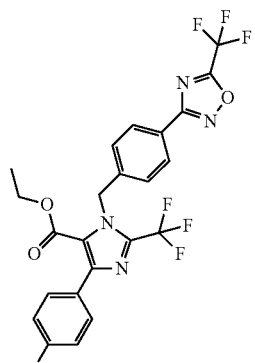 | 2.27 | 545.2 | B | |
| 1.163 | 3-[4-[[5-chloro-6-(4-methoxyphenoxy)benzotriazol-1-yl]methyl]phenyl]-5-(trifluoromethyl)-1,2,4-oxadiazole | 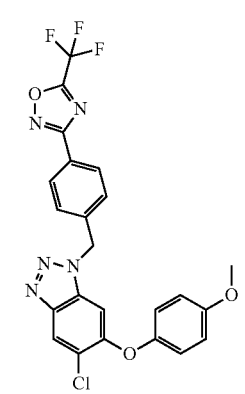 [SMILES: COc1ccc(Oc2cc3c(cc2Cl)nnn3Cc2ccc(-c3noc(C(F)(F)F)n3)cc2)cc1] | 2.06 | 502.2 | B | |
| 1.164 | 3-[4-[[5-chloro-6-(4-methoxyphenoxy)benzotriazol-2-yl]methyl]phenyl]-5-(trifluoromethyl)-1,2,4-oxadiazole | 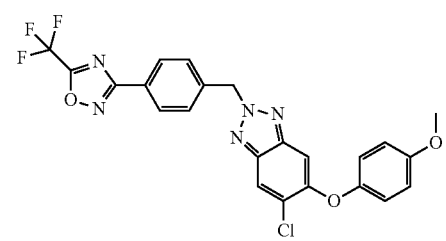 [SMILES: COc1ccc(Oc2cc3nn(Cc4ccc(-c5noc(C(F)(F)F)n5)cc4)nc3cc2Cl)cc1] | 2.21 | 502.2 | B | |
| 1.165 | 3-[4-[[5-(4-fluorophenyl)-3-(trifluoromethyl)pyrazol-1-yl]methyl]phenyl]-5-(trifluoromethyl)-1,2,4-oxadiazole | 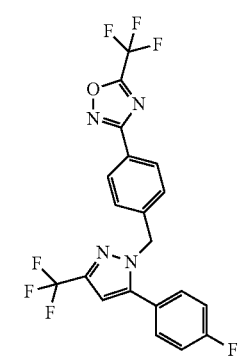 [SMILES: Fc1ccc(-c2cc(C(F)(F)F)nn2Cc2ccc(-c3noc(C(F)(F)F)n3)cc2)cc1] | 2.14 | 457.2 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.166 | 3-[4-[[3-(4-fluorophenyl)-5-(trifluoromethyl) pyrazol-1-yl]methyl]phenyl]-5-(trifluoromethyl)-1,2,4-oxadiazole | 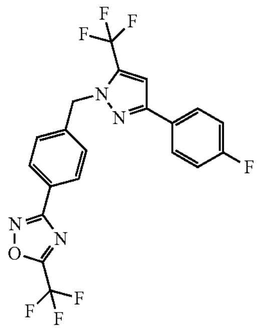 [SMILES: Fc1ccc(-c2cc(C(F)(F)F)n(Cc3ccc(-c4noc(C(F)(F)F)n4)cc3)n2)cc1] | 2.25 | 457.2 | B | |
| 1.167 | 3-[4-[[5-(2,4-difluorophenyl)-3-(trifluoromethyl) pyrazol-1-yl]methyl]phenyl]-5-(trifluoromethyl)-1,2,4-oxadiazole | 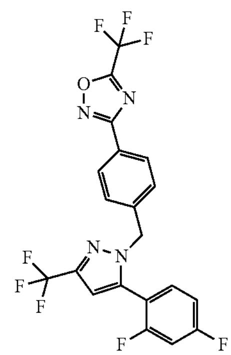 [SMILES: Fc1ccc(-c2cc(C(F)(F)F)nn2Cc2ccc(-c3noc(C(F)(F)F)n3)cc2)c(F)c1] | 2.14 | 475.2 | B | |
| 1.168 | 3-[4-[[3-(2,4-difluorophenyl)-5-(trifluoromethyl) pyrazol-1-yl]methyl]phenyl]-5-(trifluoromethyl)-1,2,4-oxadiazole | 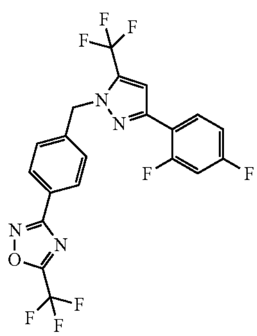 [SMILES: Fc1ccc(-c2cc(C(F)(F)F)n(Cc3ccc(-c4noc(C(F)(F)F)n4)cc3)n2)c(F)c1] | 2.31 | 475.2 | B | |
| 1.169 | methyl 5-(2,5-difluorophenyl)-1-[[4-[5-(trifluoromethyl)-1,2,4-oxadiazol-3-yl]phenyl]methyl] pyrazole-3-carboxylate | 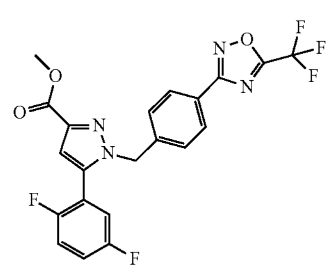 [SMILES: COC(=O)c1cc(-c2cc(F)ccc2F)n(Cc2ccc(-c3noc(C(F)(F)F)n3)cc2)n1] | 1.89 | 465.2 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]⁺ | LCMS Method | mp (° C.) |
|---|---|---|---|---|---|---|
| 1.170 | methyl 5-(2,5-difluorophenyl)-2-[[4-[5-(trifluoromethyl)-1,2,4-oxadiazol-3-yl]phenyl]methyl]pyrazole-3-carboxylate | 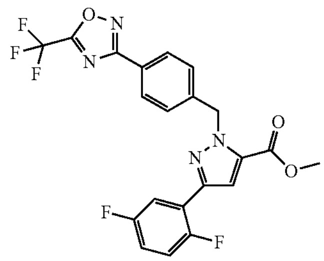 [SMILES: COC(=O)c1cc(-c2cc(F)ccc2F)nn1Cc1ccc(-c2noc(C(F)(F)F)n2)cc1] | 2.22 | 465.2 | B | |
| 1.171 | 5-methyl-1-[[4-[5-(trifluoromethyl)-1,2,4-oxadiazol-3-yl]phenyl]methyl]pyrazol-3-ol | 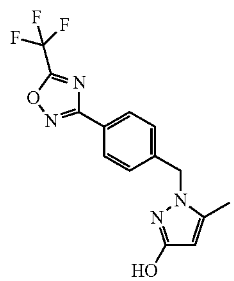 [SMILES: Cc1cc(O)nn1Cc1ccc(-c2noc(C(F)(F)F)n2)cc1] | 1.40 | 325.1 | B | |
| 1.172 | 3-[4-[[5-(4-methoxyphenyl)-3-(trifluoromethyl)pyrazol-1-yl]methyl]phenyl]-5-(trifluoromethyl)-1,2,4-oxadiazole | 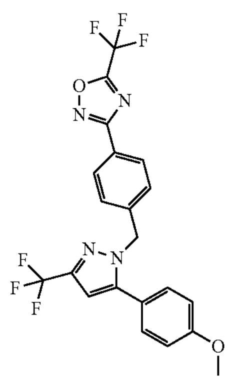 [SMILES: COc1ccc(-c2cc(C(F)(F)F)nn2Cc2ccc(-c3noc(C(F)(F)F)n3)cc2)cc1] | 2.14 | 469.2 | B | |
| 1.173 | 3-[4-[[3-(4-methoxyphenyl)-5-(trifluoromethyl)pyrazol-1-yl]methyl]phenyl]-5-(trifluoromethyl)-1,2,4-oxadiazole | 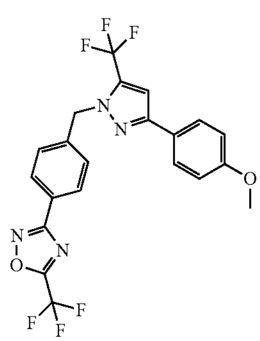 [SMILES: COc1ccc(-c2cc(C(F)(F)F)n(Cc3ccc(-c4noc(C(F)(F)F)n4)cc3)n2)cc1] | 2.22 | 469.2 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.174 | 3-[4-[[4-(4-chlorophenyl)-2-(difluoromethyl-sulfanyl)imidazol-1-yl]methyl]phenyl]-5-(trifluoromethyl)-1,2,4-oxadiazole | 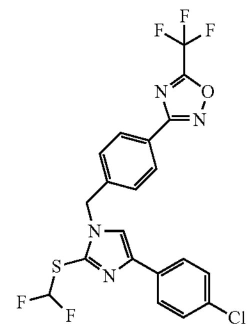 [SMILES: FC(F)Sc1nc(-c2ccc(Cl)cc2)cn1Cc1ccc(-c2noc(C(F)(F)F)n2)cc1] | 2.08 | 487.1 | B | |
| 1.175 | 3-[4-[(6-bromo-4,5-dimethyl-benzotriazol-1-yl)methyl]phenyl]-5-(trifluoromethyl)-1,2,4-oxadiazole | 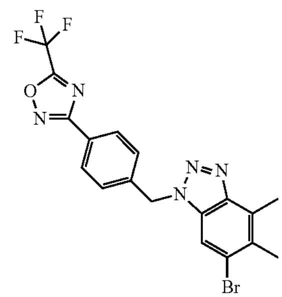 [SMILES: Cc1c(Br)cc2c(nnn2Cc2ccc(-c3noc(C(F)(F)F)n3)cc2)c1C] | 2.08 | 452.1 | B | |
| 1.176 | 3-[4-[(6-bromo-4,5-dimethyl-benzotriazol-2-yl)methyl]phenyl]-5-(trifluoromethyl)-1,2,4-oxadiazole | 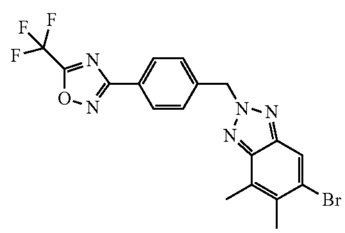 [SMILES: Cc1c(Br)cc2nn(Cc3ccc(-c4noc(C(F)(F)F)n4)cc3)nc2c1C] | 2.27 | 452.1 | B | |
| 1.177 | 3-[4-[[6-(1,3-benzodioxol-5-yloxy)-5-chloro-benzotriazol-1-yl]methyl]phenyl]-5-(trifluoromethyl)-1,2,4-oxadiazole | 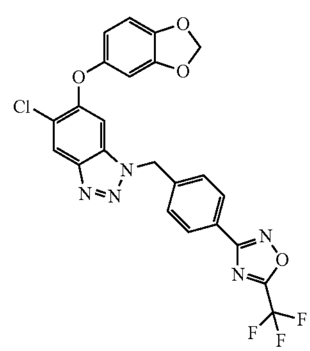 [SMILES: FC(F)(F)c1nc(-c2ccc(Cn3nnc4cc(Cl)c(Oc5ccc6c(c5)OCO6)cc43)cc2)no1] | 2.03 | 516.2 | B | |
| 1.178 | 3-[4-[[5-(1,3-benzodioxol-5-yloxy)-6-chloro-benzotriazol-2-yl]methyl]phenyl]-5-(trifluoromethyl)-1,2,4-oxadiazole | 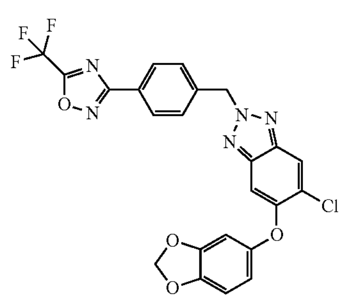 [SMILES: FC(F)(F)c1nc(-c2ccc(Cn3nc4cc(Cl)c(Oc5ccc6c(c5)OCO6)cc4n3)cc2)no1] | 2.19 | 516.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.179 | 3-[4-[[4-chloro-5-(4-fluorophenoxy)benzotriazol-1-yl]methyl]phenyl]-5-(trifluoromethyl)-1,2,4-oxadiazole | 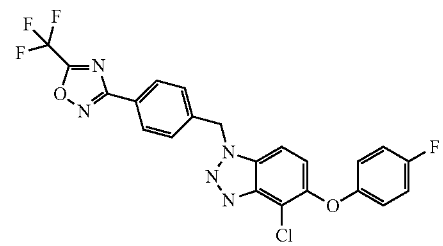 [SMILES: Fc1ccc(Oc2ccc3c(c2Cl)NNN3Cc2ccc(-c3noc(C(F)(F)F)n3)cc2)cc1] | 2.03 | 490.1 | B | |
| 1.180 | 3-[4-[[7-chloro-6-(4-fluorophenoxy)benzotriazol-1-yl]methyl]phenyl]-5-(trifluoromethyl)-1,2,4-oxadiazole | 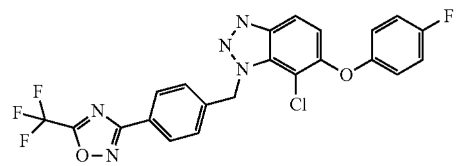 [SMILES: Fc1ccc(Oc2ccc3c(c2Cl)N(Cc2ccc(-c4noc(C(F)(F)F)n4)cc2)NN3)cc1] | 2.12 | 490.2 | B | |
| 1.181 | 3-[4-[[4-chloro-5-(4-fluorophenoxy)benzotriazol-2-yl]methyl]phenyl]-5-(trifluoromethyl)-1,2,4-oxadiazole | 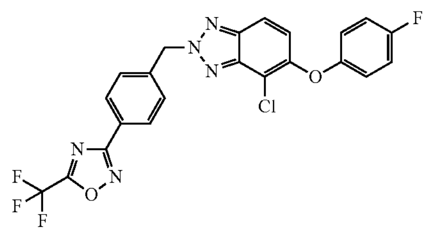 [SMILES: Fc1ccc(Oc2ccc3nn(Cc4ccc(-c5noc(C(F)(F)F)n5)cc4)nc3c2Cl)cc1] | 2.19 | 490.1 | B | |
| 1.182 | ethyl 5-(4-chlorophenyl)-1-[[4-[5-(trifluoromethyl)-1,2,4-oxadiazol-3-yl]phenyl]methyl]-2-(trifluoromethylsulfanyl)imidazole-4-carboxylate | 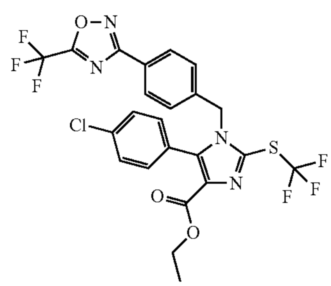 [SMILES: CCOC(=O)c1nc(SC(F)(F)F)n(Cc2ccc(-c3noc(C(F)(F)F)n3)cc2)c1-c1ccc(Cl)cc1] | 2.13 | 577.1 | B | |
| 1.183 | ethyl 5-(4-chlorophenyl)-3-[[4-[5-(trifluoromethyl)-1,2,4-oxadiazol-3-yl]phenyl]methyl]-2-(trifluoromethylsulfanyl)imidazole-4-carboxylate | 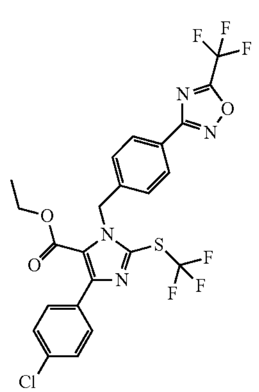 [SMILES: CCOC(=O)c1c(-c2ccc(Cl)cc2)nc(SC(F)(F)F)n1Cc1ccc(-c2noc(C(F)(F)F)n2)cc1] | 2.30 | 577.1 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.184 | ethyl 1-[[4-[5-(trifluoromethyl)-1,2,4-oxadiazol-3-yl]phenyl]methyl]benzotriazole-5-carboxylate | 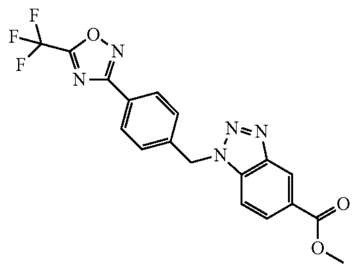 [SMILES: COC(=O)c1ccc2c(c1)nnn2Cc1ccc(-c2noc(C(F)(F)F)n2)cc1] | 1.84 | 418.2 | B | |
| 1.185 | ethyl 2-[[4-[5-(trifluoromethyl)-1,2,4-oxadiazol-3-yl]phenyl]methyl]benzotriazole-5-carboxylate | 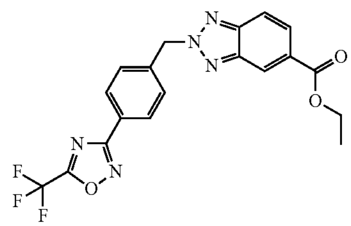 [SMILES: CCOC(=O)c1ccc2nn(Cc3ccc(-c4noc(C(F)(F)F)n4)cc3)nc2c1] | 2.00 | 418.2 | B | |
| 1.186 | ethyl 5-cyclopropyl-1-[[4-[5-(trifluoromethyl)-1,2,4-oxadiazol-3-yl]phenyl]methyl]pyrazole-3-carboxylate | 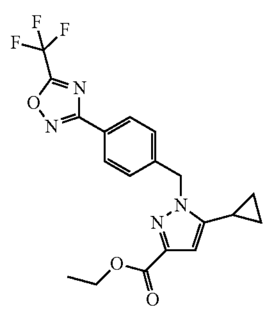 [SMILES: CCOC(=O)c1cc(C2CC2)n(Cc2ccc(-c3noc(C(F)(F)F)n3)cc2)n1] | 1.87 | 407.2 | B | |
| 1.187 | ethyl 5-cyclopropyl-2-[[4-[5-(trifluoromethyl)-1,2,4-oxadiazol-3-yl]phenyl]methyl]pyrazole-3-carboxylate | 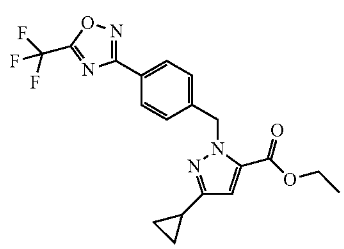 [SMILES: CCOC(=O)c1cc(C2CC2)nn1Cc1ccc(-c2noc(C(F)(F)F)n2)cc1] | 2.08 | 407.2 | B | |
| 1.188 | ethyl 5-phenyl-1-[[4-[5-(trifluoromethyl)-1,2,4-oxadiazol-3-yl]phenyl]methyl]imidazole-4-carboxylate | 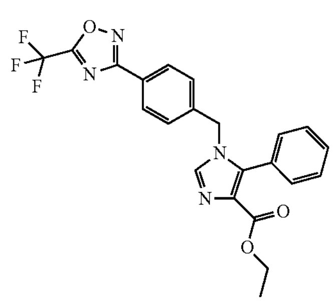 [SMILES: CCOC(=O)c1ncn(Cc2ccc(-c3noc(C(F)(F)F)n3)cc2)c1-c1ccccc1] | 1.72 | 443.2 | B | |

TABLE T1-continued

Melting point (mp) and/or LC/MS data (retention time (t_R)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.189 | ethyl 5-phenyl-3-[[4-[5-(trifluoromethyl)-1,2,4-oxadiazol-3-yl]phenyl]methyl]imidazole-4-carboxylate | 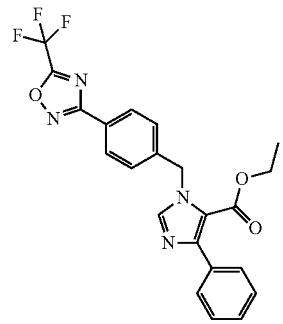 [SMILES: CCOC(=O)c1c(-c2ccccc2)ncn1Cc1ccc(-c2noc(C(F)(F)F)n2)cc1] | 1.83 | 443.2 | B | |
| 1.190 | 3-[4-[[2-methyl-6-(trifluoromethyl)benzimidazol-1-yl]methyl]phenyl]-5-(trifluoromethyl)-1,2,4-oxadiazole | 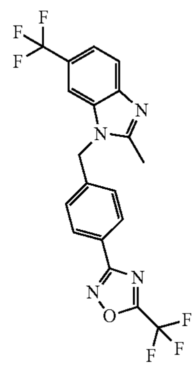 [SMILES: Cc1nc2ccc(C(F)(F)F)cc2n1Cc1ccc(-c2noc(C(F)(F)F)n2)cc1] | 1.69 | 427.2 | B | |
| 1.191 | 3-[4-[[2-methyl-5-(trifluoromethyl)benzimidazol-1-yl]methyl]phenyl]-5-(trifluoromethyl)-1,2,4-oxadiazole | 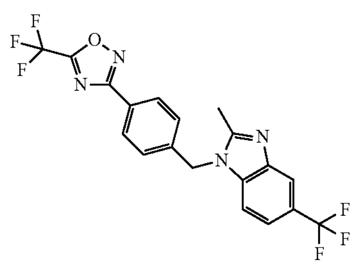 [SMILES: Cc1nc2cc(C(F)(F)F)ccc2n1Cc1ccc(-c2noc(C(F)(F)F)n2)cc1] | 1.73 | 427.2 | B | |
| 1.192 | methyl 2-[[4-[5-(trifluoromethyl)-1,2,4-oxadiazol-3-yl]phenyl]methyl]indazole-4-carboxylate | 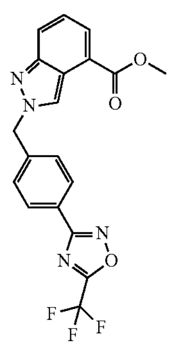 [SMILES: COC(=O)c1cccc2nn(Cc3ccc(-c4noc(C(F)(F)F)n4)cc3)cc12] | 1.80 | 403.2 | B | |
| 1.193 | methyl 1-[[4-[5-(trifluoromethyl)-1,2,4-oxadiazol-3-yl]phenyl]methyl]indazole-4-carboxylate | 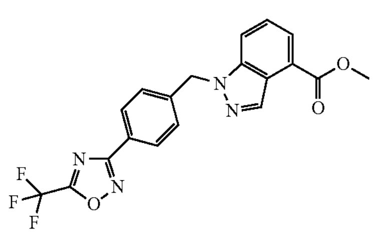 [SMILES: COC(=O)c1cccc2c1cnn2Cc1ccc(-c2noc(C(F)(F)F)n2)cc1] | 1.87 | 403.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.194 | 6-fluoro-1-[[4-[5-(trifluoromethyl)-1,2,4-oxadiazol-3-yl]phenyl]methyl]indazole-3-carbonitrile | 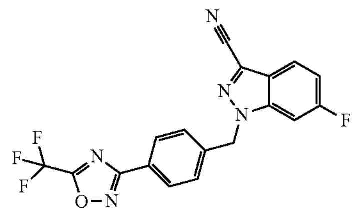 [SMILES: N#Cc1nn(Cc2ccc(-c3noc(C(F)(F)F)n3)cc2)c2cc(F)ccc12] | 1.94 | 388.1 | B | |
| 1.195 | 3-[4-[[4-chloro-6-(trifluoromethyl)benzotriazol-1-yl]methyl]phenyl]-5-(trifluoromethyl)-1,2,4-oxadiazole | 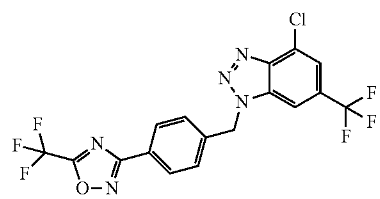 [SMILES: FC(F)(F)c1cc(Cl)c2nnn(Cc3ccc(-c4noc(C(F)(F)F)n4)cc3)c2c1] | 2.03 | 448.1 | B | |
| 1.196 | 3-[4-[[7-chloro-5-(trifluoromethyl)benzotriazol-1-yl]methyl]phenyl]-5-(trifluoromethyl)-1,2,4-oxadiazole | 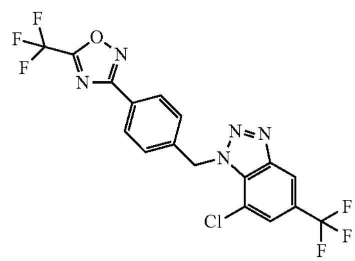 [SMILES: FC(F)(F)c1cc(Cl)c2c(c1)nnn2Cc1ccc(-c2noc(C(F)(F)F)n2)cc1] | 2.09 | 448.1 | B | |
| 1.197 | 3-[4-[[4-chloro-6-(trifluoromethyl)benzotriazol-2-yl]methyl]phenyl]-5-(trifluoromethyl)-1,2,4-oxadiazole | 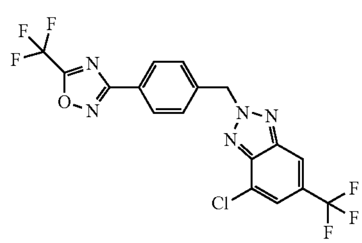 [SMILES: FC(F)(F)c1cc(Cl)c2nn(Cc3ccc(-c4noc(C(F)(F)F)n4)cc3)nc2c1] | 0.00 | 448.1 | B | |
| 1.198 | 3-[4-[(4,5-dimethylbenzotriazol-1-yl)methyl]phenyl]-5-(trifluoromethyl)-1,2,4-oxadiazole | 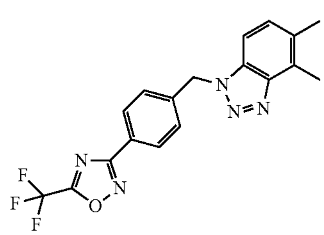 [SMILES: Cc1ccc2c(nnn2Cc2ccc(-c3noc(C(F)(F)F)n3)cc2)c1C] | 1.88 | 374.2 | B | |
| 1.199 | 3-[4-[(4,5-dimethylbenzotriazol-2-yl)methyl]phenyl]-5-(trifluoromethyl)-1,2,4-oxadiazole | 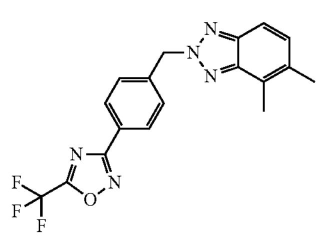 [SMILES: Cc1ccc2nn(Cc3ccc(-c4noc(C(F)(F)F)n4)cc3)nc2c1C] | 2.06 | 374.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.200 | 5-(trifluoromethyl)-2-[[4-[5-(trifluoromethyl)-1,2,4-oxadiazol-3-yl]phenyl]methyl]-1,2,4-triazol-3-amine | 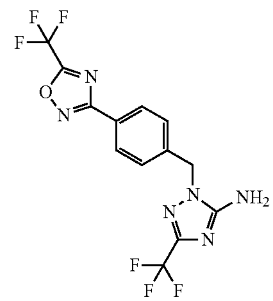 [SMILES: Nc1nc(C(F)(F)F)nn1Cc1ccc(-c2noc(C(F)(F)F)n2)cc1] | 1.56 | 379.1 | B | |
| 1.201 | 3-[4-[[5-(p-tolyl)tetrazol-1-yl]methyl]phenyl]-5-(trifluoromethyl)-1,2,4-oxadiazole | 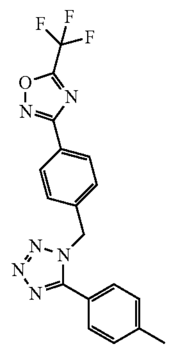 [SMILES: Cc1ccc(-c2nnnn2Cc2ccc(-c3noc(C(F)(F)F)n3)cc2)cc1] | 1.78 | 387.2 | B | |
| 1.202 | 3-[4-[[5-(p-tolyl)tetrazol-2-yl]methyl]phenyl]-5-(trifluoromethyl)-1,2,4-oxadiazole | 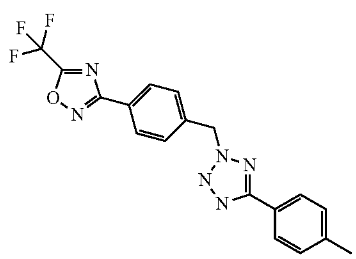 [SMILES: Cc1ccc(C2=NN(Cc3ccc(-c4noc(C(F)(F)F)n4)cc3)NN2)cc1] | 2.03 | 387.2 | B | |
| 1.203 | N,N-dimethyl-1-[[4-[5-(trifluoromethyl)-1,2,4-oxadiazol-3-yl]phenyl]methyl]-1,2,4-triazol-3-amine | 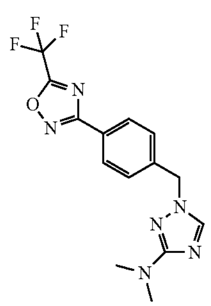 [SMILES: CN(C)c1ncn(Cc2ccc(-c3noc(C(F)(F)F)n3)cc2)n1] | 1.44 | 339.2 | B | |
| 1.204 | ethyl 3-(difluoromethyl)-1-[[4-[5-(trifluoromethyl)-1,2,4-oxadiazol-3-yl]phenyl]methyl] pyrazole-4-carboxylate | 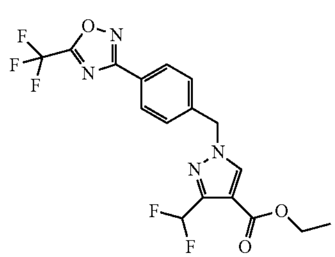 [SMILES: CCOC(=O)c1cn(Cc2ccc(-c3noc(C(F)(F)F)n3)cc2)nc1C(F)F] | 1.82 | 417.2 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.205 | ethyl 5-(difluoromethyl)-1-[[4-[5-(trifluoromethyl)-1,2,4-oxadiazol-3-yl]phenyl]methyl]pyrazole-4-carboxylate | 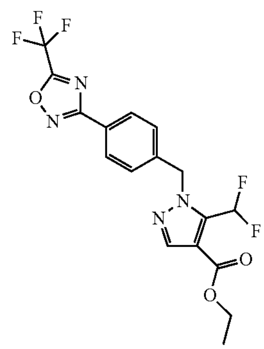 [SMILES: CCOC(=O)c1cnn(Cc2ccc(-c3noc(C(F)(F)F)n3)cc2)c1C(F)F] | 1.97 | 417.2 | B | |
| 1.206 | 3-[4-[(3-propylsulfanyl-1,2,4-triazol-1-yl)methyl]phenyl]-5-(trifluoromethyl)-1,2,4-oxadiazole | 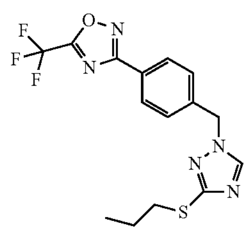 [SMILES: CCCSc1ncn(Cc2ccc(-c3noc(C(F)(F)F)n3)cc2)n1] | 1.76 | 370.1 | B | |
| 1.207 | 3-[4-[(5-propylsulfanyl-1,2,4-triazol-1-yl)methyl]phenyl]-5-(trifluoromethyl)-1,2,4-oxadiazole | 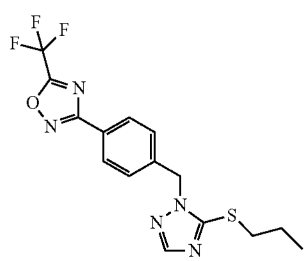 [SMILES: CCCSc1ncnn1Cc1ccc(-c2noc(C(F)(F)F)n2)cc1] | 1.82 | 370.1 | B | |
| 1.208 | 3-[4-[(3-ethylsulfanyl-1,2,4-triazol-1-yl)methyl]phenyl]-5-(trifluoromethyl)-1,2,4-oxadiazole | 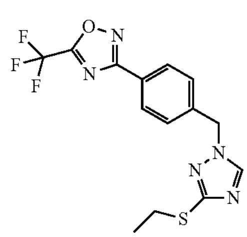 [SMILES: CCSc1ncn(Cc2ccc(-c3noc(C(F)(F)F)n3)cc2)n1] | 1.64 | 356.1 | B | |
| 1.209 | 3-[4-[(5-ethylsulfanyl-1,2,4-triazol-1-yl)methyl]phenyl]-5-(trifluoromethyl)-1,2,4-oxadiazole | 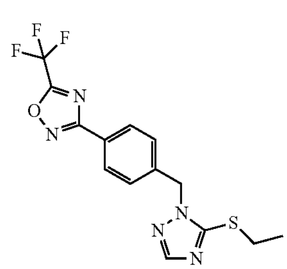 [SMILES: CCSc1ncnn1Cc1ccc(-c2noc(C(F)(F)F)n2)cc1] | 1.70 | 356.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.210 | 4-chloro-5-(4-chlorophenyl)-1-[[4-[5-(trifluoromethyl)-1,2,4-oxadiazol-3-yl]phenyl]methyl]pyrazole-3-carbonitrile | 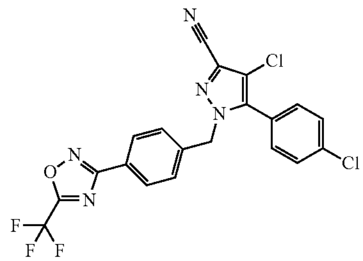 [SMILES: N#Cc1nn(Cc2ccc(-c3noc(C(F)(F)F)n3)cc2)c(-c2ccc(Cl)cc2)c1Cl] | 2.18 | 464.1 | B | |
| 1.211 | 4-chloro-5-(4-chlorophenyl)-2-[[4-[5-(trifluoromethyl)-1,2,4-oxadiazol-3-yl]phenyl]methyl]pyrazole-3-carbonitrile | 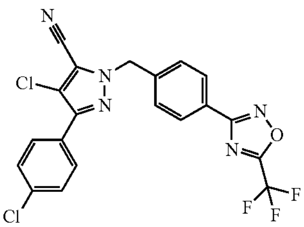 [SMILES: N#Cc1c(Cl)c(-c2ccc(Cl)cc2)nn1Cc1ccc(-c2noc(C(F)(F)F)n2)cc1] | 2.30 | 464.2 | B | |
| 1.212 | 3-[4-[(3-benzylsulfanyl-1,2,4-triazol-1-yl)methyl]phenyl]-5-(trifluoromethyl)-1,2,4-oxadiazole | 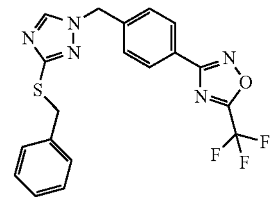 [SMILES: FC(F)(F)c1nc(-c2ccc(Cn3cnc(SCc4ccccc4)n3)cc2)no1] | 1.83 | 418.2 | B | |
| 1.213 | 3-[4-[(3-benzylsulfanyl-1,2,4-triazol-4-yl)methyl]phenyl]-5-(trifluoromethyl)-1,2,4-oxadiazole | 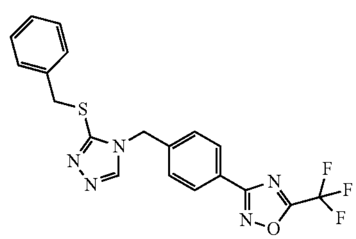 [SMILES: FC(F)(F)c1nc(-c2ccc(Cn3cnnc3SCc3ccccc3)cc2)no1] | 1.89 | 418.2 | B | |
| 1.214 | 5-methoxy-2-[[4-[5-(trifluoromethyl)-1,2,4-oxadiazol-3-yl]phenyl]methyl]-1,2,4-triazol-3-amine | 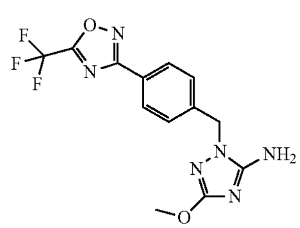 [SMILES: COc1nc(N)n(Cc2ccc(-c3noc(C(F)(F)F)n3)cc2)n1] | 1.24 | 341.1 | B | |
| 1.215 | 5-methoxy-1-[[4-[5-(trifluoromethyl)-1,2,4-oxadiazol-3-yl]phenyl]methyl]-1,2,4-triazol-3-amine | 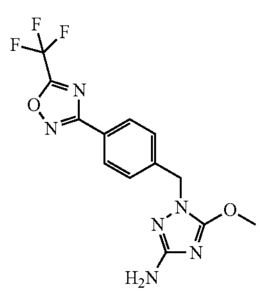 [SMILES: COc1nc(N)nn1Cc1ccc(-c2noc(C(F)(F)F)n2)cc1] | 1.32 | 341.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.216 | 3-[4-[[4-chloro-5-(2,2-difluoro-1,3-benzodioxol-4-yl)-3-methyl-pyrazol-1-yl]methyl]phenyl]-5-(trifluoromethyl)-1,2,4-oxadiazole | 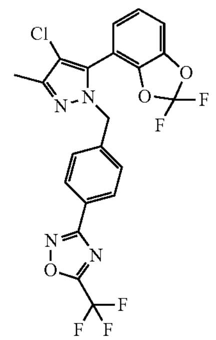 [SMILES: Cc1nn(Cc2ccc(-c3noc(C(F)(F)F)n3)cc2)c(-c2cccc3c2OC(F)(F)O3)c1Cl] | 2.22 | 499.1 | B | |
| 1.217 | 3-[4-[[4-chloro-3-(2,2-difluoro-1,3-benzodioxol-4-yl)-5-methyl-pyrazol-1-yl]methyl]phenyl]-5-(trifluoromethyl)-1,2,4-oxadiazole | 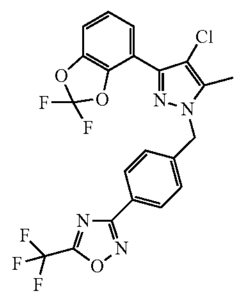 [SMILES: Cc1c(Cl)c(-c2cccc3c2OC(F)(F)O3)nn1Cc1ccc(-c2noc(C(F)(F)F)n2)cc1] | 2.26 | 499.1 | B | |
| 1.218 | 3-(4-chlorophenyl)-1-[[4-[5-(trifluoromethyl)-1,2,4-oxadiazol-3-yl]phenyl]methyl]pyrazole-4-carbonitrile | 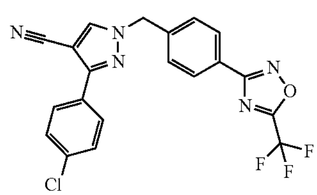 [SMILES: N#Cc1cn(Cc2ccc(-c3noc(C(F)(F)F)n3)cc2)nc1-c1ccc(Cl)cc1] | 2.07 | 430.1 | B | |
| 1.219 | ethyl 2-[1-[[4-[5-(trifluoromethyl)-1,2,4-oxadiazol-3-yl]phenyl]methyl]pyrazol-3-yl]pyridine-3-carboxylate | 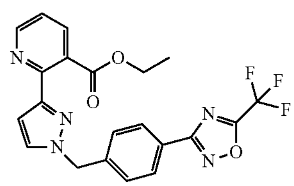 [SMILES: CCOC(=O)c1cccnc1-c1ccn(Cc2ccc(-c3noc(C(F)(F)F)n3)cc2)n1] | 1.72 | 444.2 | B | |
| 1.220 | 3-[4-[[4-chloro-5-(2,4-dichlorophenyl)-3-(trifluoromethyl)pyrazol-1-yl]methyl]phenyl]-5-(trifluoromethyl)-1,2,4-oxadiazole | 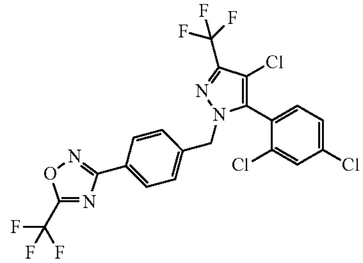 [SMILES: FC(F)(F)c1nc(-c2ccc(Cn3nc(C(F)(F)F)c(Cl)c3-c3ccc(Cl)cc3Cl)cc2)no1] | 2.37 | 541.1 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.221 | 3-[4-[[4-chloro-3-(2,4-dichlorophenyl)-5-(trifluoromethyl)pyrazol-1-yl]methyl]phenyl]-5-(trifluoromethyl)-1,2,4-oxadiazole | 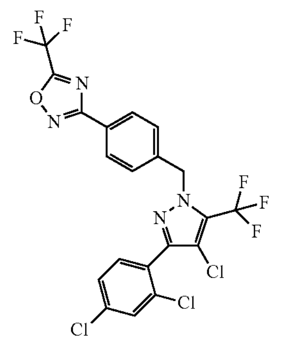 [SMILES: FC(F)(F)c1nc(-c2ccc(Cn3nc(-c4ccc(Cl)cc4Cl)c(Cl)c3C(F)(F)F)cc2)no1] | 2.46 | 541.1 | B | |
| 1.222 | 5-(difluoromethyl)-2-[[4-[5-(trifluoromethyl)-1,2,4-oxadiazol-3-yl]phenyl]methyl]-1,2,4-triazol-3-amine | 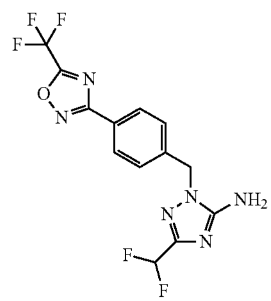 [SMILES: Nc1nc(C(F)F)nn1Cc1ccc(-c2noc(C(F)(F)F)n2)cc1] | 1.38 | 361.1 | B | |
| 1.223 | 5-(4-methoxyphenyl)-2-[[4-[5-(trifluoromethyl)-1,2,4-oxadiazol-3-yl]phenyl]methyl]pyrazole-3-carbaldehyde | 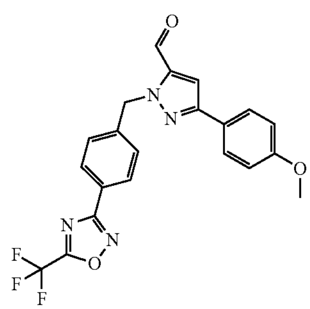 [SMILES: COc1ccc(-c2cc(C=O)n(Cc3ccc(-c4noc(C(F)(F)F)n4)cc3)n2)cc1] | 2.01 | 429.2 | B | |
| 1.224 | ethyl 5-propyl-1-[[4-[5-(trifluoromethyl)-1,2,4-oxadiazol-3-yl]phenyl]methyl]imidazole-4-carboxylate | 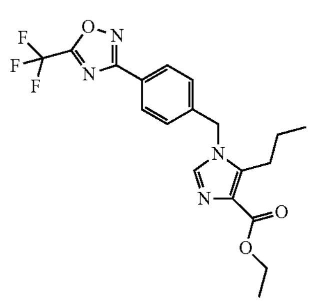 [SMILES: CCCc1c(C(=O)OCC)ncn1Cc1ccc(-c2noc(C(F)(F)F)n2)cc1] | 1.64 | 409.2 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.225 | ethyl 5-propyl-3-[[4-[5-(trifluoromethyl)-1,2,4-oxadiazol-3-yl]phenyl]methyl]imidazole-4-carboxylate | 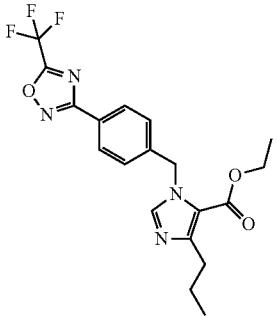 [SMILES: CCCc1ncn(Cc2ccc(-c3noc(C(F)(F)F)n3)cc2)c1C(=O)OCC] | 1.67 | 409.2 | B | |
| 1.226 | 3-[4-(1,2,4-triazol-4-ylmethyl)phenyl]-5-(trifluoromethyl)-1,2,4-oxadiazole | 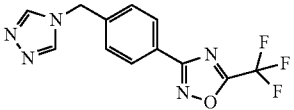 [SMILES: FC(F)(F)c1nc(-c2ccc(Cn3cnnc3)cc2)no1] | 1.13 | 296.1 | B | |
| 1.227 | 4-[2-[[4-[5-(trifluoromethyl)-1,2,4-oxadiazol-3-yl]phenyl]methyl]tetrazol-5-yl]benzaldehyde | 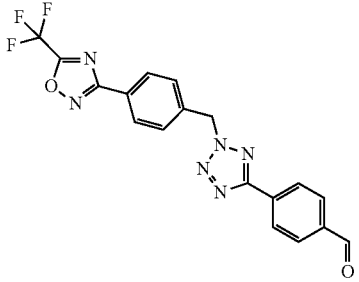 [SMILES: O=Cc1ccc(-c2nnn(Cc3ccc(-c4noc(C(F)(F)F)n4)cc3)n2)cc1] | 1.81 | 401.2 | B | |
| 1.228 | 1-[[4-[5-(trifluoromethyl)-1,2,4-oxadiazol-3-yl]phenyl]methyl]indazole-3-carbonitrile | 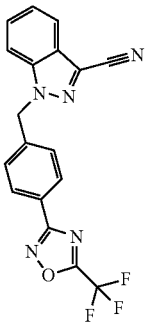 [SMILES: N#Cc1nn(Cc2ccc(-c3noc(C(F)(F)F)n3)cc2)c2ccccc12] | 1.91 | 370.1 | B | |
| 1.229 | 3-[4-[[4-(4-chlorophenyl)imidazol-1-yl]methyl]phenyl]-5-(trifluoromethyl)-1,2,4-oxadiazole | 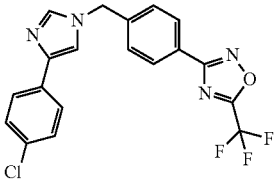 [SMILES: FC(F)(F)c1nc(-c2ccc(Cn3cnc(-c4ccc(Cl)cc4)c3)cc2)no1] | 1.53 | 405.1 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.230 | 3-[4-[[5-(4-chlorophenyl)tetrazol-1-yl]methyl]phenyl]-5-(trifluoromethyl)-1,2,4-oxadiazole | 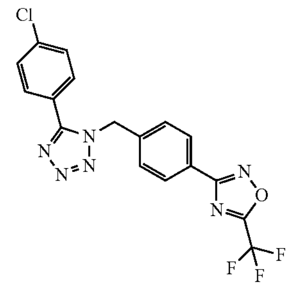 [SMILES: FC(F)(F)c1nc(-c2ccc(Cn3nnnc3-c3ccc(Cl)cc3)cc2)no1] | 1.81 | 407.1 | B | |
| 1.231 | 3-[4-[[5-(4-chlorophenyl)tetrazol-2-yl]methyl]phenyl]-5-(trifluoromethyl)-1,2,4-oxadiazole | 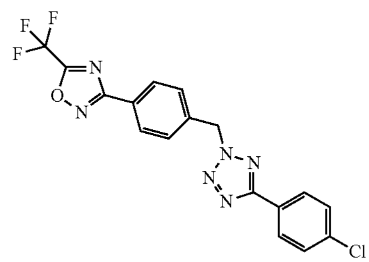 [SMILES: FC(F)(F)c1nc(-c2ccc(Cn3nnc(-c4ccc(Cl)cc4)n3)cc2)no1] | 2.08 | 407.1 | B | |
| 1.232 | 3-[4-[(5-bromo-3-methoxy-1,2,4-triazol-1-yl)methyl]phenyl]-5-(trifluoromethyl)-1,2,4-oxadiazole | 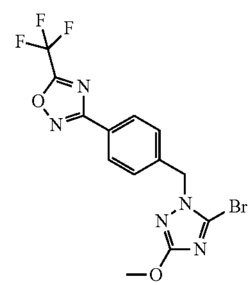 [SMILES: COc1nc(Br)n(Cc2ccc(-c3noc(C(F)(F)F)n3)cc2)n1] | 1.66 | 404.1 | B | |
| 1.233 | 3-[4-[(3-bromo-5-methoxy-1,2,4-triazol-1-yl)methyl]phenyl]-5-(trifluoromethyl)-1,2,4-oxadiazole | 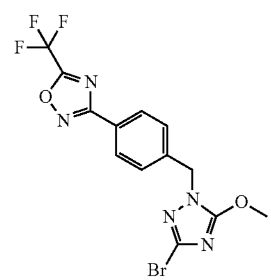 [SMILES: COc1nc(Br)nn1Cc1ccc(-c2noc(C(F)(F)F)n2)cc1] | 1.73 | 404.1 | B | |
| 1.234 | 3-[4-[[5-(4-bromo-3-methylphenyl)tetrazol-1-yl]methyl]phenyl]-5-(trifluoromethyl)-1,2,4-oxadiazole | 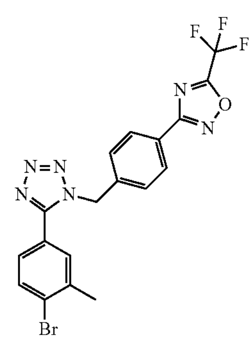 [SMILES: Cc1cc(-c2nnnn2Cc2ccc(-c3noc(C(F)(F)F)n3)cc2)ccc1Br] | 1.94 | 465.1 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]⁺ | LCMS Method | mp (° C.) |
|---|---|---|---|---|---|---|
| 1.235 | 3-[4-[[5-(4-bromo-3-methyl-phenyl)tetrazol-2-yl]methyl]phenyl]-5-(trifluoromethyl)-1,2,4-oxadiazole | 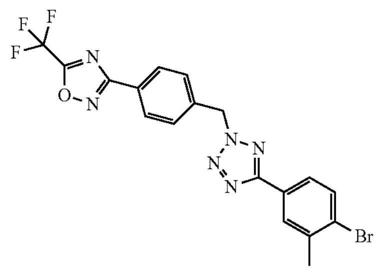 [SMILES: Cc1cc(-c2nnn(Cc3ccc(-c4noc(C(F)(F)F)n4)cc3)n2)ccc1Br] | 2.21 | 465.1 | B | |
| 1.236 | methyl 5-cyclopropyl-1-[[4-[5-(trifluoromethyl)-1,2,4-oxadiazol-3-yl]phenyl]methyl]pyrazole-4-carboxylate | 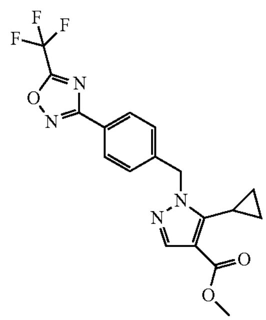 [SMILES: COC(=O)c1cnn(Cc2ccc(-c3noc(C(F)(F)F)n3)cc2)c1C1CC1] | 1.80 | 393.2 | B | |
| 1.237 | methyl 3-cyclopropyl-1-[[4-[5-(trifluoromethyl)-1,2,4-oxadiazol-3-yl]phenyl]methyl]pyrazole-4-carboxylate | 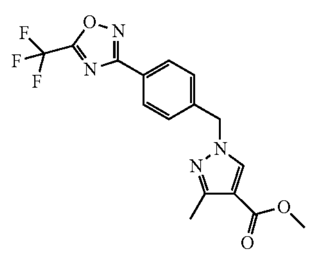 [SMILES: COC(=O)c1cn(Cc2ccc(-c3noc(C(F)(F)F)n3)cc2)nc1C] | 1.85 | 393.2 | B | |
| 1.238 | methyl 3-(methoxymethyl)-1-[[4-[5-(trifluoromethyl)-1,2,4-oxadiazol-3-yl]phenyl]methyl]pyrazole-4-carboxylate | 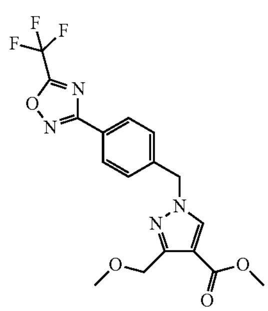 [SMILES: COCc1nn(Cc2ccc(-c3noc(C(F)(F)F)n3)cc2)cc1C(=O)OC] | 1.60 | 397.2 | B | |
| 1.239 | methyl 5-(methoxymethyl)-1-[[4-[5-(trifluoromethyl)-1,2,4-oxadiazol-3-yl]phenyl]methyl]pyrazole-4-carboxylate | 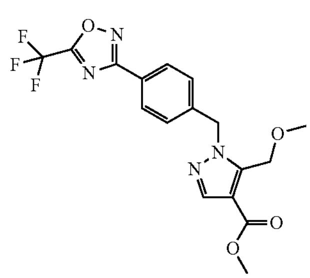 [SMILES: COCc1c(C(=O)OC)cnn1Cc1ccc(-c2noc(C(F)(F)F)n2)cc1] | 1.73 | 397.2 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.240 | 5-(2,6-difluorophenyl)-1-[[4-[5-(trifluoromethyl)-1,2,4-oxadiazol-3-yl]phenyl]methyl]triazole-4-carbonitrile | 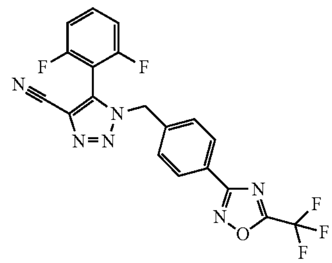 [SMILES: N#Cc1nnn(Cc2ccc(-c3noc(C(F)(F)F)n3)cc2)c1-c1c(F)cccc1F] | 1.84 | 433.0 | B | |
| 1.241 | 5-(2,6-difluorophenyl)-2-[[4-[5-(trifluoromethyl)-1,2,4-oxadiazol-3-yl]phenyl]methyl]triazole-4-carbonitrile | 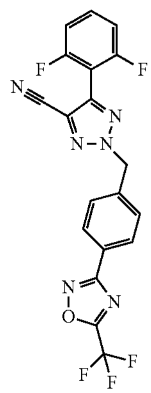 [SMILES: N#Cc1nn(Cc2ccc(-c3noc(C(F)(F)F)n3)cc2)nc1-c1c(F)cccc1F] | 1.98 | 433.1 | B | |
| 1.242 | ethyl 3-(trifluoromethyl)-1-[[4-[5-(trifluoromethyl)-1,2,4-oxadiazol-3-yl]phenyl]methyl]pyrazole-4-carboxylate | 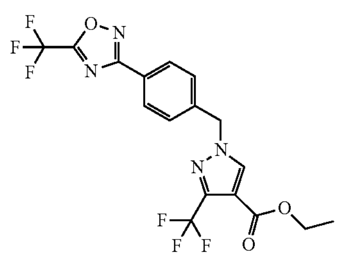 [SMILES: CCOC(=O)c1cn(Cc2ccc(-c3noc(C(F)(F)F)n3)cc2)nc1C(F)(F)F] | 1.93 | 435.2 | B | |
| 1.243 | 3-[4-[(3-chloropyrazol-1-yl)methyl]phenyl]-5-(trifluoromethyl)-1,2,4-oxadiazole | 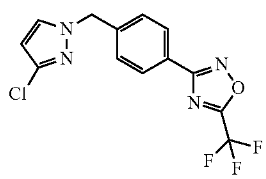 [SMILES: FC(F)(F)c1nc(-c2ccc(Cn3ccc(Cl)n3)cc2)no1] | 1.75 | 329.1 | B | |
| 1.244 | 3-[4-(triazolo[4,5-b]pyridin-4-ylmethyl)phenyl]-5-(trifluoromethyl)-1,2,4-oxadiazole | 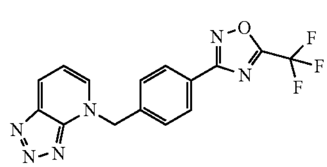 [SMILES: FC(F)(F)c1nc(-c2ccc(Cn3cccc4nnnc3-4)cc2)no1] | 1.11 | 347.1 | B | |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.245 | 3-[4-(triazolo[4,5-b]pyridin-1-ylmethyl)phenyl]-5-(trifluoromethyl)-1,2,4-oxadiazole | 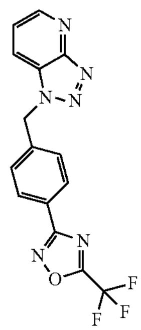 [SMILES: FC(F)(F)c1nc(-c2ccc(Cn3nnc4ncccc43)cc2)no1] | 1.42 | 347.1 | B | |
| 1.246 | 3-[4-(triazolo[4,5-b]pyridin-2-ylmethyl)phenyl]-5-(trifluoromethyl)-1,2,4-oxadiazole | 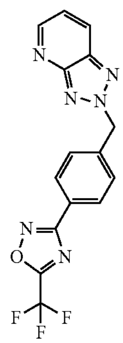 [SMILES: FC(F)(F)c1nc(-c2ccc(Cn3nc4cccnc4n3)cc2)no1] | 1.56 | 347.1 | B | |
| 1.247 | 3-[4-(triazolo[4,5-b]pyridin-3-ylmethyl)phenyl]-5-(trifluoromethyl)-1,2,4-oxadiazole | 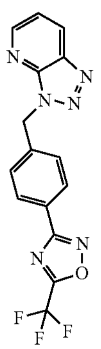 [SMILES: FC(F)(F)c1nc(-c2ccc(Cn3nnc4cccnc43)cc2)no1] | 1.60 | 347.1 | B | |
| 1.248 | methyl 1-[[4-[5-(trifluoromethyl)-1,2,4-oxadiazol-3-yl]phenyl]methyl]pyrazole-4-carboxylate | 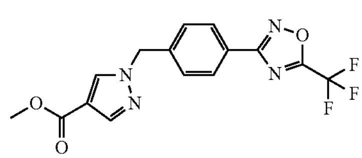 [SMILES: COC(=O)c1cnn(Cc2ccc(-c3noc(C(F)(F)F)n3)cc2)c1] | | | | 122-129 |
| 1.249 | N-(cyclopropylmethyl)-1-[[4-[5-(trifluoromethyl)-1,2,4-oxadiazol-3-yl]phenyl]methyl]pyrazole-4-carboxamide | 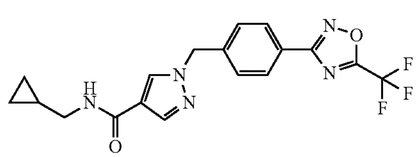 [SMILES: O=C(NCC1CC1)c1cnn(Cc2ccc(-c3noc(C(F)(F)F)n3)cc2)c1] | | | | 195-200 |
| 1.250 | N-(2-methoxyethyl)-1-[[4-[5-(trifluoromethyl)-1,2,4-oxadiazol-3-yl]phenyl]methyl]pyrazole-4-carboxamide | 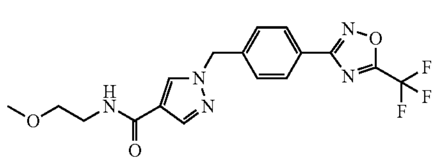 [SMILES: COCCNC(=O)c1cnn(Cc2ccc(-c3noc(C(F)(F)F)n3)cc2)c1] | | | | 132-142 |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.251 | N-prop-2-ynyl-1-[[4-[5-(trifluoromethyl)-1,2,4-oxadiazol-3-yl]phenyl]methyl]pyrazole-4-carboxamide | 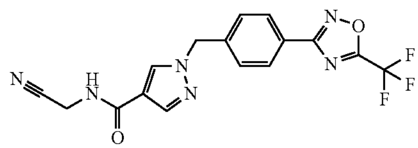 [SMILES: N#CCNC(=O)c1cnn(Cc2ccc(-c3noc(C(F)(F)F)n3)cc2)c1] | | | | 145-155 |
| 1.252 | ethyl 1-[[3-fluoro-4-[5-(trifluoromethyl)-1,2,4-oxadiazol-3-yl]phenyl]methyl]pyrazole-4-carboxylate | 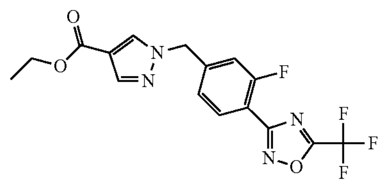 [SMILES: CCOC(=O)c1cnn(Cc2ccc(-c3noc(C(F)(F)F)n3)c(F)c2)c1] | | | | 131-135 |
| 1.253 | 3-[4-[(3,5-dimethylpyrazol-1-yl)methyl]-2-fluoro-phenyl]-5-(trifluoromethyl)-1,2,4-oxadiazole | 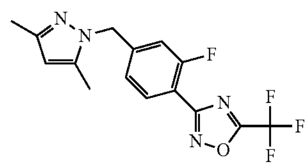 [SMILES: Cc1cc(C)n(Cc2ccc(-c3noc(C(F)(F)F)n3)c(F)c2)n1] | 1.08 | 341 | A | |
| 1.254 | 3-[4-[(6-methoxy-3-pyridyl)methyl]phenyl]-5-(trifluoromethyl)-1,2,4-oxadiazole | 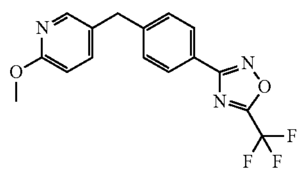 [SMILES: COc1ccc(Cc2ccc(-c3noc(C(F)(F)F)n3)cc2)cn1] | | | A | |
| 1.255 | 1-[[3-fluoro-4-[5-(trifluoromethyl)-1,2,4-oxadiazol-3-yl]phenyl]methyl]-1,2,4-triazole-3-carbonitrile | 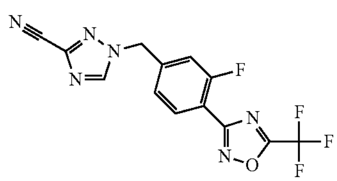 [SMILES: N#Cc1ncn(Cc2ccc(-c3noc(C(F)(F)F)n3)c(F)c2)n1] | | | | 120-123 |
| 1.256 | 2-[[3-fluoro-4-[5-(trifluoromethyl)-1,2,4-oxadiazol-3-yl]phenyl]methyl]-1,2,4-triazole-3-carbonitrile | 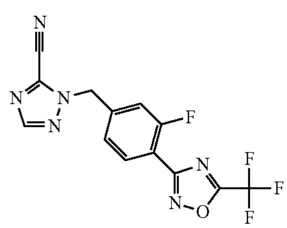 [SMILES: N#Cc1ncnn1Cc1ccc(-c2noc(C(F)(F)F)n2)c(F)c1] | 1.03 | 337 (M − H) | A | |
| 1.257 | 1-[[6-[5-(trifluoromethyl)-1,2,4-oxadiazol-3-yl]-3-pyridyl]methyl]-1,2,4-triazole-3-carbonitrile | 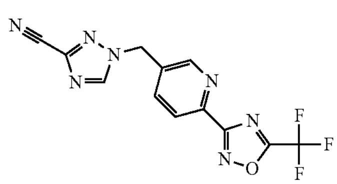 [SMILES: N#Cc1ncn(Cc2ccc(-c3noc(C(F)(F)F)n3)nc2)n1] | | | | 105-108 |
| 1.258 | 2-[[6-[5-(trifluoromethyl)-1,2,4-oxadiazol-3-yl]-3-pyridyl]methyl]-1,2,4-triazole-3-carbonitrile | 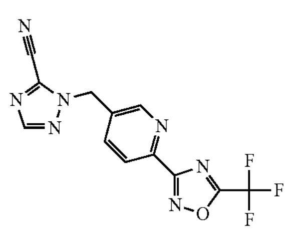 [SMILES: N#Cc1ncnn1Cc1ccc(-c2noc(C(F)(F)F)n2)nc1] | 0.89 | 322 | A | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.259 | N,N-diethyl-1-[[4-[5-(trifluoromethyl)-1,2,4-oxadiazol-3-yl]phenyl]methyl]pyrazole-4-carboxamide | 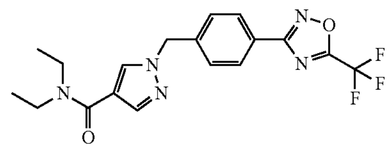 [SMILES: CCN(CC)C(=O)c1cnn(Cc2ccc(-c3noc(C(F)(F)F)n3)cc2)c1] | | | | 86-96 |
| 1.260 | N-methoxy-N-methyl-1-[[4-[5-(trifluoromethyl)-1,2,4-oxadiazol-3-yl]phenyl]methyl]pyrazole-4-carboxamide | 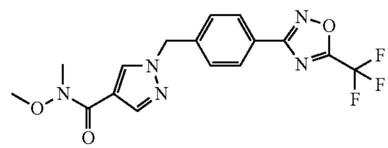 [SMILES: CON(C)C(=O)c1cnn(Cc2ccc(-c3noc(C(F)(F)F)n3)cc2)c1] | | | | 102-112 |
| 1.261 | morpholino-[1-[[4-[5-(trifluoromethyl)-1,2,4-oxadiazol-3-yl]phenyl]methyl]pyrazol-4-yl]methanone | 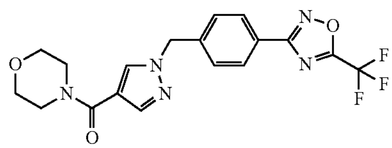 [SMILES: O=C(c1cnn(Cc2ccc(-c3noc(C(F)(F)F)n3)cc2)c1)N1CCOCC1] | | | | 125-135 |
| 1.262 | ~{tert}-butyl 1-[[4-[5-(trifluoromethyl)-1,2,4-oxadiazol-3-yl]phenyl]methyl]pyrazole-4-carboxylate | 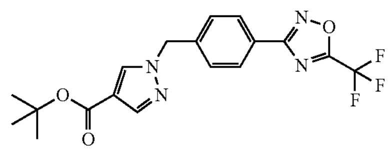 [SMILES: CC(C)(C)OC(=O)c1cnn(Cc2ccc(-c3noc(C(F)(F)F)n3)cc2)c1] | | | | 81-91 |
| 1.263 | isopropyl 1-[[4-[5-(trifluoromethyl)-1,2,4-oxadiazol-3-yl]phenyl]methyl]pyrazole-4-carboxylate | 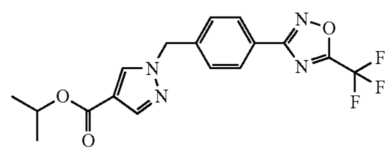 [SMILES: CC(C)OC(=O)c1cnn(Cc2ccc(-c3noc(C(F)(F)F)n3)cc2)c1] | 1.13 | 381 | A | |
| 1.264 | propyl 1-[[4-[5-(trifluoromethyl)-1,2,4-oxadiazol-3-yl]phenyl]methyl]pyrazole-4-carboxylate | 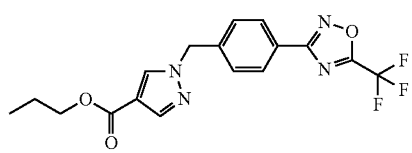 [SMILES: CCCOC(=O)c1cnn(Cc2ccc(-c3noc(C(F)(F)F)n3)cc2)c1] | | | | 105-115 |
| 1.265 | 2-(dimethylamino)ethyl 1-[[4-[5-(trifluoromethyl)-1,2,4-oxadiazol-3-yl]phenyl]methyl]pyrazole-4-carboxylate | 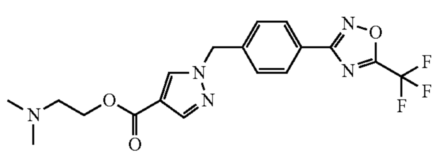 [SMILES: CN(C)CCOC(=O)c1cnn(Cc2ccc(-c3noc(C(F)(F)F)n3)cc2)c1] | | | | 60-70 |
| 1.266 | ~{N}-methoxy-1-[[4-[5-(trifluoromethyl)-1,2,4-oxadiazol-3-yl]phenyl]methyl]pyrazole-4-carboxamide | 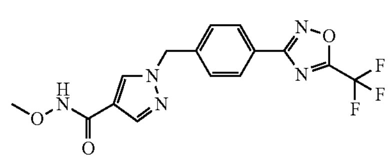 [SMILES: CONC(=O)c1cnn(Cc2ccc(-c3noc(C(F)(F)F)n3)cc2)c1] | | | | 128-138 |
| 1.267 | ~{N}-ethyl-1-[[4-[5-(trifluoromethyl)-1,2,4-oxadiazol-3-yl]phenyl]methyl]pyrazole-4-carboxamide | 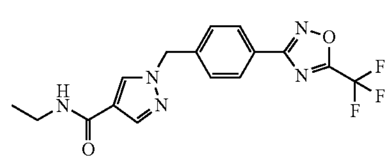 | | | | 166-176 |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.268 | 1-[[4-[5-(trifluoromethyl)-1,2,4-oxadiazol-3-yl]phenyl]methyl] pyrazole-4-carboxamide | 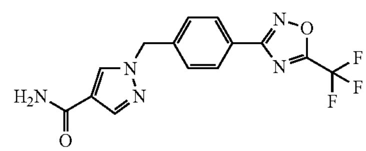 [SMILES: NC(=O)c1cnn(Cc2ccc(-c3noc(C(F)(F)F)n3)cc2)c1] | 0.86 | 338 | A | |
| 1.269 | ethyl 1-[[6-[5-(trifluoromethyl)-1,2,4-oxadiazol-3-yl]-3-pyridyl]methyl] pyrazole-4-carboxylate | 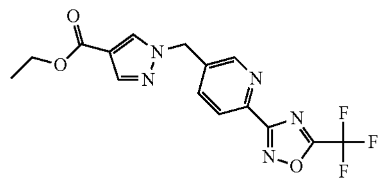 [SMILES: CCOC(=O)c1cnn(Cc2ccc(-c3noc(C(F)(F)F)n3)nc2)c1] | | | | 88-90 |
| 1.270 | methyl 1-[[4-[5-(trifluoromethyl)-1,2,4-oxadiazol-3-yl]phenyl]methyl] triazole-4-carboxylate | 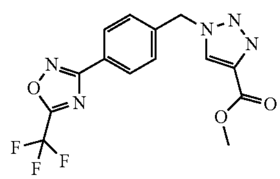 [SMILES: COC(=O)C1=CN(Cc2ccc(-c3noc(C(F)(F)F)n3)cc2)NN1] | | | | 154-156 |
| 1.271 | 1-[[4-[5-(trifluoromethyl)-1,2,4-oxadiazol-3-yl]phenyl]methyl] triazole-4-carboxylic acid | 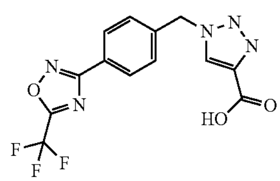 [SMILES: O=C(O)C1=CN(Cc2ccc(-c3noc(C(F)(F)F)n3)cc2)NN1] | | | | 208-210 |
| 1.272 | N-methyl-1-[[4-[5-(trifluoromethyl)-1,2,4-oxadiazol-3-yl]phenyl]methyl] triazole-4-carboxamide | 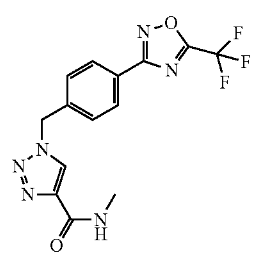 [SMILES: CNC(=O)c1cn(Cc2ccc(-c3noc(C(F)(F)F)n3)cc2)nn1] | 0.92 | 352 | C | |
| 1.273 | 1-[[4-[5-(trifluoromethyl)-1,2,4-oxadiazol-3-yl]phenyl]methyl] pyrazole-4-carbaldehyde | 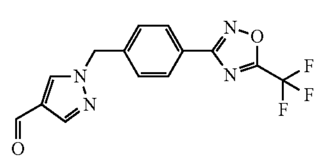 [SMILES: O=Cc1cnn(Cc2ccc(-c3noc(C(F)(F)F)n3)cc2)c1] | | | | 91-96 |
| 1.274 | N-ethyl-1-[[4-(5-(trifluoromethyl)-1,2,4-oxadiazol-3-yl]phenyl]methyl] triazole-4-carboxamide | 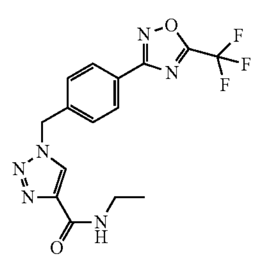 | | | | 193-195 |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.275 | N-methoxy-N-methyl-1-[[4-[5-(trifluoromethyl)-1,2,4-oxadiazol-3-yl]phenyl]methyl]triazole-4-carboxamide | 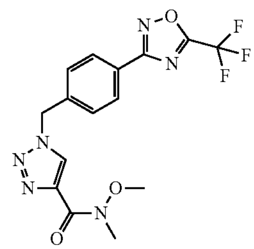 [SMILES: CON(C)C(=O)c1cn(Cc2ccc(-c3noc(C(F)(F)F)n3)cc2)nn1] | | | | 135-137 |
| 1.276 | ethyl 1-[[4-[5-(trifluoromethyl)-1,2,4-oxadiazol-3-yl]phenyl]methyl]triazole-4-carboxylate | 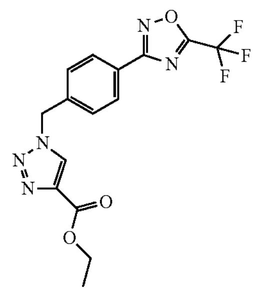 [SMILES: CCOC(=O)c1cn(Cc2ccc(-c3noc(C(F)(F)F)n3)cc2)nn1] | | | | 134-136 |
| 1.277 | N-methoxy-1-[[4-[5-(trifluoromethyl)-1,2,4-oxadiazol-3-yl]phenyl]methyl]triazole-4-carboxamide | 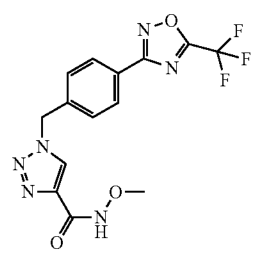 [SMILES: CONC(=O)c1cn(Cc2ccc(-c3noc(C(F)(F)F)n3)cc2)nn1] | | | | 198-200 |
| 1.278 | isopropyl 1-[[4-[5-(trifluoromethyl)-1,2,4-oxadiazol-3-yl]phenyl]methyl]triazole-4-carboxylate | 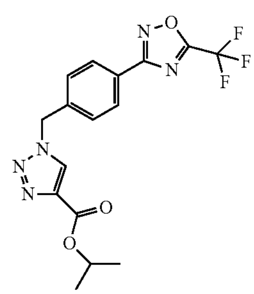 [SMILES: CC(C)OC(=O)c1cn(Cc2ccc(-c3noc(C(F)(F)F)n3)cc2)nn1] | | | | 146-148 |
| 1.279 | methyl 3-[[4-[5-(trifluoromethyl)-1,2,4-oxadiazol-3-yl]phenyl]methyl]triazole-4-carboxylate | 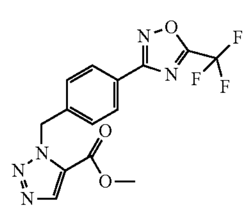 [SMILES: COC(=O)c1cnnn1Cc1ccc(-c2noc(C(F)(F)F)n2)cc1] | | | | 103-107 |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.280 | N,N-dimethyl-1-[[4-[5-(trifluoromethyl)-1,2,4-oxadiazol-3-yl]phenyl]methyl]triazole-4-carboxamide | 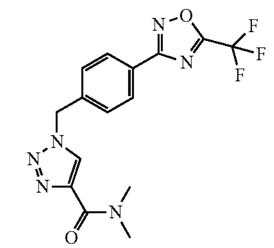 [SMILES: CN(C)C(=O)c1cn(Cc2ccc(-c3noc(C(F)(F)F)n3)cc2)nn1] | | | | 168-170 |
| 1.281 | N-(4-methoxyphenyl)-1-[[4-[5-(trifluoromethyl)-1,2,4-oxadiazol-3-yl]phenyl]methyl]triazole-4-carboxamide | 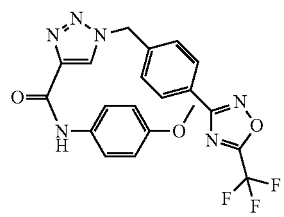 [SMILES: COc1ccc(NC(=O)c2cn(Cc3ccc(-c4noc(C(F)(F)F)n4)cc3)nn2)cc1] | | | | 205-207 |
| 1.282 | N-(4-chlorophenyl)-1-[[4-[5-(trifluoromethyl)-1,2,4-oxadiazol-3-yl]phenyl]methyl]triazole-4-carboxamide | 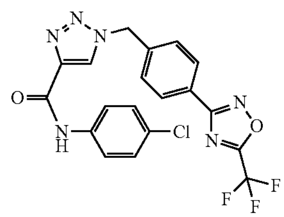 | | | | 233-235 |
| 1.283 | N-(4-pyridyl)-1-[[4-[5-(trifluoromethyl)-1,2,4-oxadiazol-3-yl]phenyl]methyl]triazole-4-carboxamide | 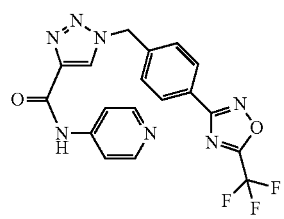 [SMILES: O=C(Nc1ccncc1)c1cn(Cc2ccc(-c3noc(C(F)(F)F)n3)cc2)nn1] | | | | 204-206 |
| 1.284 | 3-[5-[(3,5-dimethylpyrazol-1-yl)methyl]-2-pyridyl]-5-(trifluoromethyl)-1,2,4-oxadiazole | 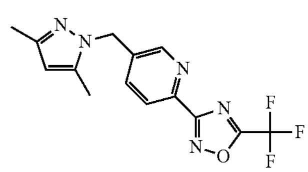 [SMILES: Cc1cc(C)n(Cc2ccc(-c3noc(C(F)(F)F)n3)nc2)n1] | 0.95 | 324 | A | |
| 1.285 | N-methoxy-1-1-[[4-[5-(trifluoromethyl)-1,2,4-oxadiazol-3-yl]phenyl]methyl]pyrazol-4-yl]methanimine | 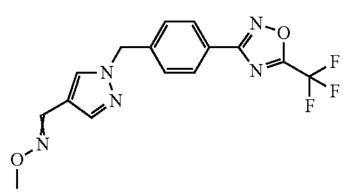 [SMILES: CON=Cc1cnn(Cc2ccc(-c3noc(C(F)(F)F)n3)cc2)c1] | | | | 88-98 |
| 1.286 | N-ethoxy-1-[1-[[4-[5-(trifluoromethyl)-1,2,4-oxadiazol-3-yl]phenyl]methyl]pyrazol-4-yl]methanimine | 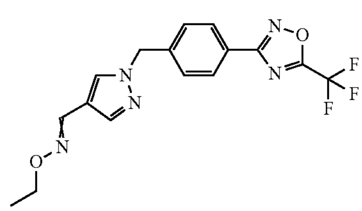 [SMILES: CCON=Cc1cnn(Cc2ccc(-c3noc(C(F)(F)F)n3)cc2)c1] | | | | 80-120 |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.287 | N-propoxy-1-[1-[[4-[5-(trifluoromethyl)-1,2,4-oxadiazol-3-yl]phenyl]methyl]pyrazol-4-yl]methanimine | 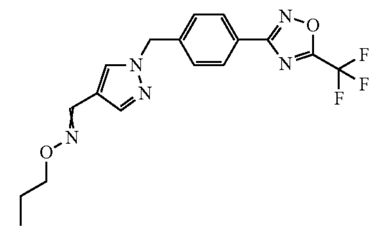 [SMILES: CCCON=Cc1cnn(Cc2ccc(-c3noc(C(F)(F)F)n3)cc2)c1] | | | | 60-95 |
| 1.288 | N-isopropoxy-1-[1-[[4-[5-(trifluoromethyl)-1,2,4-oxadiazol-3-yl]phenyl]methyl]pyrazol-4-yl]methanimine | 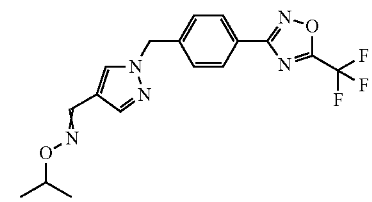 [SMILES: CC(C)ON=Cc1cnn(Cc2ccc(-c3noc(C(F)(F)F)n3)cc2)c1] | 1.14; 1.16 | Mass not detected | A | |
| 1.289 | N-benzyloxy-1-[1-[[4-[5-(trifluoromethyl)-1,2,4-oxadiazol-3-yl]phenyl]methyl]pyrazol-4-yl]methanimine | 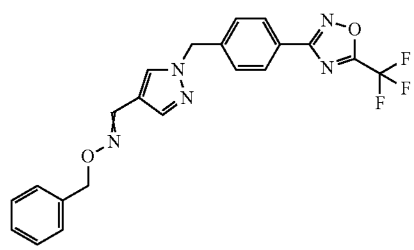 [SMILES: FC(F)(F)c1nc(-c2ccc(Cn3cc(C=NOCc4ccccc4)cn3)cc2)no1] | | | | 75-85 |
| 1.290 | N-prop-2-ynoxy-1-[1-[[4-[5-(trifluoromethyl)-1,2,4-oxadiazol-3-yl]phenyl]methyl]pyrazol-4-yl]methanimine | 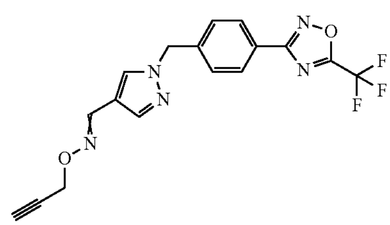 [SMILES: C#CCON=Cc1cnn(Cc2ccc(-c3noc(C(F)(F)F)n3)cc2)c1] | | | | 57-63 |
| 1.291 | N-methyl-3-[[4-[5-(trifluoromethyl)-1,2,4-oxadiazol-3-yl]phenyl]methyl]triazole-4-carboxamide | 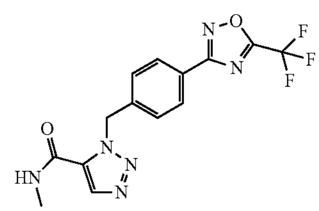 [SMILES: CNC(=O)c1cnnn1Cc1ccc(-c2noc(C(F)(F)F)n2)cc1] | | | | 222-224 |
| 1.292 | N-methoxy-1-[[4-[5-(trifluoromethyl)-1,2,4-oxadiazol-3-yl]phenyl]methyl]pyrrolidin-3-imine | 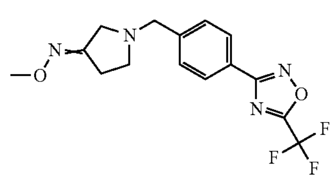 [SMILES: CON=C1CCN(Cc2ccc(-c3noc(C(F)(F)F)n3)cc2)C1] | 1.10 | 341 | B | |
| 1.293 | N-methoxy-1-[[4-[5-(trifluoromethyl)-1,2,4-oxadiazol-3-yl]phenyl]methyl]piperidin-4-imine | 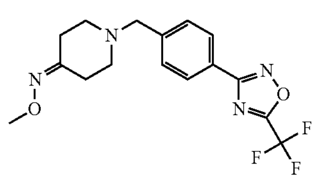 [SMILES: CON=C1CCN(Cc2ccc(-c3noc(C(F)(F)F)n3)cc2)CC1] | 1.04 | 355 | B | |

TABLE T1-continued

Melting point (mp) and/or LC/MS data (retention time ($t_R$)) for compounds of Formula (I):

| Entry | Compound name | Structure | $t_R$ (min) | Mass charge $[M + H]^+$ | LCMS Method | mp (° C.) |
|---|---|---|---|---|---|---|
| 1.294 | 3-[4-[(5-methylsulfonyl-1,2,4-triazol-1-yl)methyl]phenyl]-5-(trifluoromethyl)-1,2,4-oxadiazole | 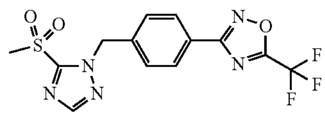 [SMILES: CS(=O)(=O)c1ncnn1Cc1ccc(-c2noc(C(F)(F)F)n2)cc1] | | | | 119.2-119.8 |
| 1.295 | 3-[4-[(5-methylsulfinyl-1,2,4-triazol-1-yl)methyl]phenyl]-5-(trifluoromethyl)-1,2,4-oxadiazole | 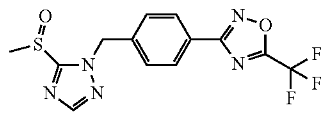 [SMILES: CS(=O)c1ncnn1Cc1ccc(-c2noc(C(F)(F)F)n2)cc1] | | | | 71.2-73.7 |
| 1.296 | 3-[4-[(3-methylsulfonyl-1,2,4-triazol-1-yl)methyl]phenyl]-5-(trifluoromethyl)-1,2,4-oxadiazole | 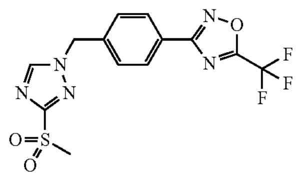 [SMILES: CS(=O)(=O)c1ncn(Cc2ccc(-c3noc(C(F)(F)F)n3)cc2)n1] | | | | 145.4-146.4 |
| 1.297 | 3-[4-[(3-methylsulfinyl-1,2,4-triazol-1-yl)methyl]phenyl]-5-(trifluoromethyl)-1,2,4-oxadiazole | 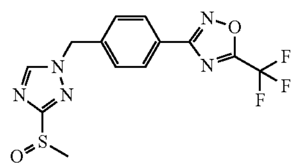 [SMILES: CS(=O)c1ncn(Cc2ccc(-c3noc(C(F)(F)F)n3)cc2)n1] | | | | 114.4-115.2 |
| 1.298 | 3-[4-[(5-methylsulfanyl-1,2,4-triazol-1-yl)methyl]phenyl]-5-(trifluoromethyl)-1,2,4-oxadiazole | 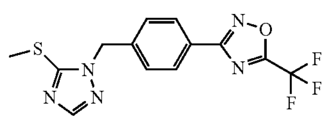 [SMILES: CSc1ncnn1Cc1ccc(-c2noc(C(F)(F)F)n2)cc1] | | | | 72-73.2 |
| 1.299 | 3-[4-[(3-methylsulfanyl-1,2,4-triazol-1-yl)methyl]phenyl]-5-(trifluoromethyl)-1,2,4-oxadiazole | 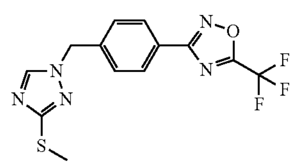 [SMILES: CSc1ncn(Cc2ccc(-c3noc(C(F)(F)F)n3)cc2)n1] | | | | 88-90.4 |
| 1.300 | 3-[4-(1-piperidylmethyl)phenyl]-5-(trifluoromethyl)-1,2,4-oxadiazole | 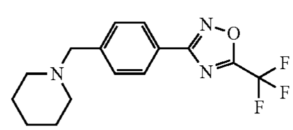 [SMILES: FC(F)(F)c1nc(-c2ccc(CN3CCCCC3)cc2)no1] | 0.75 | 313 | A | |
| 1.301 | 4-[[4-[5-(trifluoromethyl)-1,2,4-oxadiazol-3-yl]phenyl]methyl]morpholine | 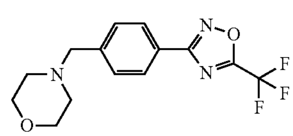 [SMILES: FC(F)(F)c1nc(-c2ccc(CN3CCOCC3)cc2)no1] | 0.68 | 315 | A | |
| 1.302 | 3-[4-(thiomorpholino-methyl)phenyl]-5-(trifluoromethyl)-1,2,4-oxadiazole | 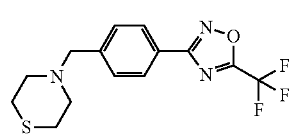 [SMILES: FC(F)(F)c1nc(-c2ccc(CN3CCSCC3)cc2)no1] | | | | 54.5-56.6 |

TABLE T1-continued

Melting point (mp) and/or LC/MS data (retention time ($t_R$)) for compounds of Formula (I):

| Entry | Compound name | Structure | $t_R$ (min) | Mass charge [M + H]+ | LCMS Method | mp (° C.) |
|---|---|---|---|---|---|---|
| 1.303 | 3-[4-[1-(3,5-dimethylpyrazol-1-yl)ethyl]phenyl]-5-(trifluoromethyl)-1,2,4-oxadiazole | 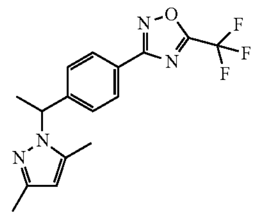 [SMILES: Cc1cc(C)n(C(C)c2ccc(-c3noc(C(F)(F)F)n3)cc2)n1] | 1.61 | 337 | C | |
| 1.304 | ethyl 1-[1-[4-[5-(trifluoromethyl)-1,2,4-oxadiazol-3-yl]phenyl]ethyl]pyrazole-4-carboxylate | 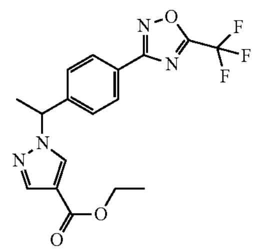 [SMILES: CCOC(=O)c1cnn(C(C)c2ccc(-c3noc(C(F)(F)F)n3)cc2)c1] | 1.61 | 381 | C | |
| 1.305 | 3-[4-[(4-methylsulfonyl-piperazin-1-yl)methyl]phenyl]-5-(trifluoromethyl)-1,2,4-oxadiazole | 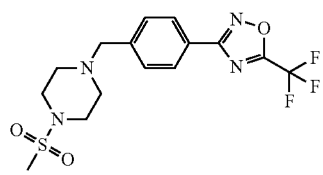 [SMILES: CS(=O)(=O)N1CCN(Cc2ccc(-c3noc(C(F)(F)F)n3)cc2)CC1] | | | | 111.1-114.9 |
| 1.306 | 2,6-dimethyl-4-[[4-[5-(trifluoromethyl)-1,2,4-oxadiazol-3-yl]phenyl]methyl]morpholine | 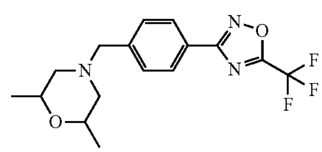 [SMILES: CC1CN(Cc2ccc(-c3noc(C(F)(F)F)n3)cc2)CC(C)O1] | 0.76; 0.81 | 343 | A | |
| 1.307 | (2R,6S)-2,6-dimethyl-4-[[4-[5-(trifluoromethyl)-1,2,4-oxadiazol-3-yl]phenyl]methyl]morpholine | 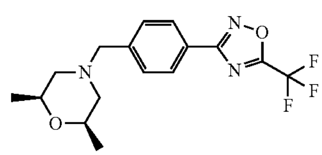 [SMILES: C[C@@H]1CN(Cc2ccc(-c3noc(C(F)(F)F)n3)cc2)C[C@H](C)O1] | 0.76 | 343 | A | |
| 1.308 | (2R,6R)-2,6-dimethyl-4-[[4-[5-(trifluoromethyl)-1,2,4-oxadiazol-3-yl]phenyl]methyl]morpholine | 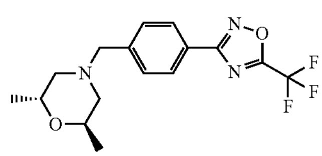 [SMILES: C[C@@H]1CN(Cc2ccc(-c3noc(C(F)(F)F)n3)cc2)C[C@@H](C)O1] | 0.81 | 343 | A | |
| 1.309 | 3-[4-[2-(3,5-dimethylpyrazol-1-yl)ethyl]phenyl]-5-(trifluoromethyl)-1,2,4-oxadiazole | 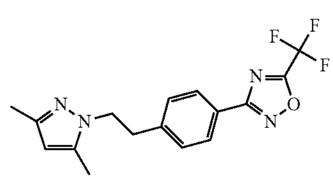 [SMILES: Cc1cc(C)n(CCc2ccc(-c3noc(C(F)(F)F)n3)cc2)n1] | 1.67 | 337 | C | |
| 1.310 | ethyl 1-[2-[4-[5-(trifluoromethyl)-1,2,4-oxadiazol-yl]phenyl]ethyl]pyrazole-4-carboxylate | 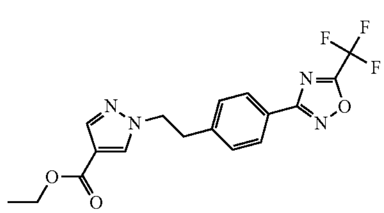 [SMILES: CCOC(=O)c1cnn(CCc2ccc(-c3noc(C(F)(F)F)n3)cc2)c1] | 1.57 | 381 | C | 108-110 |

TABLE T1-continued

Melting point (mp) and/or LC/MS data (retention time ($t_R$)) for compounds of Formula (I):

| Entry | Compound name | Structure | $t_R$ (min) | Mass charge [M + H]$^+$ | LCMS Method | mp (° C.) |
|---|---|---|---|---|---|---|
| 1.311 | ethyl 1-[2-fluoro-2-[4-[5-(trifluoromethyl)-1,2,4-oxadiazol-3-yl]phenyl]ethyl]pyrazole-4-carboxylate | 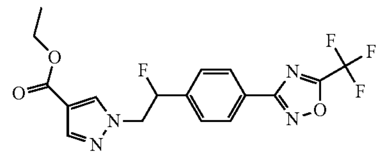 [SMILES: CCOC(=O)c1cnn(CC(F)c2ccc(-c3noc(C(F)(F)F)n3)cc2)c1] | | | | 145-147 |
| 1.312 | 2-morpholino-2-[4-[5-(trifluoromethyl)-1,2,4-oxadiazol-3-yl]phenyl]acetonitrile | 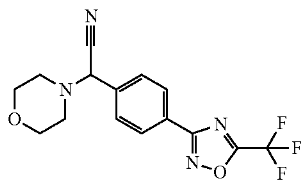 [SMILES: N#CC(c1ccc(-c2noc(C(F)(F)F)n2)cc1)N1CCOCC1] | 1.07 | 339 | A | |

BIOLOGICAL EXAMPLES

General Examples of Leaf Disk Tests in Well Plates:

Leaf disks or leaf segments of various plant species are cut from plants grown in a greenhouse. The cut leaf disks or segments are placed in multiwell plates (24-well format) onto water agar. The leaf disks are sprayed with a test solution before (preventative) or after (curative) inoculation. Compounds to be tested are prepared as DMSO solutions (max. 10 mg/ml) which are diluted to the appropriate concentration with 0.025% Tween20 just before spraying. The inoculated leaf disks or segments are incubated under defined conditions (temperature, relative humidity, light, etc.) according to the respective test system. A single evaluation of disease level is carried out 3 to 14 days after inoculation, depending on the pathosystem. Percent disease control relative to the untreated check leaf disks or segments is then calculated.

General Examples of Liquid Culture Tests in Well Plates:

Mycelia fragments or conidia suspensions of a fungus prepared either freshly from liquid cultures of the fungus or from cryogenic storage, are directly mixed into nutrient broth. DMSO solutions of the test compound (max. 10 mg/ml) are diluted with 0.025% Tween20 by a factor of 50 and 10 µl of this solution is pipetted into a microtiter plate (96-well format). The nutrient broth containing the fungal spores/mycelia fragments is then added to give an end concentration of the tested compound. The test plates are incubated in the dark at 24° C. and 96% relative humidity. The inhibition of fungal growth is determined photometrically after 2 to 7 days, depending on the pathosystem, and percent antifungal activity relative to the untreated check is calculated.

Example 1: Fungicidal Activity Against *Puccinia recondita* f. Sp. *Tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% relative humidity (rh) under a light regime of 12 hours light/12 hours darkness in a climate cabinet and the activity of a compound was assessed as percent disease control compared to untreated when an appropriate level of disease damage appears in untreated check leaf segments (7 to 9 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.4, 1.5, 1.6, 1.7, 1.8, 1.9, 1.10, 1.11, 1.12, 1.15, 1.16, 1.18, 1.19, 1.21, 1.22, 1.23, 1.24, 1.25, 1.26, 1.27, 1.28, 1.29, 1.30, 1.32, 1.33, 1.34, 1.35, 1.36, 1.37, 1.39, 1.40, 1.41, 1.42, 1.43, 1.44, 1.45, 1.46, 1.47, 1.48, 1.49, 1.50, 1.52, 1.53, 1.55, 1.56, 1.57, 1.58, 1.60, 1.61, 1.62, 1.63, 1.65, 1.67, 1.73, 1.74, 1.75, 1.76, 1.79, 1.80, 1.81, 1.82, 1.83, 1.85, 1.86, 1.87, 1.88, 1.89, 1.90, 1.91, 1.93, 1.94, 1.95, 1.96, 1.99, 1.101, 1.102, 1.105, 1.107, 1.108, 1.109, 1.112, 1.118, 1.119, 1.120, 1.121, 1.122, 1.123, 1.124, 1.125, 1.126, 1.128, 1.129, 1.131, 1.132, 1.133, 1.135, 1.136, 1.137, 1.139, 1.141, 1.144, 1.145, 1.146, 1.147, 1.148, 1.149, 1.150, 1.151, 1.154, 1.156, 1.157, 1.158, 1.171, 1.174, 1.186, 1.192, 1.193, 1.200, 1.203, 1.204, 1.206, 1.207, 1.208, 1.209, 1.212, 1.213, 1.214, 1.215, 1.219, 1.222, 1.224, 1.226, 1.229, 1.232, 1.233, 1.236, 1.237, 1.238, 1.239, 1.240, 1.243, 1.244, 1.245, 1.246, 1.247, 1.248, 1.249, 1.250, 1.251, 1.252, 1.253, 1.254, 1.255, 1.256, 1.259, 1.260, 1.261, 1.262, 1.263, 1.265, 1.266, 1.267, 1.268, 1.269, 1.270, 1.271, 1.273, 1.274, 1.275, 1.276, 1.277, 1.278, 1.279, 1.280, 1.281, 1.282, 1.283, 1.285, 1.286, 1.287, 1.288, 1.289, 1.290, 1.292, 1.294, 1.295, 1.296, 1.297, 1.298, 1.299, 1.301, 1.302, 1.303, 1.304, 1.305, 1.306, 1.308, 1.310 and 1.312.

Example 2: Fungicidal Activity Against *Puccinia recondita* f. Sp. *Tritici*/Wheat/Leaf Disc Curative (Brown Rust)

Wheat leaf segments cv. Kanzler are placed on agar in multiwell plates (24-well format). The leaf segments are then inoculated with a spore suspension of the fungus. Plates were stored in darkness at 19° C. and 75% relative humidity. The formulated test compound diluted in water was applied 1 day after inoculation. The leaf segments were incubated at 19° C. and 75% relative humidity under a light regime of 12 hours light/12 hours darkness in a climate cabinet and the activity of a compound was assessed as percent disease control compared to untreated when an appropriate level of disease damage appears in untreated check leaf segments (6 to 8 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.5, 1.6, 1.8, 1.9, 1.10, 1.11, 1.15, 1.16, 1.18, 1.19, 1.22, 1.23, 1.25, 1.26, 1.27, 1.30, 1.32, 1.33, 1.34, 1.35, 1.36, 1.38, 1.39, 1.40, 1.41, 1.42, 1.43, 1.44, 1.45, 1.46, 1.49, 1.54, 1.55, 1.56, 1.61, 1.62, 1.67, 1.71, 1.76, 1.77, 1.78, 1.79, 1.80, 1.81, 1.82, 1.83, 1.85, 1.86, 1.87, 1.88, 1.89, 1.90, 1.91, 1.93, 1.96, 1.97, 1.99, 1.101, 1.102, 1.118, 1.119, 1.120, 1.121, 1.123, 1.124, 1.128, 1.129, 1.131, 1.132, 1.133, 1.134, 1.135, 1.136, 1.137, 1.141, 1.143, 1.144, 1.145, 1.146, 1.147, 1.148, 1.149, 1.150, 1.151, 1.154, 1.156, 1.174, 1.192, 1.200, 1.203, 1.206, 1.207, 1.208, 1.209, 1.213, 1.214, 1.215, 1.219, 1.222, 1.226, 1.229, 1.232, 1.233, 1.236, 1.237, 1.238, 1.239, 1.243, 1.244, 1.245, 1.246, 1.247, 1.248, 1.253, 1.254, 1.255, 1.256, 1.258, 1.259, 1.260, 1.261, 1.263, 1.264, 1.265, 1.266, 1.267, 1.268, 1.269, 1.270, 1.271, 1.272, 1.273, 1.274, 1.275, 1.277, 1.279, 1.280, 1.281, 1.283, 1.285, 1.287, 1.288, 1.290, 1.291, 1.292, 1.293, 1.294, 1.295, 1.296, 1.297, 1.298, 1.299, 1.302 1.303, 1.304, 1.305, 1.306 and 1.312.

Example 3: Fungicidal Activity Against *Phakopsora pachyrhizi*/Soybean/Leaf Disc Preventative (Asian Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 h light/day and 75% rh. The activity of a compound is assessed as percent disease control compared to untreated when an appropriate level of disease damage appears in untreated check leaf disks (12 to 14 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.4, 1.5, 1.6, 1.7, 1.9, 1.10, 1.11, 1.15, 1.16, 1.17, 1.18, 1.19, 1.20, 1.21, 1.22, 1.23, 1.24, 1.25, 1.26, 1.27, 1.28, 1.30, 1.32, 1.33, 1.34, 1.35, 1.36, 1.39, 1.40, 1.41, 1.42, 1.43, 1.49, 1.56, 1.59, 1.61, 1.79, 1.85, 1.86, 1.87, 1.88, 1.90, 1.91, 1.93, 1.96, 1.99, 1.101, 1.102, 1.129, 1.136, 1.146, 1.147, 1.148, 1.149, 1.150, 1.151, 1.152, 1.153, 1.154, 1.156, 1.157, 1.158, 1.171, 1.174, 1.177, 1.184, 1.185, 1.186, 1.187, 1.190, 1.192, 1.193, 1.194, 1.195, 1.198, 1.200, 1.201, 1.203, 1.204, 1.205, 1.206, 1.207, 1.208, 1.209, 1.212, 1.213, 1.214, 1.215, 1.219, 1.222, 1.223, 1.224, 1.226, 1.227, 1.228, 1.229, 1.230, 1.232, 1.233, 1.236, 1.237, 1.238, 1.239, 1.240, 1.243, 1.244, 1.245, 1.246, 1.247, 1.248, 1.252, 1.253, 1.256, 1.259, 1.260, 1.261, 1.263, 1.264, 1.265, 1.266, 1.267, 1.268, 1.270, 1.273, 1.274, 1.275, 1.276, 1.277, 1.278, 1.279, 1.280, 1.283, 1.285, 1.286, 1.288, 1.290, 1.303, 1.304, 1.305, 1.306, 1.310 and 1.312.

Example 4: Fungicidal Activity Against *Glomerella Lagenarium* (*Colletotrichum Lagenarium*) Liquid Culture/Cucumber/Preventative (Anthracnose)

Conidia of the fungus from cryogenic storage are directly mixed into nutrient broth (PDB—potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

The following compounds at 20 ppm in the applied formulation give at least 80% disease control in this test when compared to untreated control under the same conditions, which show extensive disease development.

Compounds (from Table T1) 1.1, 1.2, 1.3, 1.4, 1.5, 1.6, 1.7, 1.8, 1.9, 1.10, 1.15, 1.16, 1.17, 1.18, 1.19, 1.20, 1.21, 1.22, 1.23, 1.24, 1.25, 1.26, 1.27, 1.28, 1.29, 1.30, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.54, 1.55, 1.56, 1.57, 1.58, 1.59, 1.60, 1.61, 1.62, 1.63, 1.64, 1.65, 1.66, 1.67, 1.68, 1.69, 1.70, 1.72, 1.73, 1.74, 1.75, 1.76, 1.77, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 1.100, 1.101, 1.102, 1.103, 1.104, 1.106, 1.107, 1.108, 1.109, 1.110, 1.111, 1.112, 1.113, 1.114, 1.115, 1.116, 1.117, 1.118, 1.119, 1.120, 1.121, 1.122, 1.124, 1.126, 1.127, 1.128, 1.129, 1.130, 1.131, 1.132, 1.133, 1.135, 1.136, 1.137, 1.138, 1.140, 1.142, 1.143, 1.144, 1.146, 1.147, 1.148, 1.149, 1.150, 1.151, 1.152, 1.154, 1.157, 1.158, 1.171, 1.174, 1.184, 1.185, 1.186, 1.188, 1.189, 1.190, 1.191, 1.192, 1.193, 1.194, 1.198, 1.200, 1.203, 1.204, 1.205, 1.206, 1.207, 1.208, 1.209, 1.212, 1.213, 1.214, 1.215, 1.219, 1.222, 1.223, 1.224, 1.226, 1.227, 1.228, 1.229, 1.232, 1.233, 1.236, 1.237, 1.238, 1.239, 1.240, 1.243, 1.244, 1.245, 1.246, 1.247, 1.248, 1.249, 1.250, 1.251, 1.252, 1.253, 1.254, 1.255, 1.256, 1.257, 1.258, 1.259, 1.260, 1.261, 1.262, 1.263, 1.264, 1.265, 1.266, 1.267, 1.268, 1.269, 1.270, 1.273, 1.274, 1.275, 1.276, 1.277, 1.278, 1.279, 1.280, 1.281, 1.283, 1.284, 1.285, 1.286, 1.287, 1.288, 1.289, 1.290, 1.292, 1.294, 1.295, 1.296, 1.297, 1.298, 1.299 1.302. 1.303, 1.304, 1.305, 1.306, 1.307, 1.309 and 1.312.

Example 5: Fungicidal Activity Against *Uromyces viciae-Fabael* Field Bean/Leaf Disc Preventative (Faba-Bean Rust)

Field bean leaf discs are placed on water agar in multiwell plates (96-well format) and 10 μl of the formulated test compound diluted in acetone and a spreader pipetted onto the leaf disc. Two hours after application leaf discs are inoculated by spraying a spore suspension on the lower leaf surface. The leaf discs are incubated in a climate cabinet at 22° C. with 18 hour day and 70% relative humidity. The activity of a compound is assessed as percent disease control compared to untreated when an appropriate level of disease damage appears in untreated check leaf disks (12 days after application).

The following compounds at 100 ppm in the applied formulation give at least 80% disease control in this test when compared to untreated control leaf discs under the same conditions, which show extensive disease development.

Compounds (from Table T1) 1.1, 1.2, 1.3, 1.4, 1.5, 1.6, 1.7, 1.8, 1.9, 1.10, 1.11, 1.12, 1.13, 1.14, 1.15, 1.16, 1.17, 1.18, 1.19, and 1.20.

The invention claimed is:
1. A compound of formula (I):

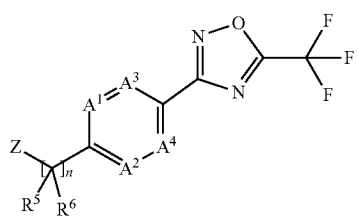

wherein
n is 1 or 2;
$A^1$ represents N or $CR^1$, wherein $R^1$ represents hydrogen, halogen, methyl, ethyl, difluoromethyl, trifluoromethyl, methoxy, ethoxy, or difluoromethoxy;
$A^2$ represents N or $CR^2$, wherein $R^2$ represents hydrogen, halogen, methyl, ethyl, difluoromethyl, trifluoromethyl, methoxy, ethoxy, or difluoromethoxy;
$A^3$ represents N or $CR^3$, wherein $R^3$ represents hydrogen or halogen;
$A^4$ represents N or $CR^4$, wherein $R^4$ represents hydrogen or halogen; and
wherein 0 or 1 or 2 of $A^1$, $A^2$, $A^3$ and $A^4$ are N;
$R^5$ and $R^6$ are independently selected from hydrogen, $C_{1-4}$alkyl, halogen, cyano, trifluoromethyl and difluoromethyl, or
$R^5$ and $R^6$ together with the carbon atom they share form a cyclopropyl;
Z is selected from $Z^1$, $Z^2$, $Z^3$, $Z^4$, $Z^5$ or $Z^6$; wherein
$Z^1$ represents a heterocyclyl linked to $C(R^5)(R^6)$ via a C—C bond, wherein the heterocyclyl moiety is a 5- or 6-membered non-aromatic ring which contains 1 nitrogen in the ring system and optionally comprises 1, 2, or 3 additional ring members independently selected from the group consisting of O, S, N, $NR^7$, C(O), or $S(O)_2$, with the proviso that the heterocycle cannot contain 2 contiguous atoms selected from O and S;
$Z^2$ represents a heteroaryl linked to $C(R^5)(R^6)$ via a C—C bond, wherein the heteroaryl moiety is a 5- or 6-membered aromatic ring which contains 1 nitrogen atom in the ring system and optionally comprises 1, 2, or 3 additional ring members independently selected from the group consisting of O, S, N, or NR';
$R^7$ is hydrogen, $C_{1-4}$ alkyl, $C_{1-4}$ alkoxy, formyl, $C_{1-4}$ alkylcarbonyl, $C_{1-4}$ alkoxycarbonyl, N—$C_{1-4}$alkylaminocarbonyl, N,N-di$C_{1-4}$alkylaminocarbonyl, $C_{1-4}$alkylsulfonyl, N—$C_{1-2}$alkylaminosulfonyl, or N,N-di$C_{1-2}$alkylaminosulfonyl; and
wherein for $Z^1$ and $Z^2$, the heterocyclyl or heteroaryl moiety is optionally substituted by 1, 2 or 3 substituents, which may be the same or different, selected from $R^8$;
$R^8$ is cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, N—$C_{1-4}$alkylamino, N,N-di$C_{1-4}$alkylamino, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{1-4}$alkoxycarbonylamino;

$Z^3$ represents a heterocyclyl linked to $C(R^5)(R^6)$ via a C—N bond, wherein the heterocyclyl moiety is selected from imidazolidinyl, pyrazolidinyl, oxazolidinyl, isoxazolidinyl, 4,5-dihydrooxazolyl, thiazolidinyl, thiazolinyl and thiomorpholinyl;
$Z^4$ represents a heteroaryl linked to $C(R^5)(R^6)$ via a C—N bond, wherein the heteroaryl moiety is a 5-membered aromatic ring which contains 1 to 4 nitrogen atoms in the ring system; and
wherein for $Z^3$ and $Z^4$, the heterocyclyl or heteroaryl moiety is optionally substituted by 1, 2 or 3 substituents, which may be the same or different, selected from $R^{10}$;
wherein $R^{10}$ represents:
(i) cyano, halogen, hydroxy, amino, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{1-4}$alkylsulfanyl, $C_{1-4}$alkylsulfinyl, $C_{1-4}$alkylsulfonyl, $C_{1-4}$haloalkylsulfanyl, $C_{3-4}$alkenyloxy, $C_{3-4}$alkynyloxy, N—$C_{1-4}$alkylamino, N,N-di$C_{1-4}$alkylamino, formyl, hydroxycarbonyl, $C_{1-4}$alkylcarbonyl, $C_{1-4}$alkoxycarbonyl, $C_{1-4}$alkylcarbonylamino, aminocarbonyl, N—$C_{1-4}$alkylaminocarbonyl, N—$C_{2-4}$alkenylaminocarbonyl, N—$C_{2-4}$alkynylaminocarbonyl, N,N-di$C_{1-4}$alkylaminocarbonyl, N-morpholinoaminocarbonyl, 4alkoxyaminocarbonyl, N—$C_{1-4}$alkyl-N—$C_{1-4}$alkoxyaminocarbonyl, $C_{1-4}$alkoxycarbonylamino, $C_{1-4}$alkoxycarbonylamino$C_{1-4}$alkyl, N—$C_{1-4}$alkoxy$C_{1-4}$alkylaminocarbonyl, phenylcarbonyloxy$C_{1-4}$ alkyl, phenylcarbonylamino$C_{1-4}$alkyl, $C_{1-4}$alkylcarbonyloxy, $C_{1-4}$haloalkylcarbonyloxy, $C_{1-4}$alkylcarbonyloxy$C_{1-4}$alkyl, $C_{1-4}$alkylcarbonylamino$C_{1-4}$alkyl, or $(C_{1-4}$alkyl$)_3$Si—; or
(ii) —$C(O)N(R^a)(R^b)$, wherein:
$R^a$ is hydrogen, $C_{1-4}$alkyl, $C_{1-4}$haloalkyl, $C_{1-4}$cyanoalkyl, hydroxy$C_{1-4}$alkyl, $C_{1-2}$alkoxy$C_{1-4}$alkyl, $C_{1-2}$haloalkoxy$C_{1-4}$alkyl, $C_{3-5}$alkenyl, $C_{3-5}$alkynyl, amino$C_{1-4}$ alkyl, N—$C_{1-4}$alkylamino$C_{1-4}$alkyl, N,N-di$C_{1-4}$alkylamino$C_{1-4}$alkyl, formyl, $C_{1-4}$alkylcarbonyl, $C_{3-4}$cycloalkylcarbonyl, $C_{1-4}$haloalkylcarbonyl, $C_{1-4}$alkylcarbonyl$C_{1-4}$alkyl, $C_{1-4}$alkoxycarbonyl$C_{1-4}$alkyl, $C_{1-4}$alkylcarbonyloxy$C_{1-4}$alkyl, N—$C_{1-4}$alkylaminocarbonyl$C_{1-4}$alkyl, N,N-di$C_{1-4}$alkylaminocarbonyl$C_{1-4}$alkyl, $C_{1-4}$alkylsulfanyl$C_{1-4}$alkyl, $C_{1-4}$alkylsulfonyl, $C_{1-4}$alkylsulfonyl$C_{1-4}$alkyl, $C_{1-4}$alkylsulfonylamino$C_{1-4}$alkyl, $C_{1-4}$alkoxycarbonylamino$C_{1-4}$ alkyl, $C_{1-4}$alkylcarbonylamino$C_{1-4}$alkyl, $C_{1-4}$alkoxycarbonylamino$C_{1-4}$alkyl, or $C_{1-4}$haloalkylcarbonylamino$C_{1-4}$alkyl, and
$R^b$ is hydrogen, hydroxyl, $C_{1-4}$alkyl, $C_{1-4}$haloalkyl, $C_{1-4}$cyanoalkyl, hydroxy$C_{1-4}$alkyl, $C_{1-2}$alkoxy$C_{1-4}$ alkyl, $C_{3-4}$alkenyl, $C_{3-4}$alkynyl, $C_{3-4}$cycloalkyl, $C_{3-4}$cycloalkyl$C_{1-2}$alkyl, $C_{1-4}$alkoxy, $C_{3-4}$alkenyloxy, $C_{3-4}$haloalkenyloxy, or $C_{3-4}$alkynyloxy; or
$R^a$ and $R^b$ together with the nitrogen atom to which they are bonded, form a 4-, 5- or 6-membered cycle optionally containing an additional heteroatom or group selected from O, S, $S(O)_2$, C(O) and $NR^c$, wherein $R^c$ is hydrogen, methyl, methoxy, formyl or acyl; or
(iii) —$C(O)O—R^d$, wherein:
$R^d$ is hydrogen, $C_{1-4}$alkyl, $C_{1-4}$haloalkyl, $C_{1-4}$cyanoalkyl, hydroxy$C_{1-4}$alkyl, $C_{1-2}$alkoxy$C_{1-4}$alkyl, $C_{1-2}$alkoxy$C_{1-2}$ alkoxy$C_{1-4}$alkyl, $C_{1-2}$haloalkoxy$C_{1-4}$ alkyl, $C_{3-5}$alkenyl, $C_{3-4}$haloalkenyl, $C_{3-4}$alkenyloxy$C_{1-4}$ alkyl, $C_{3-5}$alkynyl, $C_{3-4}$alkynyloxy$C_{1-4}$alkyl, N—$C_{1-3}$alkylamino$C_{1-4}$alkyl, N,N-di-$C_{1-3}$alkylaminoC$_{1-4}$alkyl, C$_{1-4}$alkoxycarbonylaminoC$_{1-4}$alkyl or C$_{1-4}$alkylcarbonylaminoC$_{1-4}$alkyl; or wherein for Z$^4$, the heteroaryl moiety is optionally substituted by 1 substituent selected from R$^{11}$ and further optionally substituted by 1 or 2 substituents, which may be the same or different, selected from R$^{10}$;

wherein R$^{11}$ represents:

(i) C$_{3-8}$cycloalkyl, C$_{3-8}$cycloalkylC$_{1-2}$alkyl, N—C$_{3-8}$cycloalkylaminocarbonyl, N—C$_{3-8}$cycloalkylC$_{1-2}$alkylaminocarbonyl, phenyl, phenylC$_{1-2}$alkyl, phenoxyC$_{1-2}$alkyl, phenylC$_{1-2}$alkylsulfanyl, heteroaryl, heteroarylC$_{1-2}$alkyl, heteroaryloxyC$_{1-2}$alkyl, N-heteroarylaminocarbonyl, wherein the heteroaryl moiety is a 5- or 6-membered aromatic ring which comprises 1, 2, 3 or 4 heteroatoms individually selected from N, O and S, heterocyclyl, heterocyclylC$_{1-6}$alkyl, heterocyclylcarbonyl wherein the heterocyclyl moiety is a 4- to 6-membered non-aromatic ring which comprises 1 or 2 heteroatoms individually selected from N, O and S, benzodioxolyl, and wherein any of said cycloalkyl, phenyl, heteroaryl, heterocyclyl and benzodioxolyl moieties are optionally substituted by 1, 2 or 3 substituents, which may be the same or different, selected from R$^{12}$; or (ii) —C(O)N(R$^e$)(R$^f$), wherein:

R$^e$ is C$_{3-5}$cycloalkyl, C$_{3-5}$cycloalkylC$_{1-2}$alkyl, phenyl, phenylC$_{1-2}$alkyl, heterocyclyl, heterocyclylC$_{1-2}$alkyl, wherein the heterocyclyl moiety is a 4- to 6-membered non-aromatic ring which comprises 1, 2, or 3 ring members independently selected from the group consisting of O, S, N or S(O)$_2$, with the proviso that the heterocycle cannot contain 2 contiguous atoms selected from O and S, heteroaryl, heteroarylC$_{1-2}$alkyl, wherein the heteroaryl moiety is a 5- or 6-membered aromatic ring which comprises 1, 2, 3 or 4 heteroatoms individually selected from N, O and S, and wherein the cycloalkyl, phenyl, heterocyclyl or heteroaryl moiety is optionally substituted by 1 or 2 substituents, which may be the same or different, selected from hydroxyl, amino, formyl, acyl, cyano, halogen, methyl, difluoromethyl, trifluoromethyl, methoxy, ethoxy, or difluoromethoxy, or the cycloalkyl or heterocyclyl moiety is optionally substituted by 1 or 2 groups which are oxo (=O), and R$^f$ is hydrogen, C$_{1-4}$alkyl, C$_{1-4}$alkoxy C$_{1-4}$ haloalkyl, C$_{3-4}$alkenyl, C$_{3-4}$alkynyl, C$_{3-4}$cycloalkyl, or C$_{3-4}$cycloalkylC$_{1-2}$alkyl; or (iii) —C(O)O—R$^g$, wherein:

R$^g$ is C$_{3-5}$cycloalkyl, C$_{3-5}$cycloalkylC$_{1-2}$alkyl, phenyl, phenylC$_{1-2}$alkyl, heterocyclyl, heterocyclylC$_{1-2}$alkyl, wherein the heterocyclyl moiety is a 4- to 6-membered non-aromatic ring which comprises 1, 2, or 3 ring members independently selected from the group consisting of O, S, N or S(O)$_2$, with the proviso that the heterocycle cannot contain 2 contiguous atoms selected from O and S, heteroaryl, heteroarylC$_{1-2}$alkyl, wherein the heteroaryl moiety is a 5- or 6-membered aromatic ring which comprises 1, 2, 3 or 4 heteroatoms individually selected from N, O and S, and wherein the cycloalkyl, phenyl, heterocyclyl or heteroaryl moiety is optionally substituted by 1 or 2 substituents, which may be the same or different, selected from hydroxyl, formyl, acyl, cyano, halogen, methyl, difluoromethyl, trifluoromethyl, methoxy, ethoxy, or difluoromethoxy, or the cycloalkyl or heterocyclyl moiety is optionally substituted by 1 or 2 groups which are oxo (=O); or (iv) (C$_{1-4}$alkyl)-O—N=C(R$^h$)—, (C$_{1-4}$haloalkyl)-O—N=C(R$^h$)—, (C$_{2-4}$alkenyl)-O—N=C(R$^h$), (C$_{2-4}$alkynyl)-O—N=C(R$^h$)—, benzyl-O—N=C(R$^h$)—, wherein R$^h$ is hydrogen or methyl;

R$^{12}$ is cyano, fluoro, chloro, bromo, methyl, ethyl, formyl, methoxy, ethoxy, difluoromethyl, trifluoromethyl, difluoromethoxy or ethoxycarbonyl;

Z$^5$ represents a heterobicyclyl linked to C(R$^5$)(R$^6$) via a C—N bond, wherein the heterobicyclyl moiety is a 7- to 10-membered saturated, partially saturated or partially aromatic fused ring system which contains 1 nitrogen in the ring system and optionally comprises 1, 2, or 3 additional ring members independently selected from the group consisting of O, S, N, NR$^{13}$, C(O) or S(O)$_2$, with the proviso that the heterobicyclyl cannot contain 2 contiguous atoms selected from O and S;

Z$^6$ represents a heterodiaryl linked to C(R$^5$)(R$^6$) via a C—N bond, wherein the heterdioaryl moiety is a 9-membered di-aromatic system which contains 1 to 4 nitrogen atoms in the ring system;

R$^{13}$ is hydrogen, C$_{1-4}$alkyl, C$_{1-4}$alkoxy, formyl, C$_{1-4}$alkylcarbonyl, C$_{1-4}$alkoxycarbonyl, N—C$_{1-4}$alkylaminocarbonyl, or N,N-diC$_{1-4}$alkylaminocarbonyl; and wherein for Z$^5$ and Z$^6$, the heterobicyclyl or heterodiaryl moiety is optionally substituted by 1, 2, 3 or 4 substituents, which may be the same or different, selected from R$^{14}$;

R$^{14}$ is cyano, halogen, hydroxy, formyl, C$_{1-4}$alkyl, C$_{2-4}$alkenyl, C$_{2-4}$alkynyl, C$_{1-4}$haloalkyl, cyanoC$_{1-4}$alkyl, C$_{2-4}$haloalkenyl, C$_{1-4}$alkoxy, C$_{1-4}$haloalkoxy, C$_{3-4}$alkenyloxy, C$_{3-4}$alkynyloxy, N—C$_{1-4}$alkylamino, N,N-diC$_{1-4}$alkylamino, C$_{1-4}$alkylcarbonyl, C$_{1-4}$alkoxycarbonyl, C$_{1-4}$alkylcarbonylamino, N—C$_{1-4}$alkylaminocarbonyl, N,N-diC$_{1-4}$alkylaminocarbonyl or C$_{1-4}$alkoxycarbonylamino, and additionally oxo (=O) for Z$^5$; or wherein for Z$^5$ and Z$^6$, the heterobicyclyl or heterodiaryl moiety is optionally substituted by 1 substituent selected from R$^{15}$ and further optionally substituted by 1 or 2 substituents, which may be the same or different, selected from R$^{14}$;

R$^{15}$ is pyridinyl, benzodioxolyloxy, phenoxy or phenylsulfanyl, wherein phenoxy and phenylsulfanyl are optionally substituted by 1, 2 or 3 substituents, which may be the same or different, selected from chloro, fluoro, bromo, methyl, ethyl, methoxy and ethoxy; or a salt or an N-oxide thereof.

2. The compound according to claim 1, wherein A$^1$ is N or CR$^1$ wherein R$^1$ is hydrogen, chloro, fluoro, methyl, methoxy or trifluoromethyl, and A$^2$, A$^3$ and A$^4$ are C—H.

3. The compound according to claim 1, wherein A$^1$, A$^2$, A$^3$ and A$^4$ are C—H.

4. The compound according to claim 1, wherein A$^3$ is CR$^3$ and R$^3$ is halogen, and A$^1$, A$^2$ and A$^4$ are C—H.

5. The compound according to claim 1, wherein R$^5$ and R$^6$ are hydrogen, or R$^5$ is hydrogen and R$^6$ is methyl.

6. The compound according to claim 1, wherein Z is Z$^4$.

7. The compound according to claim 6, wherein the heteroaryl moiety of Z$^4$ is optionally substituted by 1, 2 or 3 substituents, which may be the same or different, selected from R$^{10}$;

R$^{10}$ is cyano, halogen, hydroxy, amino, C$_{1-4}$alkyl, C$_{1-4}$haloalkyl, C$_{1-4}$alkoxy, C$_{1-4}$alkoxyC$_{1-4}$alkyl, C$_{1-4}$alkylsulfanyl, C$_{1-4}$haloalkylsulfanyl, formyl, hydroxycarbonyl, C$_{1-4}$alkylcarbonyl, C$_{1-4}$alkoxycarbonyl, C$_{3-4}$alkenyloxycarbonyl, C$_{3-4}$alkynyloxycarbonyl, aminocarbonyl, N—C$_{1-4}$alkylaminocarbonyl, N—C$_{3-4}$alkenylaminocarbonyl, N—C$_{2-4}$alkynylaminocarbonyl, N,N-diC$_{1-4}$alkylaminocarbonyl, N-morpholinoaminocarbonyl, N—C$_{1-4}$alkoxyaminocarbonyl, N—C$_{1-4}$alkyl-N—C$_{1-4}$alkoxyaminocarbonyl, N—C$_{1-4}$alkoxyC$_{1-4}$alkylaminocarbonyl, phenylcarbonylaminoC$_{1-4}$alkyl, C$_{1-4}$alkylcarbonyloxyC$_{1-4}$alkyl, C$_{1-4}$alkylcarbonylaminoC$_{1-4}$alkyl, C$_{1-4}$alkoxycarbonylaminoC$_{1-4}$alkyl, or (C$_{1-4}$alkyl)$_3$Si—; or Z$^4$ is optionally substituted by 1 substituent selected from R$^{11}$ and further optionally substituted by 1 or 2 substituents selected from R$^{10}$; wherein R$^{11}$ is C$_{3-6}$cycloalkyl, C$_{3-6}$cycloalkylC$_{1-2}$alkyl, N—C$_{3-6}$cycloalkylaminocarbonyl, N—C$_{3-6}$cycloalkylC$_{1-2}$alkylaminocarbonyl, C$_{3-4}$cycloalkoxycarbonyl, C$_{3-4}$cycloalkylC$_{1-2}$alkoxycarbonyl, phenyl, phenylC$_{1-2}$alkyl, phenoxyC$_{1-2}$alkyl, phenylC$_{1-2}$alkylsulfanyl, N-phenylaminocarbonyl, heterocyclyl, heterocyclylcarbonyl, wherein the heterocyclyl moiety is a 4- to 6-membered non-aromatic ring which comprises 1, 2, or 3 ring members independently selected from the group consisting of O, S, N or S(O)$_2$, with the proviso that the heterocycle cannot contain 2 contiguous atoms selected from O and S, heteroaryl, heteroarylC$_{1-2}$alkyl, heteroaryloxyC$_{1-2}$alkyl, wherein the heteroaryl moiety is a 5- or 6-membered aromatic ring which comprises 1, 2 or 3 heteroatoms individually selected from N, O and S, benzodioxolyl, and wherein any of said cycloalkyl, phenyl, heterocyclyl, heteroaryl and benzodioxolyl moieties are optionally substituted by 1, 2 or 3 substituents, which may be the same or different, selected from R$^{12}$; and R$^{12}$ is fluoro, chloro, bromo, methyl, ethyl, or methoxy.

8. The compound according to claim 6, wherein Z$^4$ is pyrazolyl, imidazolyl or triazolyl, wherein pyrazolyl, imidazolyl or triazolyl are optionally substituted by 1 or 2 substituents, which may be the same or different, selected from R$^{10}$; or pyrazolyl, imidazolyl or triazolyl are optionally substituted by 1 substituent selected from R$^{11}$ and are further optionally substituted by 1 substituent selected from R$^{10}$.

9. The compound according to claim 8, wherein Z$^4$ is pyrazol-1-yl, 1,2,3-triazol-1-yl or 1,2,4-triazol-1-yl, wherein pyrazol-1-yl is optionally substituted by 1 substituent selected from R$^{10}$ or R$^{11}$, wherein R$^{10}$ is hydroxycarbonyl, methoxycarbonyl, ethoxycarbonyl, n-propoxycarbonyl, i-propoxycarbonyl, t-butoxycarbonyl, aminocarbonyl, methylaminocarbonyl, ethylaminocarbonyl, methoxyethylaminocarbonyl, propargylaminocarbonyl, N-morpholinoaminocarbonyl, N,N-dimethylaminocarbonyl, N,N-diethylaminocarbonyl, N-methyl-N-methoxyaminocarbonyl or N-methoxyaminocarbonyl, and R$^{11}$ is cyclopropylaminocarbonyl, cyclobutylaminocarbonyl, cyclopentylaminocarbonyl or cyclohexylaminocarbonyl; and 1,2,3-triazol-1-yl or 1,2,4-triazol-1-yl is optionally substituted by 1 substituent selected from R$^{10}$ or R$^{11}$, wherein R$^{10}$ is cyano, ethynyl, fluoro, chloro, methyl, ethyl, trifluoromethyl, methoxy, ethoxycarbonyl or ethoxymethyl, and R$^{11}$ is cyclopropyl.

10. The compound according to claim 1, wherein Z is Z$^6$ selected from indolyl, indazolyl, benzimidazolyl, pyrrolopyridinyl or triazolopyridinyl.

11. The compound according to claim 10, wherein:
indolyl, indazolyl, benzimidazolyl, pyrrolopyridinyl or triazolopyridinyl is optionally substituted by 1, 2 or 3 substituents, which may be the same or different, selected from R$^{14}$, wherein R$^{14}$ is cyano, halogen, hydroxy, formyl, C$_{1-4}$alkyl, C$_{1-4}$haloalkyl, C$_{1-4}$alkoxy, C$_{1-4}$alkylcarbonyl, or C$_{1-4}$alkoxycarbonyl; or indolyl, indazolyl, benzimidazolyl, pyrrolopyridinyl or triazolopyridinyl is optionally substituted by 1 substituent selected from R$^{15}$ and further optionally substituted by 1 or 2 substituents selected from R$^{14}$, wherein R$^{15}$ is pyridinyl, benzodioxolyloxy, phenoxy or phenylsulfanyl, wherein phenoxy and phenylsulfanyl are optionally substituted by 1, 2 or 3 substituents, which may be the same or different, selected from chloro, fluoro, bromo, methyl, ethyl, methoxy and ethoxy.

12. An agrochemical composition comprising a fungicidally effective amount of a compound of formula (I) according to claim 1.

13. The composition according to claim 12, further comprising at least one additional active ingredient and/or an agrochemically-acceptable diluent or carrier.

14. The compound according to claim 1, said compound being selected from:

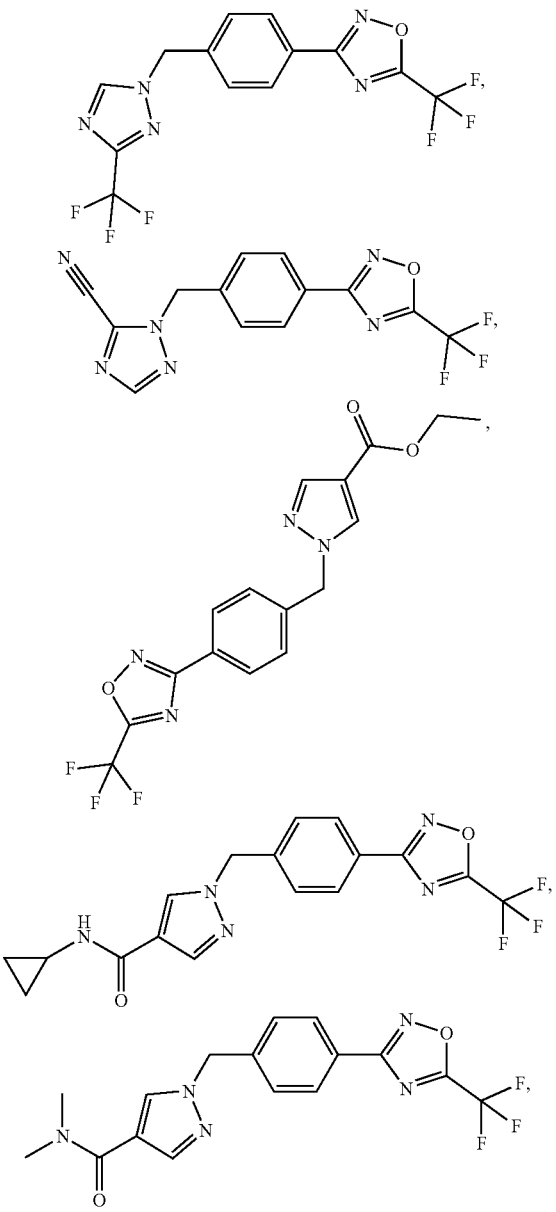

-continued
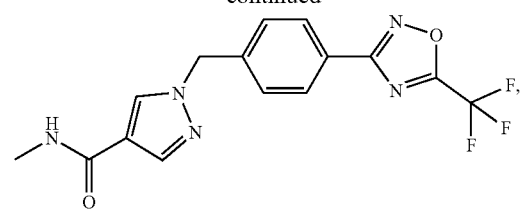
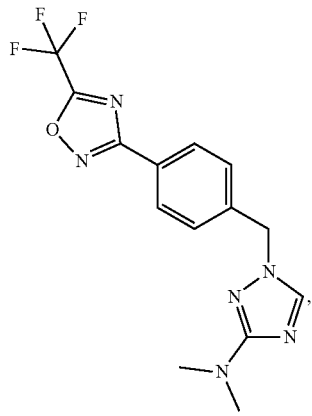
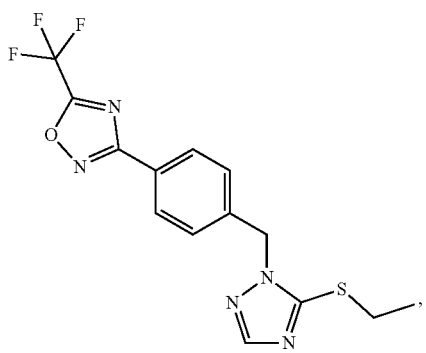
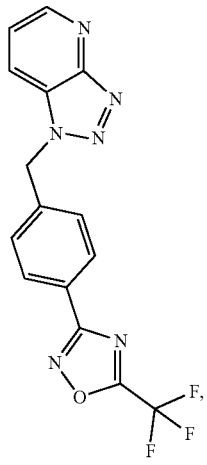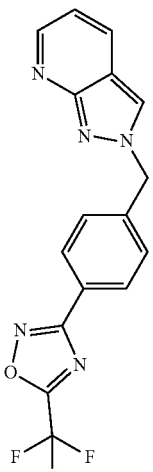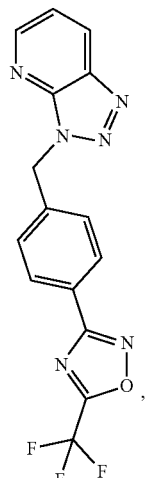
-continued
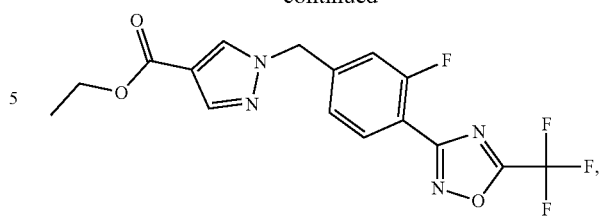
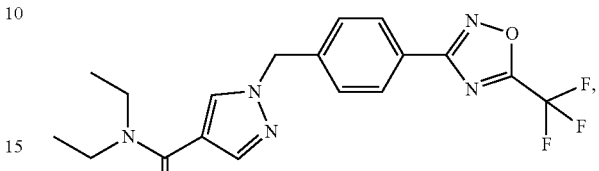
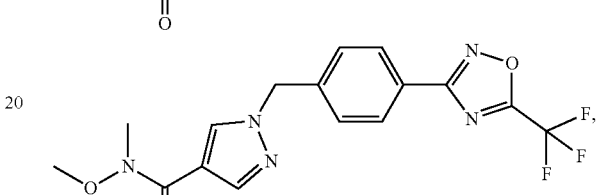
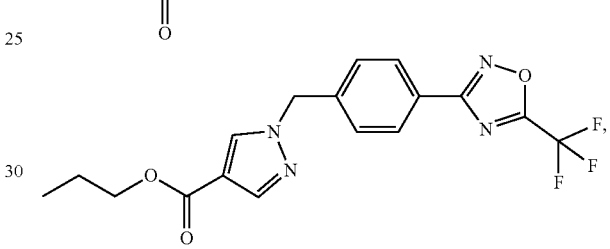
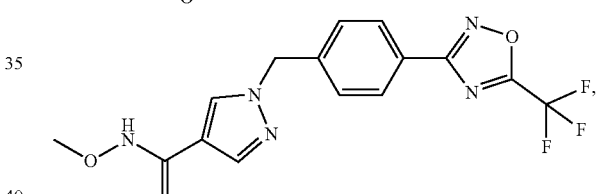
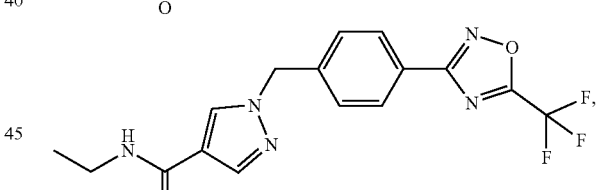
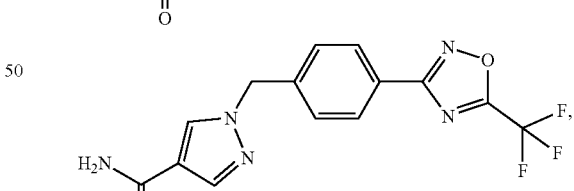
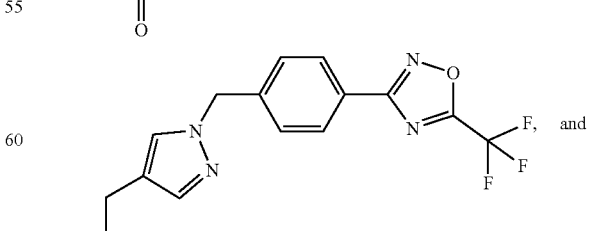

-continued
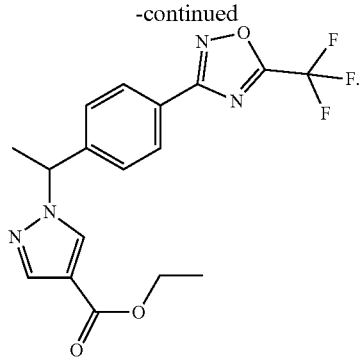

UNITED STATES PATENT AND TRADEMARK OFFICE
CERTIFICATE OF CORRECTION

PATENT NO. : 10,798,941 B2
APPLICATION NO. : 16/068638
DATED : October 13, 2020
INVENTOR(S) : Thomas James Hoffman et al.

Page 1 of 1

It is certified that error appears in the above-identified patent and that said Letters Patent is hereby corrected as shown below:

In the Claims

Claim 1, Column 171, Line 51, 'NR';' should read -- $NR^7$; --.

Claim 14, Column 177, Lines 40-55, the structure ' ' should be -- --.

Signed and Sealed this
Second Day of February, 2021

Drew Hirshfeld
*Performing the Functions and Duties of the
Under Secretary of Commerce for Intellectual Property and
Director of the United States Patent and Trademark Office*